(12) United States Patent
Dietliker et al.

(10) Patent No.: US 10,928,728 B2
(45) Date of Patent: Feb. 23, 2021

(54) PHOTOACTIVABLE NITROGEN BASES

(71) Applicant: BASF SE, Ludwigshafen (DE)

(72) Inventors: Kurt Dietliker, Allschwil (CH); Katharina Misteli, Basel (CH); Katia Studer, Rixheim (FR); Tunja Jung, Rheinfelden-Herten (DE); Lother Alexander Engelbrecht, KI Heerenveen (NL)

(73) Assignee: BASF SE, Ludwigshafen (DE)

( * ) Notice: Subject to any disclaimer, the term of this patent is extended or adjusted under 35 U.S.C. 154(b) by 195 days.

(21) Appl. No.: 15/880,695

(22) Filed: Jan. 26, 2018

(65) Prior Publication Data

US 2018/0217498 A1 Aug. 2, 2018

Related U.S. Application Data

(62) Division of application No. 12/532,840, filed as application No. PCT/EP2008/053456 on Mar. 25, 2008, now Pat. No. 9,921,477.

(30) Foreign Application Priority Data

Apr. 3, 2007 (EP) .................................... 07105510

(51) Int. Cl.
*G03F 7/038* (2006.01)
*C07D 487/04* (2006.01)
(Continued)

(52) U.S. Cl.
CPC .......... *G03F 7/0382* (2013.01); *C07D 487/04* (2013.01); *C08F 2/50* (2013.01); *G03F 7/0045* (2013.01)

(58) Field of Classification Search
CPC ....... C08J 3/28; C08J 3/24; C08J 7/123; C08J 2323/06; A61L 27/44; A61L 27/505;
(Continued)

(56) References Cited

U.S. PATENT DOCUMENTS 5,219,958 A 6/1993 Noomen et al.
5,998,496 A 12/1999 Hassoon et al.
(Continued)

FOREIGN PATENT DOCUMENTS

EP 448154 A1 9/1991
EP 898202 A1 2/1999
(Continued)

OTHER PUBLICATIONS

Bartl et al., Photo-heterolysis and -homolysis of substituted diphenylmethyl halides, acetates, and phenyl ethers in acetonitrile: characterization of diphenylmethyl cations and radicals generated by 248-nm laser flash photolysis, J. Am. Chem. Soc., 112:6918-28 (1990).
Dietliker, Photobase Generators, Chapter IV, pp. 479-517, in: Crivello et al., "Photoinitiators for free radical cationic and anionic photopolymerisation", 2nd edition, Wiley & Sons (1998).
Frechet, The photogeneration of acid and base within polymer coatings: Approaches to polymer curing and imaging, Pure & Appl. Chem., 64(9):1239-48 (1992).
(Continued)

*Primary Examiner* — Jessica M Roswell
(74) *Attorney, Agent, or Firm* — Marshall, Gerstein & Borun LLP

(57) ABSTRACT

Compounds of the Formula (I), (II) and (III) wherein Ar is for example phenylene, biphenyleneor naphthylene, all of which are unsubstituted or substituted by $C_1$-$C_4$-alkyl, $C_2$-$C_4$-alkenyl, CN, $OR_{11}$, $SR_{11}$, $CH_2OR_{11}$, $COOR_{12}$, $CONR_{12}R_{13}$ or halogen; $R_1$, $R_2$, $R_7$ and $R_8$ independently of one another other are hydrogen or $C_1$-$C_6$-alkyl; $R_3$ and $R_5$ together and $R_4$ and $R_6$ together form a $C_2$-$C_6$-alkylene bridge which is unsubstituted or substituted by one ore more $C_1$-$C_4$-alkyl; $R_{11}$ is hydrogen or $C_1$-$C_6$-alkyl; $R_{12}$ and $R_{13}$ independently of one another for example are hydrogen, phenyl, $C_1$-$C_{18}$-alkyl, $C_1$-$C_{18}$-alkyl which is interrupted by one or more O; n is 1-10; X is O, S or $NR_{10}$; A and $A_1$ are suitable linking groups; are suitable as photolatent bases.

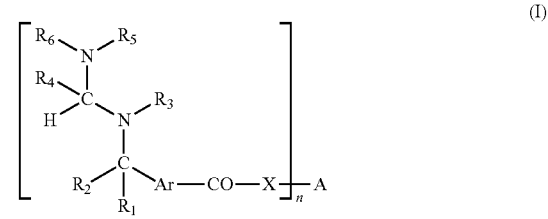

(I)

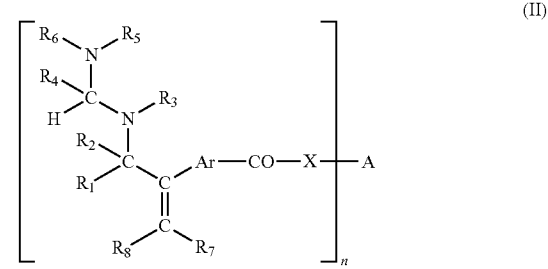

(II)

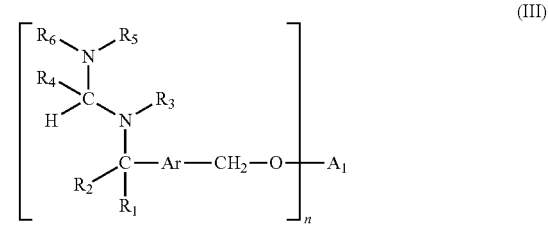

(III)

18 Claims, No Drawings

(51) Int. Cl.
*C08F 2/50* (2006.01)
*G03F 7/00* (2006.01)
*G03F 7/004* (2006.01)

(58) Field of Classification Search
CPC ...... A61L 27/16; C08L 23/06; C08L 2314/02;
C08L 2312/06; C08L 2207/068; C08L
2205/02; C08L 23/04; A61K 31/355;
Y10T 428/269; C08K 5/005
See application file for complete search history.

(56) References Cited

U.S. PATENT DOCUMENTS

| | | | |
|---|---|---|---|
| 6,087,070 | A | 7/2000 | Turner et al. |
| 6,489,374 | B1 | 12/2002 | Baudin et al. |
| 7,538,104 | B2 | 5/2009 | Baudin et al. |
| 8,252,784 | B2 * | 8/2012 | Baudin ................ C07D 487/04 514/214.02 |
| 2001/0027253 | A1 | 10/2001 | Hall-Goulle et al. |
| 2002/0032248 | A1 | 3/2002 | Klinkenberg et al. |
| 2004/0242867 | A1 | 12/2004 | Baudin et al. |
| 2007/0249484 | A1 | 10/2007 | Benkhoff et al. |
| 2009/0298962 | A1 | 12/2009 | Studer et al. |
| 2010/0105794 | A1 | 4/2010 | Dietliker et al. |
| 2010/0236707 | A1 | 9/2010 | Studer et al. |

FOREIGN PATENT DOCUMENTS

| | | |
|---|---|---|
| WO | WO-94/28075 A1 | 12/1994 |
| WO | WO-97/16406 A1 | 5/1997 |
| WO | WO-97/31033 A1 | 8/1997 |
| WO | WO-98/32756 A1 | 7/1998 |
| WO | WO-98/38195 A1 | 9/1998 |
| WO | WO-98/41524 A1 | 9/1998 |
| WO | WO-00/10964 A1 | 3/2000 |
| WO | WO-01/92362 A1 | 12/2001 |
| WO | WO-03/033500 A1 | 4/2003 |
| WO | WO-2006/008251 A2 | 1/2006 |

OTHER PUBLICATIONS

Tachi et al., Photochemical reactions of quaternary ammonium dithiocarbamates as photobase generators and their use in the photoinitiated thermal crosslinking of poly(glycidyl methacrylate), J. Polymer Sci. Part A, 39(9):1329-41 (2001).

* cited by examiner

PHOTOACTIVABLE NITROGEN BASES

CROSS-REFERENCE TO RELATED APPLICATIONS

This application is a division of U.S. application Ser. No. 12/532,840 (incorporated herein by reference in its entirety), having a 371(c) date of Sep. 24, 2009, which is the National Stage entry of International Application No. PCT/EP2008/053456, filed Mar. 25, 2008, which claims priority to European patent application number EP 07105510.7, filed Apr. 3, 2007.

The invention relates to amines with benzylic substitution which can be converted photochemically into amidine derivatives and to a process for photochemically preparing the amidine derivatives. The invention further relates to base-polymerizable or base-crosslinkable compositions comprising the amines, to a process for conducting photochemically induced, base-catalysed reactions, and to the use of the amines as photoinitiators for base-catalysed reactions, as well as the use of the compounds as starting materials for preparing multifunctional photolatent bases.

The photolytic generation of bases, and photopolymerization reactions or photoinduced crosslinking reactions triggered by such photogenerated amines, is known and a general description is, for example, published by *Fréchet, J. Pure and Appl. Chem.* (1992), 64, 1239 and *Dietliker in "Photoinitiators for Free Radical, Cationic and Anionic Polymerisation"*, Wiley/S/TA Technology 1998, Chapter IV, pages 479-517. Irradiation of most compounds described produces primary or secondary amines which find mainly use as photogenerated crosslinkers. As catalysts for base-catalysed reactions, primary or secondary amines are not very suitable.

A few photolabile compounds which generate tertiary amines are known. Those described include, for example, benzyl- and di- or triphenylmethane-ammonium salts as described for example by Bart/et al., *J. Am. Chem Soc.* (1990), 112, 6918 and N-(benzophenone-methyl)tri-N-alkylammonium triphenylborates as given for example in WO 97/16406. The irradiation of these compounds produces trialkylamines, which are better suited to use as catalysts for base-catalysed reactions than are primary or secondary amines.

N-phenacylammonium salts with N,N-dimethyldithiocarbamate counterions likewise liberate tertiary amines on irradiation as taught by Tachi et al., *J. Polym. Sci. Part A: Polym. Chem.* (2001), 39, 1329. All of these compounds are salts whose solubility in a variety of formulations is limited.

From EP 898202 and WO 01/92362 it is known that α-amino ketones also are capable of liberating tertiary amines.

Further suitable for base-catalysed reactions are amines of the amidine or guanidine type as for example bicyclic amidines, especially 1,8-diazabicyclo[5.4.0]undec-7-ene (DBU) and 1,5-diazabicyclo[4.3.0]non-5-ene (DBN), and also tetramethylguanidine (TMG), are outstandingly suitable catalysts for such systems. EP 448154, for example, discloses the use of amidine bases such as DBU, DBN or TMG in the form of their salts. These bases are activated thermally.

A few photolatent bases from which strong bases suitable for the catalysis of these reactions can be liberated on exposure to light, are known. For example, WO 94/28075 describes UV-deblockable bases of the amine, ammonium compound and phosphane type. As blocking agents, mention is made in particular of α-keto carboxylic acids, aromatic or N-heterocyclic formic, acetic or oxoacetic acid derivatives, with which the amine bases are converted into their non-reactive salts, and which are deblocked on irradiation. Since the salts in question are ionic salts, their solubility in the formulations is limited.

WO 97/31033 describes the photochemical liberation of bases having a $pK_a \geq 12$; as an example, N-benzyloxycarbonyltetramethylguanidine is mentioned.

Ionic salts of α-ammonium, α-iminium or α-amidinium ketones or alkenes, which liberate the corresponding tertiary amine bases on irradiation, are described, for example, in WO 98/38195 and WO 00/10964. WO 98/32756 discloses α-amino ketones from which amidine bases can be liberated on irradiation; corresponding α-amino alkenes are disclosed in WO 98/41524. The liberation of the base in this case takes place by way of an intramolecular γ-hydrogen elimination reaction, which is made possible by the special position of the double bond in the α-amino alkenes. The strong bases generated from the photolatent amines in accordance with WO 98/32756 or WO 98/41524 are suitable, for example, for catalysing reactions such as Michael addition. WO 03/033500 describes the synthesis of photoactivable 1,3-diamine bases and the use thereof for curing of coating systems.

There nevertheless continues to be a need for strong, photoactivable amine bases which efficiently liberate amidine bases on irradiation with UV light or visible light and which in base-curable formulations in the absence of light produce one-pot systems whose stability on storage is high.

It has now surprisingly been found that some of those photoactivable 1,3-diamine bases having some specific substituents show unexpected improved stability and higher reactivity after UV- or light-exposure in different coating systems the curing of which is catalyzed by bases, in particular those involving isocyanate groups at one stage of the cure process.

Subject of the invention therefore are photolatent base compounds of the formula (I), (II) and (III)

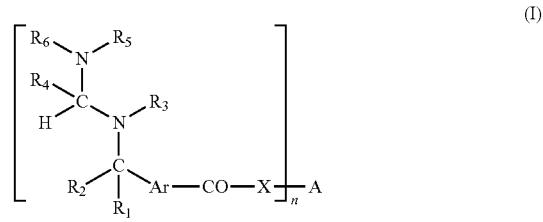

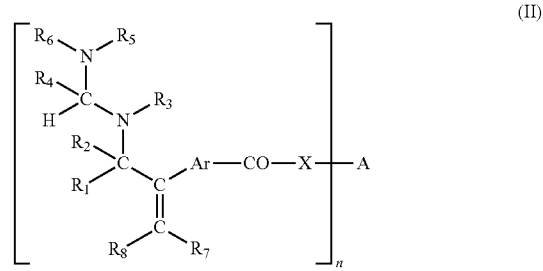

-continued

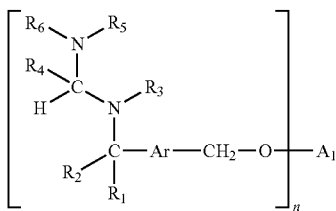
(III)

wherein

Ar is phenylene, biphenylene, naphthylene, anthrylene or anthraquinonylene all of which are unsubstituted or are substituted by one ore more $C_1$-$C_4$-alkyl, $C_2$-$C_4$-alkenyl, CN, $OR_{11}$, $SR_{11}$, $CH_2OR_{11}$, $COOR_{12}$, $CONR_{12}R_{13}$ or halogen;

$R_1$, $R_2$, $R_7$ and $R_8$ independently of one another other are hydrogen or $C_1$-$C_6$-alkyl;

$R_3$ and $R_5$ together form a $C_2$-$C_6$-alkylene bridge which is unsubstituted or substituted by one ore more $C_1$-$C_4$-alkyl;

$R_4$ and $R_6$ together form a $C_2$-$C_6$-alkylene bridge which is unsubstituted or substituted by one ore more $C_1$-$C_4$-alkyl;

$R_{11}$ is hydrogen, $C_1$-$C_6$-alkyl or phenyl;

$R_{12}$ and $R_{13}$ independently of one another are hydrogen, phenyl, $C_1$-$C_{18}$-alkyl, $C_1$-$C_{18}$-alkyl which is interrupted by one or more O; or $R_{12}$ and $R_{13}$ are

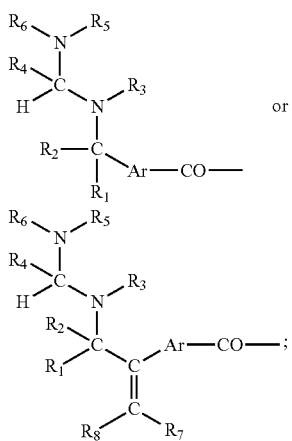

n is 1-10;

X is a direct bond, O, S or $NR_{10}$;

A if n is 1, is hydrogen, uninterrupted $C_1$-$C_{18}$-alkyl or $C_1$-$C_{18}$-alkyl which is interrupted by one or more O or $N(R'_{13})$ and which uninterrupted or interrupted $C_1$-$C_{18}$alkyl is unsubstituted or is substituted by one or more $C_1$-$C_8$-alkyl, $C_1$-$C_6$-hydroxyalkyl, CN, $OR_{11}$, $SR_{11}$, $NR_{12}R_{13}$, $COOR_{12}$, $OCOR_{14}$ or halogen; or A is $C_2$-$C_{18}$-alkenyl or is $C_3$-$C_{18}$alkenyl which is interrupted by one or more O and which $C_2$-$C_{18}$-alkenyl or interrupted $C_3$-$C_{18}$alkenyl is unsubstituted or is substituted by one or more $C_1$-$C_8$-alkyl, $C_1$-$C_6$-hydroxyalkyl, CN, $OR_{11}$, $SR_{11}$, $NR_{12}R_{13}$, $COOR_{12}$, halogen or $C_7$-$C_{15}$-aralkyl; or A if n is 1, is a group

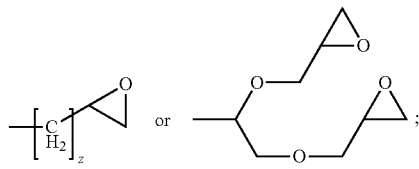

or

A if n is 1, denotes a group

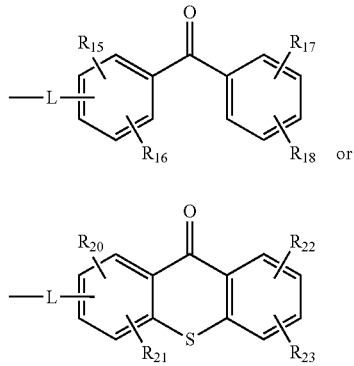

or, if X is O, additionally X-A denotes $X^-$ $Y^+$;

A if n is greater than 1, is an n-valent saturated or unsaturated $C_2$-$C_{50}$hydrocarbon radical, which optionally is interrupted by one or more O, S, $N(R'_{13})$, phenylene, naphthylene,

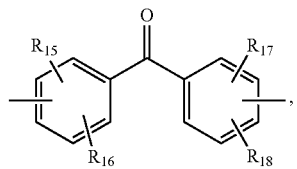

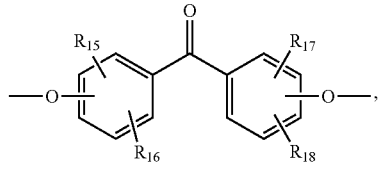

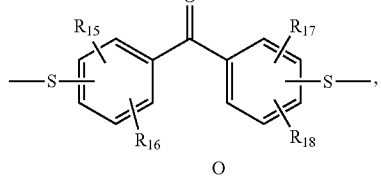

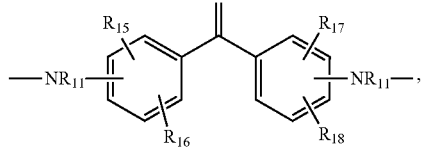

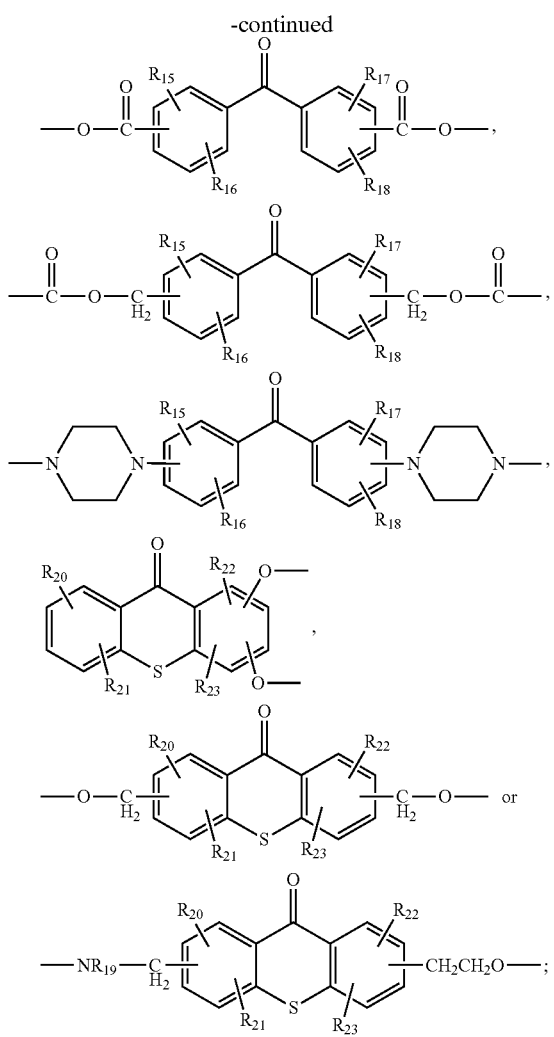

and which uninterrupted or interrupted $C_2$-$C_{18}$alkanoyl is unsubstituted or substituted by one or more $C_1$-$C_4$-alkyl, $C_2$-$C_4$-alkenyl, phenyl, CN, $OR_{11}$, $SR_{11}$, $NR_{12}R_{13}$, $COOR_{12}$ or halogen;

or said uninterrupted or interrupted $C_2$-$C_{18}$alkanoyl is substituted by $C_6$-$C_{10}$-aryl which is unsubstituted or substituted by one ore more $C_1$-$C_4$-alkyl, $C_2$-$C_4$-alkenyl, CN, $OR_{11}$, $SR_{11}$, $NR_{12}R_{13}$ or halogen;

or $A_1$ is $C_3$-$C_{18}$-alkenoyl which is unsubstituted or substituted by one or more $C_1$-$C_4$-alkyl, $C_2$-$C_4$-alkenyl, CN, $OR_{11}$, $SR_{11}$, $NR_{12}R_{13}$, $COOR_{12}$, halogen or by $C_6$-$C_{10}$-aryl which is unsubstituted or substituted by one ore more $C_1$-$C_4$-alkyl, $C_2$-$C_4$-alkenyl, CN, $OR_{11}$, $SR_{11}$, $NR_{12}R_{13}$ or halogen;

$C_2$-$C_{18}$-alkylaminocarbonyl, which is unsubstituted or substituted by one or more $C_1$-$C_4$-alkyl, $C_2$-$C_4$-alkenyl, CN, $OR_{11}$, $SR_{11}$, $NR_{12}R_{13}$, $COOR_{12}$ or halogen;

$C_6$-$C_{20}$arylaminocarbonyl, which is unsubstituted or substituted by one or more $C_1$-$C_4$-alkyl, $C_2$-$C_4$-alkenyl, $OR_{11}$, $NR_{12}R_{13}$ or halogen;

$C_7$-$C_{20}$-arylalkylaminocarbonyl which is unsubstituted or substituted by one or more $C_1$-$C_4$alkyl, $C_2$-$C_4$-alkenyl, $OR_{11}$, $NR_{12}R_{13}$ or halogen;

$C_7$-$C_{15}$-aroyl or $C_5$-$C_{15}$-heteroaroyl, both of which are unsubstituted or substituted by one or more $C_1$-$C_4$-alkyl, $C_2$-$C_4$-alkenyl, CN, $OR_{11}$, $SR_{11}$, $NR_{12}R_{13}$, or halogen; or $A_1$ if n is 1, denotes a group

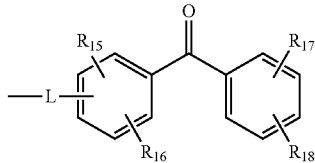

(BP)

or

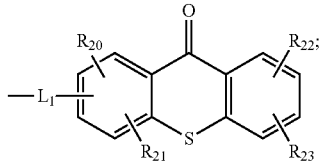

(TX)

$A_1$, if n is greater than 1, a n-valent $C_2$-$C_{30}$alkanoyl which optionally is interrupted by one or more O and which uninterrupted or interrupted $C_2$-$C_{30}$alkanoyl is unsubstituted or is substituted by one or more $C_1$-$C_4$alkyl, $C_2$-$C_4$alkenyl, CN, $OR_{11}$, $SR_{11}$, $NR_{12}R_{13}$, $COOR_{12}$ or halogen;

a n-valent $C_8$-$C_{20}$aroyl or $C_6$-$C_{20}$heteroaroyl, both of which are unsubstituted or substituted by one or more $C_1$-$C_4$-alkyl, $C_2$-$C_4$-alkenyl, CN, $OR_{11}$, $SR_{11}$, $NR_{12}R_{13}$, $COOR_{12}$ or halogen;

a n-valent $C_{10}$-$C_{20}$-aralkanoyl, which is unsubstituted or substituted by one or more $C_1$-$C_4$-alkyl, $C_2$-$C_4$-alkenyl, CN, $OR_{11}$, $SR_{11}$, $NR_{12}R_{13}$, $COOR_{12}$ or halogen; or is a n-valent $C_1$-$C_{30}$-alkylaminocarbonyl, which is unsubstituted or substituted by one or more $C_1$-$C_4$-alkyl, $C_2$-$C_4$-alkenyl, CN, $OR_{11}$, $SR_{11}$, $NR_{12}R_{13}$, $COOR_{12}$ or halogen, wherein said unsubstituted or substituted n-valent $C_1$-$C_{30}$-alkylaminocarbonyl optionally consists of several monovalent $C_1$-$C_{30}$-alkylaminocarbonyl groups which are linked via dimers or trimers of isocyanates or derivatives thereof; or is and which uninterrupted or interrupted n-valent saturated or unsaturated $C_2$-$C_{50}$hydrocarbon radical is unsubstituted or is substituted by one or more $C_1$-$C_8$-alkyl, $C_1$-$C_6$-hydroxyalkyl, CN, $OR_{11}$, $SR_{11}$, $NR_{12}R_{13}$, $COOR_{12}$ or halogen;

or A, if X is $NR_{10}$, is a n-valent polyalkylene-imine; wherein the n-valent polyalkylene-imine is uninterrupted or interrupted by one or more (CO), (CO)O or double bonds and wherein the uninterrupted n-valent polyalkylene-imine is unsubstituted or substituted by

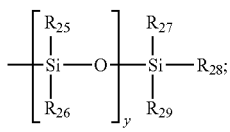

or, if X is O, additionally one or more X-A denote $X^-{}_n\, Y^{n+}$ or $X^-{}_n\, nY^+$;

y is an integer from 1-20;

z is an integer from 1-8;

$R'_{13}$ has one of the meanings as given for $R_{12}$ and $R_{13}$ or is a group (TX);

$R_{10}$ has one of the meanings as given for A, if n is 1;

$A_1$, if n is 1, is hydrogen, $C_1$-$C_{18}$alkanoyl, $C_2$-$C_{18}$-alkanoyl which is interrupted by one or more O and/or CO a n-valent $C_6$-$C_{20}$ arylaminocarbonyl, which is unsubstituted or substituted by one or more $C_1$-$C_4$-alkyl, $C_2$-$C_4$-alkenyl, CN, $OR_{11}$, $SR_{11}$, $NR_{12}R_{13}$, $COOR_{12}$ or halogen; or $A_1$ if n is greater than 1, denotes a group

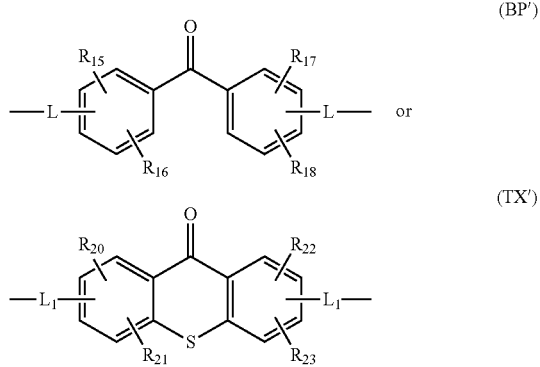

L is a direct bond; unsubstituted $C_1$-$C_{20}$alkylene, $C_1$-$C_{20}$alkylene which is substituted by phenyl or one or more OH; $C_1$-$C_{20}$alkylene which is interrupted by one or more O, S, O(CO), (CO)O;

or is $C_1$-$C_{20}$alkylene-O—(CO), $C_1$-$C_{20}$alkylene-N($R_{19}$)(CO), $C_1$-$C_{20}$alkylene-S, $C_1$-$C_{20}$alkylene-O, $C_1$-$C_{20}$alkylene-(NR$_{19}$) or $C_1$-$C_{20}$alkylene-(CO)—N($R_{19}$), where in the groups $C_1$-$C_{20}$alkylene-O—(CO), $C_1$-$C_{20}$alkylene-N($R_{19}$)(CO), $C_1$-$C_{20}$alkylene-S, $C_1$-$C_{20}$alkylene-O, $C_1$-$C_{20}$alkylene-(NR$_{19}$) and $C_1$-$C_{20}$alkylene-(CO)—N($R_{19}$), the linkage to the benzophenone group is intended to be via the heteroatom N, S or O or via the CO group; or L is (CO)-Q;

Q is a direct bond, $C_1$-$C_8$alkylene or $C_1$-$C_8$alkylene which is interrupted by one or more O;

$L_1$ is direct bond, CO; unsubstituted $C_1$-$C_{20}$alkylene, $C_1$-$C_{20}$alkylene which is substituted by phenyl or one or more OH; $C_1$-$C_{20}$alkylene which is interrupted by one or more O, S, or $NR_{24}$; $C_1$-$C_{20}$alkylene which is interrupted by one or more O, S, or $NR_{24}$ and is substituted by OH;

or is unsubstituted $C_1$-$C_{20}$alkylene-O—(CO) or $C_1$-$C_{20}$alkylene-O—(CO) which is substituted by OH, or is $C_1$-$C_{20}$alkylene-O—(CO) wherein the alkylene is interrupted by one or more O; $C_1$-$C_{20}$alkylene-N($R_{19}$)(CO), $C_1$-$C_{20}$alkylene-S, $C_1$-$C_{20}$alkylene-O, $C_1$-$C_{20}$alkylene-(NR$_{19}$) or $C_1$-$C_{20}$alkylene-(CO)—N($R_{19}$), where in the groups $C_1$-$C_{20}$alkylene-O—(CO) or $C_1$-$C_{20}$alkylene-O—(CO) which is substituted by OH, or is $C_1$-$C_{20}$alkylene-O—(CO) wherein the alkylene is interrupted by one or more O; $C_1$-$C_{20}$alkylene-N($R_{19}$)(CO), $C_1$-$C_{20}$alkylene-S, $C_1$-$C_{20}$alkylene-O, $C_1$-$C_{20}$alkylene-(NR$_{19}$) or $C_1$-$C_{20}$alkylene-(CO)—N($R_{19}$), the linkage to the thioxanthone group is intended to be via the heteroatom N, S or O or via the CO group; or $L_1$ is (CO)—$C_1$-$C_{20}$alkylene-O, where the linkage to the thioxanthone group is intended to be via the O atom; or $L_1$ is (CO)-Q;

Y is an n-valent cationic counter ion;

$R_{14}$ is —CH=CH$_2$ or —C(CH$_3$)=CH$_2$;

$R_{15}$, $R_{16}$, $R_{17}$ and $R_{18}$ independently of one another are hydrogen, halogen, $C_1$-$C_{12}$alkyl, $OR_{11}$, $SR_{11}$, $NR_{12}R_{13}$ or (CO)$OR_{11}$;

$R_{19}$ is hydrogen or $C_1$-$C_6$alkyl;

$R_{20}$, $R_{21}$, $R_{22}$ and $R_{23}$ independently of one another have one of the meanings as defined for $R_{15}$, $R_{16}$, $R_{17}$ and $R_{18}$;

$R_{24}$ is hydrogen, $C_1$-$C_{10}$alkyl or $C_1$-$C_{10}$alkyl which is substituted by OH; and $R_{25}$, $R_{26}$, $R_{27}$, $R_{28}$ and $R_{29}$ independently of one another are $C_1$-$C_4$alkyl.

The stability and reactivity after light activation of the novel compounds of the formula (I), (II) and (III) are improved in the presence of the specific substituents compared to analogous derivatives without these substituents.

Furthermore, the ester or alcohol groups can be easily reacted with other functonalized derivatives, such as for example epoxy alcohols, perfluorinated alcohols, tris (alkoxy)silyl-alcohols, ω-acryloyl-alcohols, fatty acids or caprolactone, to give derivatives with tailor-made properties, such as low volatility, high hydrophobicity, or carrying new functional groups suitable for further transformations.

Moreover, the ester or alcohol groups allow an easy reaction with multifunctional or polymeric alcohols, amines, esters, isocyanates or other functionalities capable of reacting with such functional groups to give multifunctional photolatent amines with low volatility and migration. These compounds of the present invention for example make it possible to produce what are termed one-pot systems, with oligomers or monomers that can undergo base-catalyzed crosslinking reactions, which possess an extraordinarily high storage stability. Only exposure to light triggers reactions catalysed by a base, e.g. organic addition and condensation reactions, for example, a polymerization or a crosslinking by way of addition or condensation reactions. The polymerizable or crosslinkable systems can be formulated in completely or substantially solvent-free form, since the compounds can be dissolved in the monomers or oligomers without affecting them. The active catalyst for triggering the crosslinking reaction is not produced until after exposure to light. These systems containing oligomers or monomers that can be crosslinked by base-catalyzed reactions can be used for a large number of purposes, such as, for example, for paint systems, coatings, moulding compounds, photolithographic imaging systems, adhesives, hot melts, formation of foams, flexo plates, inks etc.

$C_1$-$C_{18}$-alkyl is linear or branched and is, for example, $C_1$-$C_{14}$—, $C_1$-$C_{12}$-, $C_1$-$C_8$-, $C_1$-$C_6$- or $C_1$-$C_4$alkyl. Examples are methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl, dodecyl, tetradecyl, pentadecyl, hexadecyl and octadecyl. $C_1$-$C_6$alkyl and $C_1$-$C_4$alkyl have the same meanings as given above for $C_1$-$C_{18}$alkyl up to the corresponding number of C-atoms $C_1$-$C_6$-hydroxyalkyl for example is $C_2$-$C_6$-, $C_2$-$C_4$- or $C_1$-$C_4$alkyl as described above, however mono- or polysubstituted by OH. For example 1 to 6, e.g. 1 to 4, or one or two OH-substituents are positioned at the alkyl, which is linear or branched. Examples are hydroxymethyl, hydroxyethyl, dihydroxypropyl, hydroxypropyl, dihydroxyethyl, in particular hydroxyethyl.

$C_1$-$C_{18}$-alkyl which is interrupted by one or more O or N($R_{13}$) is for example interrupted 1-8, 1-7, 1-6, 1-5, 1-4, 1-3 or once or twice by O or N($R_{13}$), or both. In case the groups are interrupted by more than one O, said O-atoms are separated from one another by at least one methylene group, i.e. the O-atoms are non-consecutive. Examples are the following structural units —CH$_2$—O—CH$_3$, —CH$_2$CH$_2$—O—CH$_2$CH$_3$, —[CH$_2$CH$_2$O]$_y$—CH$_3$, with y=1-8, —(CH$_2$CH$_2$O)$_7$CH$_2$CH$_3$, —CH$_2$—CH(CH$_3$)—O—CH$_2$—CH$_2$CH$_3$, or —CH$_2$—CH(CH$_3$)—O—CH$_2$CH$_3$. —CH$_2$—N(R$_{13}$)—CH$_3$, —CH$_2$CH$_2$—N(R$_{13}$)—CH$_2$CH$_3$, —[CH$_2$CH$_2$N(R$_{13}$)]$_y$—CH$_3$, with y=1-8, —(N(R$_{13}$)$_7$CH$_2$CH$_3$, —CH$_2$—CH(CH$_3$)—N(R$_{13}$)—CH$_2$—CH$_2$CH$_3$, or —CH$_2$—CH(CH$_3$)—N(R$_{13}$)—CH$_2$CH$_3$. —CH$_2$—N(R$_{13}$)—CH$_2$CH$_2$—O—H$_2$CH$_2$CH$_3$, etc.

Said C$_1$-C$_{18}$-alkyl which is interrupted by one or more O or N(R$_{13}$) optionally is substituted e.g. by OR$_{11}$, resulting for example in structures like —[CH$_2$CH$_2$O]$_y$CH$_2$CH$_2$OH with y=1-8, etc.

C$_2$-C$_{18}$-alkenyl is mono or polyunsaturated, linear or branched and is for example C$_2$-C$_{12}$-, C$_2$-C$_{16}$—, C$_2$-C$_8$—, C$_2$-C$_6$- or C$_2$-C$_4$alkenyl. Examples are allyl, methallyl, vinyl, 1,1-dimethylallyl, 1-butenyl, 3-butenyl, 2-butenyl, 1,3-pentadienyl, 5-hexenyl or 7-octenyl, especially allyl or vinyl.

C$_3$-C$_{18}$alkenyl which is interrupted by one or more O, is for example interrupted 1-8, 1-7, 1-6, 1-5, 1-4, 1-3 or once or twice by O. The alkenyl is defined abover and is mono or polyunsaturated and linear or branched. In case the groups are interrupted by more than one O, said O-atoms are separated from one another by at least one methylene group or double bond, i.e. the O-atoms are non-consecutive, for example —CH=CH—O—CH$_2$CH$_3$, —[CH$_2$CH$_2$O]—CH$_3$, with y=1-8, —(CH$_2$CH$_2$O)$_7$CH$_2$CH$_3$, —CH=C(CH$_3$)—O—CH$_2$—CH$_2$CH$_3$, or —CH=CH(CH$_3$)—O—CH=CH$_2$, etc.

C$_2$-C$_6$-alkylene is linear or branched, for example methylene, ethylene, propylene, 1-methylethylene 1,1-dimethylethylene, 1,1-dimethylpropylene, butylene, 1-methylpropylene, 1-methylbutylene, 2-methyl-propylene, pentylene or hexylene.

C$_2$-C$_{18}$-alkylene which is interrupted by one or more O or N(R$_{13}$) is for example —(CH$_2$CH$_2$O)$_y$—CH$_2$CH$_2$— with y=1-8, —(CH$_2$CH$_2$CH$_2$O)$_z$—CH$_2$CH$_2$CH$_2$— with z=1 or 2, —(CH$_2$CH$_2$NR$_{13}$)$_y$—CH$_2$CH$_2$— with y=1-8, —[CH$_2$CH$_2$N(CH$_2$CH$_2$NR$_{13}$)$_y$CH$_2$CH$_2$NH$_2$]$_y$—(CH$_2$CH$_2$NR$_{13}$)$_b$—CH$_2$CH$_2$—, naphthoyl ring. The same applies for the different positions of the anthryl and phenanthryl rings.

Phenylene, biphenylene, naphthylene, anthrylene or anthraquinonylene maybe linked to the radicals via different positions in the rings, examples are 1,4-phenylene, 1,3-phenylene, 1,2-phenylene, 1,2-naphthylene, 2, 3-naphthylene etc.

C$_1$-C$_{18}$-alkanoyl, similar to C$_1$-C$_{18}$alkylcarbonyl, is linear or branched and is, for example, C$_1$-C$_{16}$-, C$_1$-C$_{14}$-, C$_1$-C$_{12}$-, C$_1$-C$_8$-, C$_1$-C$_6$- or C$_1$-C$_4$alkanoyl or C$_2$-C$_{12}$- or C$_2$-C$_8$alkanoyl. Examples are formyl, acetyl, propionyl, butanoyl, isobutanoyl, pentanoyl, hexanoyl, heptanoyl or, octanoyl, preferably acetyl.

C$_2$-C$_{18}$-alkanoyl which is interrupted by one or more O and/or CO, is for example interrupted 1-12 times, e.g. 1-6, 1-4, 1-3, one or twice. Interrupting O and CO may be parted by several or one methylene, however also may be consecutive and thus forming interrupting groups (CO)O or O(CO).

C$_3$-C$_6$alkenoyl is mono or polyunsaturated and is for example C$_2$-C$_5$-alkene as defined above, end-capped by a CO (="oyl"). Examples are propenoyl, 2-methyl-propenoyl, butenoyl, pentenoyl, 1,3-pentadienoyl, 5-hexenoyl.

C$_1$-C$_{30}$-alkylaminocarbonyl denotes (C$_1$-C$_{30}$-alkyl)NH(CO)—, e.g. (C$_1$-C$_8$-alkyl)NH(CO)— or (C$_1$-C$_4$-alkyl)NH(CO)—, wherein the alkyl is defined as above up to the corresponding number of C-atoms.

C$_1$-C$_{30}$-alkylaminocarbonyl which consists of several monovalent C$_1$-C$_{30}$-alkylaminocarbonyl which are linked via dimers or trimers of isocyanates or derivatives thereof are for example linked via radicals like

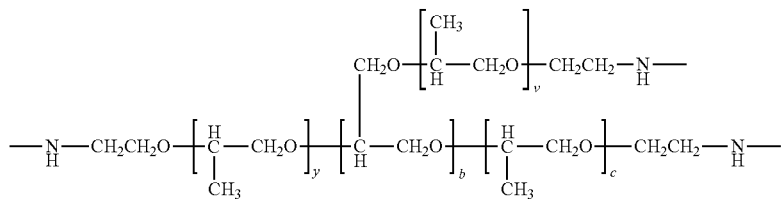

with $y$ = 1-8, $b$ = 0-7, $c$ = 0-7, $v$ = 0-7; etc.

Examples of C$_2$-C$_6$alkylene bridges are ethylene, propylene, butylene, pentylene or hexylene, preferably propylene and pentylene, in particular propylene. These bridges are, for example, unsubstituted or substituted by one or more C$_1$-C$_4$alkyl. C$_1$-C$_4$alkyl is as described above up to the corresponding number of carbon atoms.

C$_7$-C$_{15}$-aralkyl denotes a C$_1$-C$_9$-alkyl substituted by an aromatic radical, such as phenyl, naphthyl, anthryl or phenanthryl. Examples are phenyl-C$_1$-C$_9$-alkyl, naphthyl-C$_1$-C$_5$-alkyl, anthryl-methyl, phenanthryl-methyl. The alkyl groups are linear or branched and have the meaning as given above. Specific examples are benzyl, phenylethyl, α-methylbenzyl, phenylpentyl, phenylhexyl or α,α-dimethylbenzyl, in particular benzyl and naphthylmethyl, especially benzyl. The alkyl radical may be present in different positions of the aryl ring, e.g. in 1- or in 2-position of the

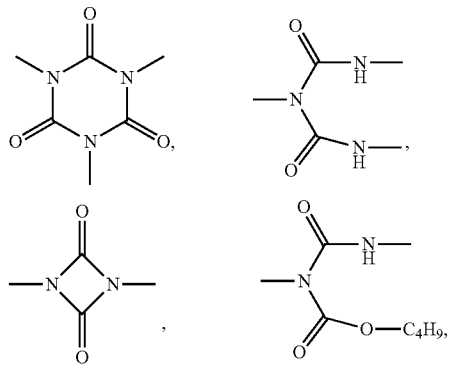

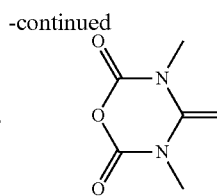

etc., or similar groups, (precursors of which are given for example also in the list of starting materials below) resulting for example in groups $A_1$ as follows: (trivalent):

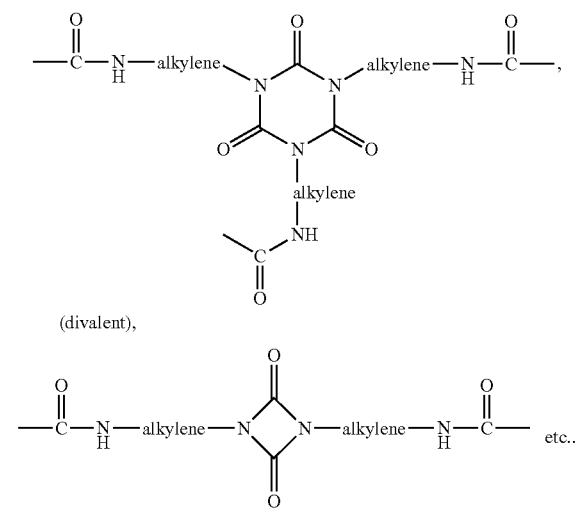

$C_6$-$C_{20}$-arylaminocarbonyl denotes $(C_6$-$C_{20}$aryl$)$NH(CO)—, e.g. $(C_6$-$C_{10}$aryl$)$NH(CO)—, wherein $C_6$-$C_{20}$aryl is for example phenyl, naphthyl, anthryl or phenanthryl, all of which are unsubstituted or substituted. Examples of substituents are $C_1$-$C_4$alkyl, e.g. methyl and $C_1$-$C_4$alkoxy, e.g. methoxy.

$C_7$-$C_{14}$-arylalkylaminocarbonyl denotes $(C_7$-$C_{14}$-aralkyl$)$NH(CO)—, e.g. $(C_7$-$C_{10}$aralkyl$)$NH(CO), wherein the aralkyl is defined as above.

$C_7$-$C_{15}$-aroyl is $C_6$-$C_{14}$-aryl-CO. Examples of suitable $C_6$-$C_{14}$aryl are phenyl, naphthyl, anthryl and phenanthryl. In the naphthoyl, anthrenoyl and phenanthrenoyl the CO may be linked in different positions of the corresponding ring system, e.g. in the 1- or 2-position of the naphthyl ring. Corresponding facts apply for anthrenoyl and phenanthrenoyl, e.g. 1-anthryl, 2-anthryl, 9-anthryl.

$C_5$-$C_{15}$-heteroaroyl is $C_4$-$C_{14}$-heteroaryl-CO. Examples of suitable $C_4$-$C_{14}$-heteroaryl contain one or more, e.g. 1 or 2, especially 1 heteroatom(s). Examples of suitable heteroatoms are N, P, O and S, e.g. N, O or S, preferably N or O. Examples are thienyl, benzo[b]thienyl, naphtho[2,3-b]thienyl, thianthrenyl, dibenzofuryl, chromenyl, xanthenyl, phenoxathiinyl, pyrrolyl, imidazolyl, pyrazolyl, pyrazinyl, pyrimidinyl, pyridazinyl, indolizinyl, isoindolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, carbazolyl, β-carbolinyl, phenanthridinyl, acridinyl, perimidinyl, phenanthrolinyl, phenazinyl, isothiazolyl, phenothiazinyl, isoxazolyl, furazanyl, fluorenyl, phenoxazinyl, anthraquinone-2-yl (=9,10-dioxo-9,10-dihydroanthracen-2-yl), 2-xanthenyl, 8-methyl-2-xanthenyl, 3-xanthenyl, 2-phenoxyathiinyl, 2,7-phenoxathiinyl, etc.

A n-valent radical is for example 2-10, 2-8, 2-6, 2-5, 2-4, three or two-valent.

Examples of saturated or unsaturated $C_2$-$C_{50}$hydrocarbon radicals are $C_1$-$C_{50}$alkylene, which is linear or branched, such as for example methylene, ethylene, propylene, 1-methylethylene 1,1-dimethylethylene, butylene, 1-methylpropylene, 2-methyl-propylene, pentylene, hexylene, heptylene, octylene, nonylene, decylene, dodecylene, tetradecylene, hexadecylene, octadecylene etc.;

$C_2$-$C_{50}$alkenylene, which is mono- or polyunsaturated, linear or branched such as, for example, ethenylene, 1-propenylene, 1-butenylene, 3-butenylene, 2-butenylene, 1,3-pentadienylene, 5-hexenylene, 7-octenylene, etc.;

$C_3$-$C_{50}$Cycloalkylene such as, for example, cyclopropylene, cyclopentylene, cyclohexylene, cyclooctylene, cyclododecylene, bicyclodecylene, etc. as well as linear or branched alkylene-s comprising rings, for example, structural units such as

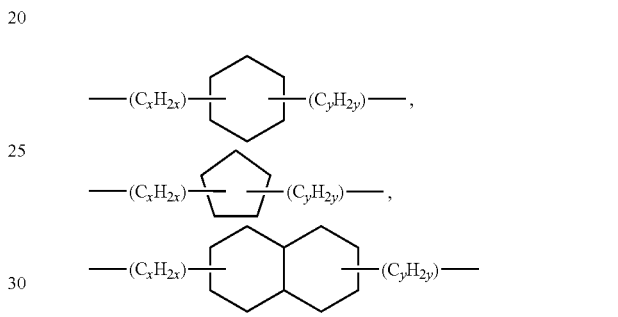

etc., in which x and y denote integers from 0 to a number summing up the number of C-atoms of the group to 50; further, bridged or fused ring systems are meant to be covered, as, for example

etc.; or $C_3$-$C_{50}$Cycloalkenylene.

Further specific examples are to be derived from the specific starting materials which are listed below in the description of the preparation of the compounds according to the invention.

A trivalent $C_2$-$C_{50}$hydrocarbon radical is for example is $C_2$-$C_{50}$alkanetriyl, wherein the alkane moiety is linear or branched, etc.; or a corresponding radical comprising alkene, cycloalkyl or cycloalkenyl moieties as described above.

Similarly tetra- or higher valent groups are arranged.

Specific examples are to be derived from the specific starting materials which are listed below in the description of the preparation of the compounds according to the invention.

A n-valent saturated or unsaturated $C_2$-$C_{50}$hydrocarbon radical which is interrupted by one or more O, $N(R_{13})$, phenylene or naphthylene is a radical as described before, interrupted for example by 1-25, 1-20, 1-15, 1-10, 1-8, 1-6, 1-4, three, two or one O, $N(R_{13})$, phenylene or naphthylene. The interrupting atoms or groups preferably are non-successive. The interrupting groups —O— or —$N(R_{13})$— are preferentially separated by two or three methylene groups, especially preferred by two methylene groups.

Specific examples are to be derived from the specific starting materials which are listed below in the description of the preparation of the compounds according to the invention.

Further examples for n-valent saturated or unsaturated $C_2$-$C_{50}$hydrocarbon radical are phenylene, naphthylene, biphenylene,

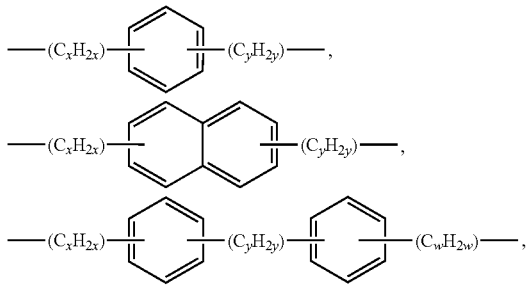

in which x, y and w denote integers from 0 to a number summing up the number of C-atoms of the group to 50.

A n-valent $C_2$-$C_{30}$alkanoyl denotes a corresponding alkylene with n "oyl" groups, capable to be linked to the

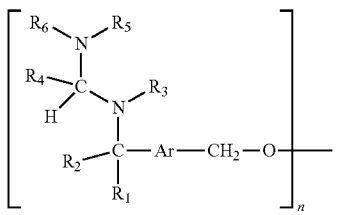

in formula III. The alkylene part is linear or branched and corresponds to definitions as given above.

Specific examples are to be derived from the specific starting materials which are listed below in the description of the preparation of the compounds according to the invention.

A n-valent $C_2$-$C_{30}$alkenoyl denotes a corresponding alkenylene with n "oyl" groups, capable to be linked to the

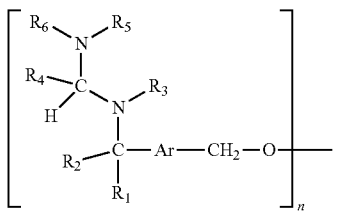

in formula III. The alkenylene part is linear or branched and corresponds to definitions as given above.

n-valent $C_8$-$C_{20}$aroyl or $C_6$-$C_{20}$heteroaroyl correspond to similar groups as described above for the corresponding mono-valent radicals, however replacing one or more (i.e. "n") saturation of said radicals by —CO—.

Examples of divalent $C_8$-$C_{20}$aroyl or $C_6$-$C_{20}$heteroaroyl are CO-phenylene-CO, CO-stilbenylene-CO, CO-biphenylene-CO, o-, m- and p-CO-terphenylene-CO, CO-naphthylene-CO, CO-binaphthylene-CO, CO-anthracenylene-CO, CO-phenanthrylene-CO, CO-pyrenylene-CO, CO-furanylene-CO, CO-thiophenylene-CO, CO-pyridinylene-CO, CO-quinolinylene-CO or CO-isoquinolinylene-CO. etc.

Similarly tretra- or higher valent groups are arranged.

n-valent $C_{10}$-$C_{20}$-aralkanoyl, n-valent $C_1$-$C_{30}$-alkylaminocarbonyl and n-valent $C_6$-$C_{20}$arylaminocarbonyl correspond to similar groups as described above for the corresponding mono-valent radicals, however replacing one or more (="n–1") saturations of said radicals by —CO—.

Specific examples are to be derived from the specific starting materials which are listed below in the description of the preparation of the compounds according to the invention. See for example also the dimer or trimer linkers derived from isocyanates or derivatives thereof as named above for linking several mono-valent alkylaminocarbonyl groups.

In the context of the present invention n-valent $C_2$-$C_{30}$alkanoyl, $C_8$-$C_{20}$aroyl, $C_6$-$C_{20}$heteroaroyl, $C_{10}$-$C_{20}$-aralkanoyl, $C_1$-$C_{30}$-alkylaminocarbonyl and $C_6$-$C_{20}$ arylaminocarbonyl are meant to be linked to the corresponding radical in the molecule via the "oyl" group, that is, said radicals are "n-oyl-valent".

Y as an "n-valent cationic counter ion" is for example a cation with one, two, three or four positive charges. If n in the compounds of the formula I or II is higher than 4, more than one counter ions Y may be present in the molecule. However, the same applies for compounds of the formula I and II with n=2-4.

If X is O in a compound of the formula I or II and n is greater than 1, one or more of the groups X-A may denote $X_n^-$ $Y^{n+}$ or $X_n^-$ n $Y^+$. This means, that not all of the groups linking the photolatent base moieties of the molecule have to be in the salt form. In one molecule linkage via salt formation as well as usual covalent bonds is possible. The provision for X to be O is only given for the groups with a salt formation, all other groups linking to a photolatent base moiety also can have one of the other definitions of X as given above. For example molecules like

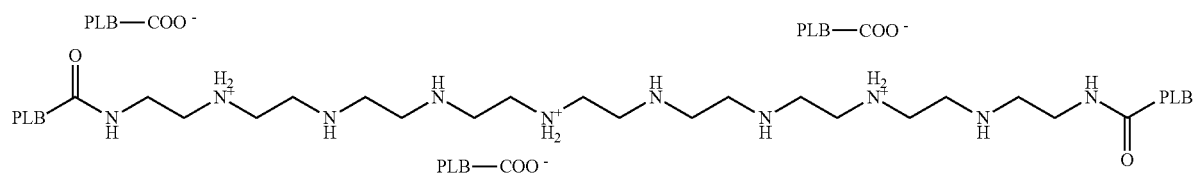

wherein PLB is

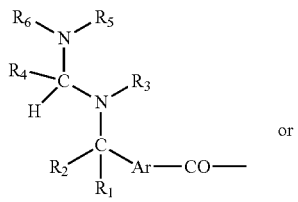

or

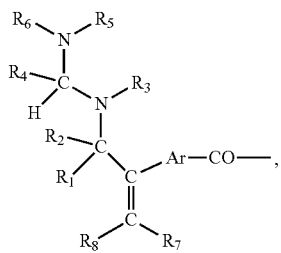

wherein $R_1$-$R_8$ and Ar are as defined above, are formed.

Accordingly, Y is for example a metal cation in the oxidation state +1, such as an alkali metal ion, $Li^+$, $Na^+$, $K^+$, $Cs^+$, or an "onium" cation, such as ammonium-, phosphonium-, iodonium- or sulfonium cation;

or Y is a metal cation in the oxidation state +2, such as an earth alkali ion, $Mg^{2+}$, $Ca^{2+}$ or $Zn^{2+}$, $Cu^{2+}$, e.g. $Mg^{2+}$, $Ca^{2+}$, $Zn^{2+}$, preferably $Mg^{2+}$ or $Ca^{2+}$;

or Y is a metal cation in the oxidation state +3, such as $Al^{3+}$, or a metal cation in the oxidation state +4, such as $Sn^{4+}$ or $Ti^{4+}$.

Examples for onium cations are ammonium, tetra-alkylammonium, tri-alkyl-aryl-ammonium, di-alkyl-di-aryl-ammonium, tri-aryl-alkyl-ammonium, tetra-aryl-ammonium, tetra-alkylphosphonium, tri-alkyl-aryl-phosphonium, di-alkyl-di-aryl-phosphonium, tri-aryl-alkyl-phosphonium, tetra-aryl-phosphonium.

E.g. $N^+ R_{22}R_{23}R_{24}R_{25}$ or $P^+R_{22}R_{23}R_{24}R_{25}$, wherein $R_{22}$, $R_{23}$, $R_{24}$, $R_{25}$ independently of one another are hydrogen, phenyl, phenyl substituted by OH or $C_1$-$C_4$ alkyl or are $C_1$-$C_{20}$alkyl which optionally is substituted by OH, $C_1$-$C_4$alkoxy, $NR_{26}R_{27}$, benzoyl, phenyl or $Si(OH)_r(OC_1$-$C_4$alkyl$)_s$;

or two of $R_{22}$, $R_{23}$, $R_{24}$ or $R_{25}$ together form a 5- or 6-membered saturated or unsaturated ring, which optionally is fused onto other ring systems and which 5- or 6-membered saturated or unsaturated ring optionally includes additional heteroatoms, for example S, $NR_{15}$ or O;

$R_{26}$ and $R_{27}$ independently of one another are hydrogen or $C_1$-$C_4$alkyl which optionally is substituted by OH; and r and s independently of one another are 0-3, provided, that the sum of r+s is 3.

Also suitable are more-valent ammonium-cations, e.g. such based on polyethylene imine structures.

Examples of appropriate ammonium compounds are tetramethylammonium, tetrae-thylammonium, tetrapropylammonium, tetrabutylammonium, benzyltrimethylammonium, benzyltriethylammonium, benzyltripropylammonium and benzyltributylammonium. Tris($C_1$-$C_8$alkyl)ammonium ions are also suitable, for example trimethylammonium.

Also suitable as cationic counter ion Y are dye cations. Examples are cations of triarylmethanes, for example malachite green, indolines, thiazines, for example methylene blue, xanthones, thioxanthones, oxazines, acridines, cyanines, rhodamines, phenazines, for example safranin. Also suitable are dyes containing acid groups, for example methyl red, ethyl orange, methyl orange, acid yellow, rosolic acid, phenol red, fluorescein, Rose Bengal, thymol-phthalein monophosphoric acid, auramine 0, cresyl violet, rhodamine B, brilliant green or variamine blue.

Y is preferably $Li^+$, $Na^+$, $K^+$, $Cs^+$, $N^+R_{22}R_{23}R_{24}R_{25}$ or $P^+R_{22}R_{23}R_{24}R_{25}$; e.g. $Li^+$, $Na^+$, $K^+$, $N^+R_{22}R_{23}R_{24}R_{25}$ or $P^+R_{22}R_{23}R_{24}R_{25}$, in particular $Li^+$, $Na^+$, $K^+$ or $N^+R_{22}R_{23}R_{24}R_{25}$.

A, if X is $NR_{10}$ also denotes a n-valent polyalkylene-imine. The alkylene groups in said radical are as defined above, preferably are methylene or ethylene, in particular ethylene, that is A preferably denotes a n-valent polymethylene-imine or polyethylene-imine, in particular poly-ethylene-imine. Examples are

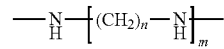

with n=2-6 and m≥1;

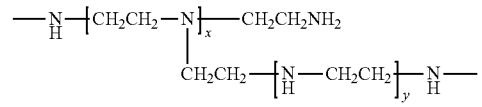

with x and y 1;

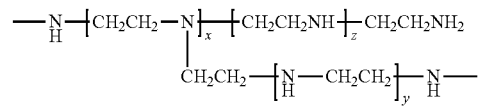

with x, y and z 1;

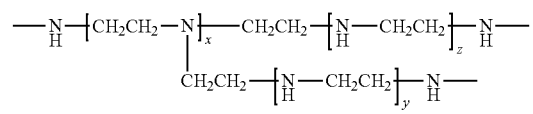

with x, y and z 21, e.g. 6-9.

The n-valent polyalkylene-imine is uninterrupted or interrupted by one or more (CO), (CO)O or double bonds

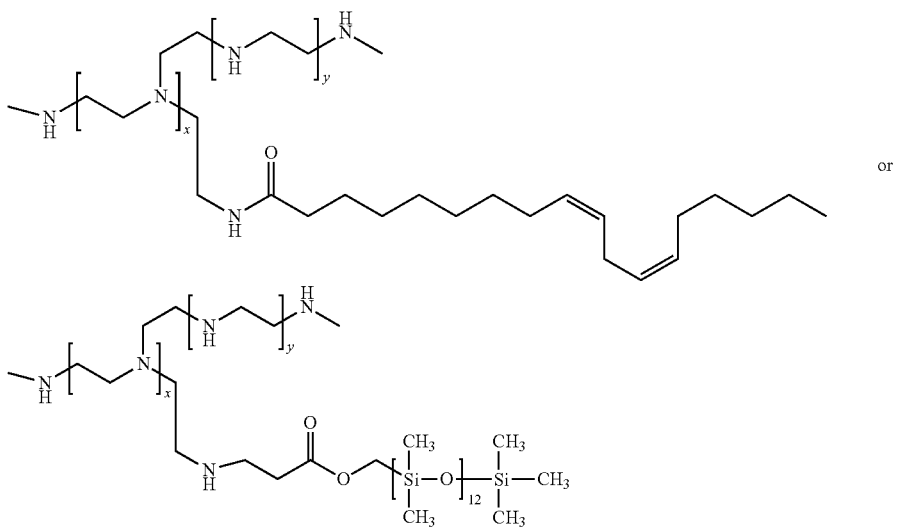

or

And the uninterrupted or interrupted n-valent polyalkylene-imine is unsubstituted or substituted by siloxane groups like

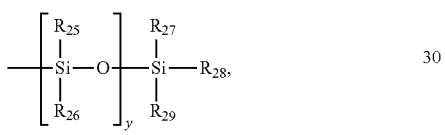

in particular where $R_{25}$ to $R_{29}$ are methyl; for example

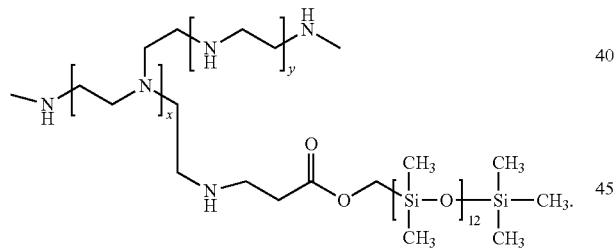

Further specific examples are to be derived from the specific starting materials which are listed below in the description of the preparation of the compounds according to the invention.

If in the compounds of the formula (I), (Ia), (Ib) or (Ic) A is a n-valent saturated or unsaturated $C_2$-$C_{50}$hydrocarbon radical which is substituted by one or more

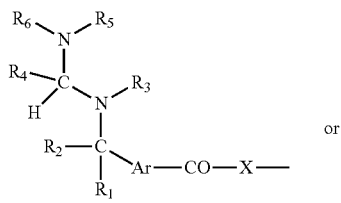

or

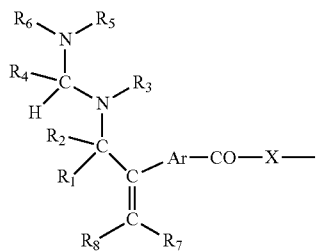

a substituent

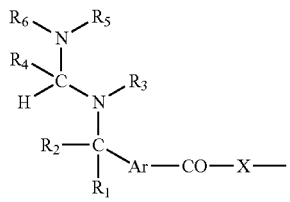

is preferred;

If in the compounds of the formula (II), (IIa), (IIb) or (IIc) A is a n-valent saturated or unsaturated $C_2$-$C_{50}$hydrocarbon radical which is substituted by one or more

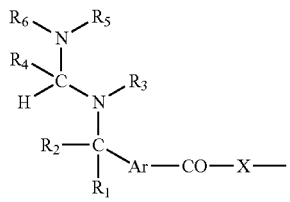

or

-continued

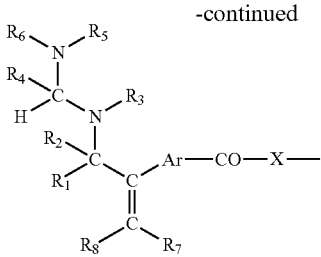

a substituent

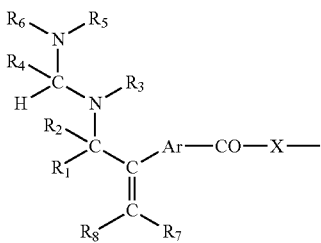

is preferred.

Where a definition refers to one or more substituents, there are for example from 1 to 4, from 1 to 3, 1 or two, preferably one, substituent(s) present.

Halogen is Cl, F, Br or I, especially Cl, F or Br, preferably Cl.

The terms "and/or" or "or/and" in the present context are meant to express that not only one of the defined alternatives (substituents) may be present, but also several of the defined alternatives (substituents) together, namely mixtures of different alternatives (substituents).

The term "at least" is meant to define one or more than one, for example one or two or three, preferably one or two.

The term "optionally substituted" means, that the radical to which it refers is either unsubstituted or substituted.

The term "optionally interrupted" means, that the radical to which it refers is either uninterrupted or interrupted.

Throughout this specification and the claims which follow, unless the context requires otherwise, the word "comprise", or variations such as "comprises" or "comprising", will be understood to imply the inclusion of a stated integer or step or group of integers or steps but not the exclusion of any other integer or step or group of integers or steps.

The term "(meth)acrylate" in the context of the present application is meant to refer to the acrylate as well as to the corresponding methacrylate.

Subject of the invention are compounds of the formula I, II and III as defined above. Emphasis has to be laid on compounds of the formula I and II, in particular interesting are the compounds of the formula I.

X is for example O, S, or $NR_{10}$, in particular O or $NR_{10}$, especially preferred O.

Therefore, photolatent base compounds of the formula (I) or (II), wherein X is O or $NR_{10}$, in particular O, are preferred.

n is for example an integer from 1-10, 2-10, 1-8, 2-8, 1-6, 2-6, 1-5, 2-5, 1-4, 2-4, 1-3, 2 or 1. Preferably n is 1 or 2, in particular 1.

y is for example an integer from 1-20, 1-10, 2-10, 1-8, 2-8, 1-6, 2-6, 1-5, 2-5, 1-4, 2-4, 1-3, 2 or 1.

z is an integer from 1-8; for example 1-6, 2-6, 1-4, 2-4 or 1-2.

Ar is for example phenylene, biphenylene, naphthylene, anthrylene or anthraquinonylene; in particular phenylene, biphenylene or naphthylene, especially phenylene or biphenylene, preferably phenylene. Ar as phenylene is for example 1,3-phenylene or 1,4-phenylene, preferably 1,4-phenylene.

$R_1$ and $R_2$ for example are hydrogen or $C_1$-$C_6$alkyl, preferably hydrogen or $C_1$-$C_4$alkyl, for example $R_1$ is hydrogen and $R_2$ is $C_1$-$C_6$- or $C_1$-$C_4$alkyl. Preferably both, $R_1$ and $R_2$ are hydrogen.

$R_7$ and $R_8$ for example independently of one another other are hydrogen or $C_1$-$C_6$-alkyl, in particular hydrogen or $C_1$-$C_4$alkyl; for example $R_7$ is hydrogen and $R_8$ is $C_1$-$C_6$—, especially $C_1$-$C_4$alkyl. Preferably both, $R_7$ and $R_8$ are hydrogen.

A if n is 1, for example is hydrogen or $C_1$-$C_{18}$-alkyl which optionally is interrupted by one or more O or $N(R_{13})$ and which uninterrupted or interrupted $C_1$-$C_{18}$alkyl is unsubstituted or is substituted by one or more $C_1$-$C_8$-alkyl, $C_1$-$C_6$-hydroxyalkyl, CN, $OR_{11}$, $SR_{11}$, $NR_{12}R_{13}$, $COOR_{12}$ or halogen; in particular is hydrogen, $C_1$-$C_{18}$ alkyl, especially $C_1$-$C_4$alkyl; or is $C_1$-$C_8$-alkyl, in particular $C_1$-$C_8$alkyl which is interrupted by one or more O; and both the uninterrupted and interrupted alkyl group optionally is unsubstituted or is substituted by one or more $OR_{11}$, $NR_{12}R_{13}$ or $COOR_{12}$, especially by $OR_{11}$ or $NR_{12}R_{13}$, in particular by $OR_{11}$.

A if n is greater than 1, as n-valent saturated or unsaturated $C_2$-$C_{50}$hydrocarbon radical, which optionally is interrupted by one or more O, $N(R_{13})$, phenylene or by naphthylene and which uninterrupted or interrupted n-valent saturated or unsaturated $C_2$-$C_{50}$hydrocarbon radical is unsubstituted or is substituted by one or more $C_1$-$C_8$-alkyl, $C_1$-$C_6$-hydroxyalkyl, CN, $OR_{11}$, $SR_{11}$, $NR_{12}R_{13}$, $COOR_{12}$ or halogen preferably is $C_1$-$C_{12}$alkylene, which optionally is interrupted by one or more O, in particular 1 or 2 O and both the uninterrupted and interrupted $C_1$-$C_{12}$alkylene optionally are substituted in particular by $OR_{11}$, $NR_{12}R_{13}$ or $COOR_{12}$, preferably by $OR_{11}$ or $NR_{12}R_{13}$, especially by $OR_{11}$.

$A_1$ preferably is $C_1$-$C_{12}$alkanoyl, in particular $C_1$-$C_{12}$alkanoyl which is optionally substituted by $COOR_{12}$.

With $R_3$ and $R_5$ together forming a $C_2$-$C_6$-alkylene bridge $R_4$ and $R_6$ together forming a $C_2$-$C_6$-alkylene bridge for example the following structures of the formula (Ia), (IIa) and (IIIa) are formed:

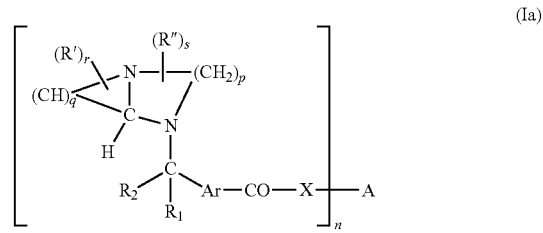
(Ia)

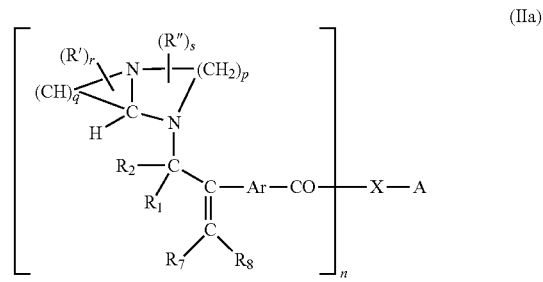
(IIa)

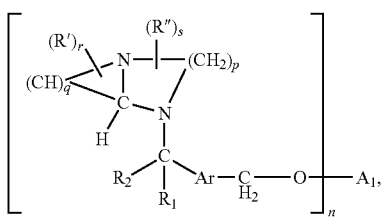
(IIIa)

wherein p and q independently of each other are 2-6, preferably 3-6, e.g. 3 and 5 or 3 and 3; R' and R" independently of each other are $C_1$-$C_4$-alkyl; r and s independently of each other are 0-6, preferably 0-4, e.g. 0, 1 or 2, in particular 0 or 1; and $R_1$, $R_2$, $R_7$, $R_8$, Ar, X, A, $A_1$ and n are defined as above in the compounds of the formula (I), (II) and (III).

Preferably $R_3$ and $R_5$ as well as $R_4$ and $R_6$ together are propylene or $R_3$ and $R_5$ are propylene and $R_4$ and $R_6$ together are pentylene. In particular preferred are compounds wherein both, $R_3$ and $R_5$ as well as $R_4$ and $R_6$, together are propylene.

Thus, in particular preferred are compounds of the formula (Ib), (IIb), (IIIb), (Ic), (IIc) and

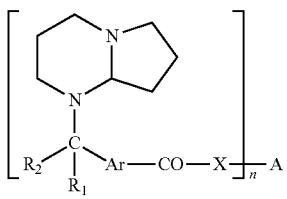
(Ib)

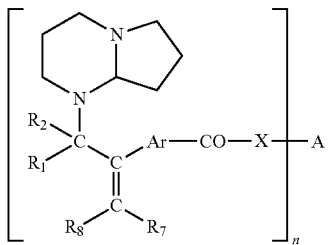
(IIb)

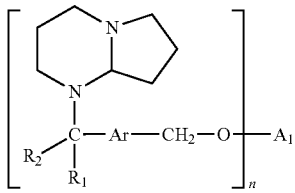
(IIIb)

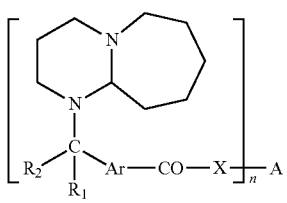
(Ic)

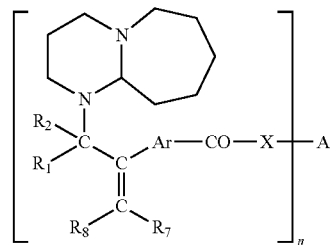
(IIc)

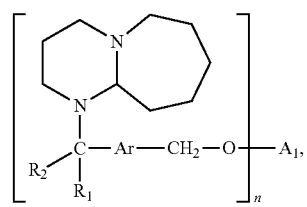
(IIIc)

wherein $R_1$, $R_2$, $R_7$, $R_8$, Ar, X, A, $A_1$ and n are defined as above in the compounds of the formula (I), (II) and (III).

Further interesting are photolatent base compounds of the formula (I) or (III) as described above, wherein Ar is phenylene;
$R_1$, and $R_2$ independently of one another other are hydrogen;
$R_3$ and $R_5$ together form a propylene bridge;
$R_4$ and $R_6$ together form a $C_3$-$C_5$-alkylene bridge;
$R_{11}$ is hydrogen or $C_1$-$C_6$-alkyl;
$R_{12}$ and $R_{13}$ independently of each other are hydrogen or $C_1$-$C_{18}$-alkyl;
n in the compounds of the formula (I) is 1 or 2; and in the compounds of formula III is 1;
X is O, S, $NR_{10}$ or a direct bond;
$R_{10}$ is hydrogen;
A if n is 1, is $C_1$-$C_{18}$-alkyl which is uninterrupted or is interrupted by one or more O and which uninterrupted or interrupted $C_1$-$C_{18}$alkyl is unsubstituted or is substituted by $OR_{11}$, $NR_{12}R_{13}$ or $OCOR_{14}$;
or A is $C_2$-$C_8$-alkenyl;
or A is a group (TX) or (BP);
or, if X is O, additionally X-A denotes $X^- Y^+$;
$L_1$ is $C_1$-$C_8$alkylene-S;
L is $C_1$-$C_8$alkylene-S;
$R_{14}$ is —CH=$CH_2$;
$R_{15}$, $R_{16}$, $R_{17}$ and $R_{18}$ are hydrogen;
$R_{20}$, $R_{21}$, $R_{22}$ and $R_{23}$ are hydrogen;
A if n is greater than 1, as n-valent saturated or unsaturated $C_2$-$C_{50}$hydrocarbon radical is $C_2$-$C_{18}$-alkylene, which optionally is interrupted by one or more O and which uninterrupted or interrupted $C_2$-$C_{18}$-alkylene is unsubstituted or is substituted by $OR_{11}$;
or A if n is greater than 1, is an n-valent polyalkylene imine which is uninterrupted or is interrupted by (CO), (CO)O or a double bond and which uninterrupted or interrupted n-valent polyalkylene imine is unsubstituted or is substituted by

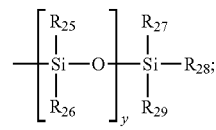

$A_1$, if n is 1, is hydrogen or $C_2$-$C_{18}$-alkanoyl which is unsubstituted or substituted by $COOR_{12}$; $R_{25}$, $R_{26}$, $R_{27}$, $R_{28}$ and $R_{29}$ are methyl;

y is and integer from 1-12; and

Y as an n-valent cationic counter ion, is an alkali metal.

Interesting are photolatent base compounds of the formula (I) or (III) as described above, wherein Ar is phenylene;

$R_1$, and $R_2$ independently of one another other are hydrogen;

$R_3$ and $R_5$ together form a propylene bridge;

$R_4$ and $R_6$ together form a $C_3$-$C_5$-alkylene bridge;

$R_{11}$ is hydrogen or $C_1$-$C_6$-alkyl;

$R_{12}$ is $C_1$-$C_{18}$-alkyl;

n in the compounds of the formula (I) is 1 or 2; and in the compounds of formula III is 1;

X is O;

A if n is 1, is $C_1$-$C_{18}$-alkyl which optionally is interrupted by one or more O and which uninterrupted or interrupted $C_1$-$C_{18}$alkyl is unsubstituted or is substituted by $OR_{11}$;

A if n is 2, as n-valent saturated or unsaturated $C_2$-$C_{50}$hydrocarbon radical is $C_2$-$C_{18}$-alkylene, which optionally is interrupted by one or more O and which uninterrupted or interrupted $C_2$-$C_{18}$-alkylene is unsubstituted or is substituted by $OR_{11}$;

$A_1$, if n is 1, is hydrogen or $C_2$-$C_{18}$-alkanoyl which is unsubstituted or substituted by $COOR_{12}$.

Subject of the invention also are compounds of the formula (I) wherein

Ar, $R_1$, $R_2$, $R_3$, $R_4$, $R_5$, $R_6$, X and A as defined above, provided that, if X is O, A is not hydrogen or $C_{1-18}$alkyl.

Subject of the invention further are compounds of the formula II, wherein Ar, $R_1$, $R_2$, $R_3$, $R_4$, $R_5$, $R_6$, $R_7$, $R_8$, X and A as defined above, provided that, if X is O, A is not hydrogen or $C_{1-18}$alkyl.

The compounds of the invention can be prepared by various processes known to the person skilled in the art.

By way of example, compounds of the formula (I) can be prepared by reacting compounds of the formula (VI)

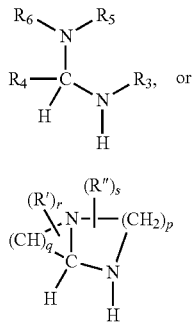

(VI)

(VIa)

in which $R_3$, $R_4$, $R_5$, $R_6$, R', R'', p, q, r and s are as defined above, with a compound of the formula (VII)

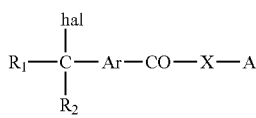

(VII)

in which $R_1$, $R_2$, Ar and X are as defined above, including the preferred definitions, hal is a halogen atom, $OCOR_{20}$ or $OSO_2R_{20}$, and $R_{20}$ is $C_1$-$C_8$alkyl, perfluoroalkyl or aryl which is substituted by one or more $C_1$-$C_4$alkyl or by fluorine. hal is preferably bromine or chlorine.

The reaction of compounds of the formula (VI) or (VIa) with compounds of the formula (VII) can be carried out in a manner known per se. It is advantageous to use a solvent or mixture of solvents, examples being hydrocarbons such as benzene, toluene, xylene, etc., halogenated hydrocarbons, such as methylene chloride, chloroform, carbon tetrachloride, chlorobenzene, etc., alkanols such as methanol, ethanol, ethylene glycol monomethyl ether, etc., and ethers such as diethyl ether, dibutyl ether, tetrahydrofuran, ethylene glycol dimethyl ether, ketones such as acetone or 2-butanone or dimethyl sulfoxide. It is also possible to use mixtures of such solvents.

It is appropriate to add a base to the reaction mixture. Suitable bases are tertiary amines such as, for example, triethylamine, triethanolamine, 2,2,6,6-tetramethylpiperidine, etc. Also suitable are inorganic bases such as sodium hydroxide, potassium hydroxide, sodium carbonate, potassium carbonate, calcium oxide, sodium hydrogen carbonate, etc.

The reaction can be carried out, for example, within a temperature range from −10° C. to +100° C. Preference is given to ranges from +10° C. to +70° C.

Additionally, compounds of the formula (I) can also be prepared, for example, by reacting a compound of the formula (V)

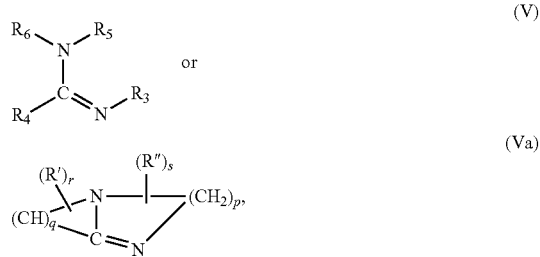

(V)

(Va)

in which $R_3$, $R_4$, $R_5$, $R_6$, R', R'', p, q, r and s are as defined above, including the preferred definitions, with a compound of the formula (VII)

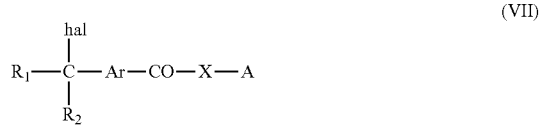

(VII)

in which $R_1$, $R_2$, Ar and X are as defined above, including the preferred definitions, hal is a halogen atom, $OCOR_{20}$ or $OSO_2R_{20}$, and $R_{20}$ is $C_1$-$C_8$alkyl, perfluoroalkyl or aryl which is substituted by one or more $C_1$-$C_4$alkyl or by fluorine;

and subjecting the reaction product to subsequent reduction.

"hal" is preferably bromine or chlorine.

The reaction of compounds of the formula (V) or (Va) with compounds of the formula (VII) can be carried out in a manner known per se. It is advantageous to use a solvent or mixture of solvents, examples being hydrocarbons such as benzene, toluene, xylene, etc., halogenated hydrocarbons, such as methylene chloride, chloroform, carbon tetrachloride, chlorobenzene, etc., alkanols such as methanol, ethanol, ethylene glycol monomethyl ether, etc., and ethers such as diethyl ether, dibutyl ether, tert-butyl methyl ether, ethylene glycol dimethyl ether, tetrahydrofuran, ketones such as acetone or 2-butanone or dimethyl sulfoxide. It is also possible to use mixtures of such solvents.

The reaction can be carried out, for example, within a temperature range from −10° C. to +100° C. Preference is given to ranges from 0° C. to +70° C.

The reaction described above produces a quaternary ammonium salt. This salt can be isolated or else converted directly by treatment with an appropriate reducing agent into the compounds of the formula (I) according to the invention. Reduction to the compounds of the formula (I) according to the invention can be carried out in accordance with a variety of processes which are known to the person skilled in the art. Suitable reducing agents, for example, are metal hydrides such as lithium aluminium hydride, sodium borohydride, sodium cyanoborohydride or dibutylaluminium hydride. Likewise suitable are reducing agents such as polymethylhydrosiloxanes in combination with an appropriate activator (Lawrence et al., J. Chem. Soc. Perkin Trans. I. (1999), 3381). Additionally, the catalytic reduction can be carried out with hydrogen, using the metal catalysts which are customary in the art and are known to the person skilled in the art.

The reduction conditions have to be selected in a way that the more reactive immonium group of the reaction product is selectively reduced without affecting the less reactive group —CO—X-A. This can be achieved under conditions known to a person skilled in the art, e.g. by using exactly one mole-equivalent of a metal hydride such as sodium borohydride or lithium aluminium hydride.

It is appropriate to use a solvent or mixture of solvents, examples being hydrocarbons such as benzene, toluene, xylene, etc., ethers such as diethyl ether, dibutyl ether, tert-butyl methyl ether, ethylene glycol dimethyl ether or tetrahydrofuran. Under specific conditions, depending on the base used, alkanols such as methanol, ethanol, etc. are also suitable.

The reaction can be carried out, for example, within a temperature range from −30° C. to +100° C. Preference is given to ranges from −10° C. to +30° C.

Compounds of the formula (I) may also be prepared, for example, by way of a rhodium-catalysed hydroformylation reaction, starting from appropriate N-alkenyl-α,ω-diamines. This process is described, for example, by Bergmann et al. in Aust. J. Chem. (1999), 52, 1131. The N-alkenyl-α,ω-diamine is reacted with carbon monoxide and hydrogen in an inert solvent, such as benzene, for example, under pressure and with rhodium catalysis. Examples of suitable catalysts are rhodium complexes such as may be prepared in situ, for example, from rhodium acetate and a phosphine such as triphenylphosphine or 6,6'-{[3,3'-bis(1,1-dimethylethyl)-5,5'-dimethoxy-1,1'-biphenyl]-2,2'-diyl}bis(oxy)-bis(dibenzo[d,f][1,3,2]dioxa-phosphepine (BIPHEPHOS).

Compounds of the formula (I) can also be prepared by further synthesis processes which are known to the person skilled in the art.

Compounds of the formula I, wherein n is greater than 1 are prepared in analogoues manner by employing appropriate n-valent starting materials instead of the monovalent compounds of formula (VII). That is the appropriate n-halogenides esters or sulfonates are employed.

Preferably in the above reaction(s) X is O and A denotes methyl or ethyl. To prepare compounds wherein A is other than methyl or ethyl, in other words to introduce different ester groups, the corresponding compound (VII) carrying the suitable substituent A can be used.

For the preparation of compounds wherein A has another meaning than ethyl or methyl, or wherein X not O, it may be advantageous the run the above reaction with compound (VII) in which A is methyl or ethyl, followed by a conventional transesterification reaction known to the person skilled in the art.

The transesterification or aminolyis is performed with a suitable ≥n-functional polyalcohol or ≥n-functional polyamine in order to introduce the n-valent group. Suitably, a "≥n"="more than n"-functional polyalcohol or polyamine is used, as generally not all alcohol or amine groups take part in the esterification or amidation reaction.

When a monofunctional alcohol is used for the transesterification reaction, compounds of formula (I) or (II) with X=O and n=1 are obtained.

If a polyfunctional alcohol is used, as mentioned above, not all alcohol groups may react to form ester groups. Depending on the reaction conditions, e.g. the ratio of the starting materials, "uniform compounds", i.e. compounds wherein all or a defined number of the polyfunctional groups have reacted, as well "mixed compounds", i.e. a mixture of compounds wherein different numbers of the polyfunctional groups have reacted, or blends of "mixed compounds" are obtained. Thus, it is evident for the person skilled in the art, that the esterification may result in the formation of "uniform compounds" only or "mixed compounds only as well as, in mixtures of "uniform compounds" with "mixed compounds". All products, "uniform compounds", "mixed compounds" as well as mixtures of both are subject of the invention.

It is obvious that mixtures of compounds can be separated by the usual methods familiar to the person skilled in the art, such as for example distillation, chromatography, crystallization, However, the mixtures also can be used such as photolatent base compounds.

Similar considerations apply for the aminolysis, if polyfunctional amines are employed in the reaction, i.e. "uniform compounds", "mixed compounds" as well as mixtures of both can be obtained, depending on the reaction conditions.

Similar considerations further apply for the reaction products of compounds of formula (III) with polyisocyanates, i.e. "uniform compounds", "mixed compounds" as well as mixtures of both can be obtained, depending on the reaction conditions.

Transesterification reactions can be performed under conditions known to the person skilled in the art. These include for example heating the ester compound in the presence of the alcohol to be introduced, while the low-molecular methanol or ethanol produced is distilled off from the reaction mixture. Distillation of the low-molecular alcohol can for example be facilitated by applying vacuum to the reaction vessel. In many cases it is advantageous to use a catalyst which facilitates the transesterification reaction and allows the use of lower temperatures. Useful catalysts are for example Lewis or Brönsted acids, Lewis or Brönsted bases or nucleophiles or metal salts (see for example A. G. Grasa et al., Synthesis (2004), (7), 971; J. Otera et al., Acc. Chem. Res. (2004), 37, 288; H. E. Hoydonckx et al. Topic in Catalysis (2004), 27, O. A. Mascaretti et al. Aldrichimica Acta (1997), 30, 55; R. Sridharan et. al. J. Scient. & Indust. Research (1974), 33, 178). Suitable enzymes are also frequently used to facilitate transesterification reactions (see for example E. Santaniello et al. Current Org. Chem (2006), 10, 1059; S. Negishi, Handbook of Industrial Biocatalysis, CRC Press, (2005), 12/1-12/14; H. J. Altenbach, Nachrichten aus Chemie, Technik, und Laboratorium (1988), 36(10), 1114).

To prepare compounds wherein X is $N(R_{10})$, in other words to introduce an amide group, the corresponding compound (VII) carrying the suitable amide group can be used as starting material. In many cases it may be advantageous the run the above reaction with compound (VII) in which X is oxygen and A is methyl or ethyl, followed by a conventional aminolyse reaction known to the person skilled in the art.

Aminolyse reactions can be performed under conditions known to the person skilled in the art. These include for example heating the ester compound in the presence of the amine to be introduced, while the low-molecular methanol or ethanol produced is distilled off from the reaction mixture. Distillation of the low-molecular alcohol for example can be facilitated by applying vacuum to the reaction vessel. In many cases it is advantageous to use a catalyst which facilitates the transesterification reaction and allows the use of lower temperatures. Useful catalysts are for example cyanide or stable carbenes (T. Hogberg et al. J. Org. Chem. (1987), 52, 2033; M. Movassaghi et al., Org. Lett. (2005), 7, 2453). Enzymes can also be used to facilitate aminolyse reaction (see e.g. V. Gotor-Fernandez, Current Organic Chemistry (2006), 10(10), 1125-1143).

Other useful catalysts are group (IV) metal alkoxide-activator complexes (C. Han et al., J. Am. Chem. Soc. 2005, 127, 10039).

For example the esters can be reacted with monofunctional amines, such as alkylamine or alkenylamines, or with multifunctional amines, such as polyethylene-imines, such as for example LUPASOL® FG, provided by BASF AG.

Examples for starting materials for transesterification reactions are given below.

If A denotes a substituent carrying additional functional groups, the latter can further be transformed in a way known to a person skilled in the art, by reaction with a reagent suitable to react with said functional group.

For example:

The compounds of the formula (II) for example are prepared by reacting a compound of the formula (VI)

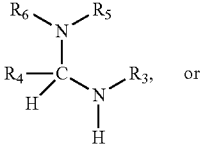

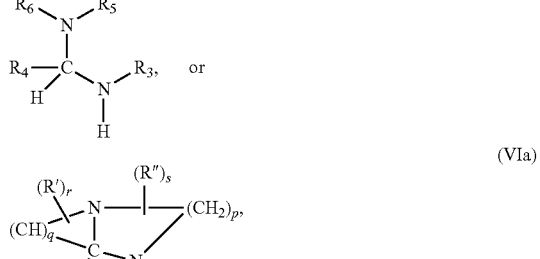

in which
$R_3$, $R_4$, $R_5$, $R_6$, R', R'', p, q, r and s are as defined above, including the preferred meanings, with a compound of the formula (IX)

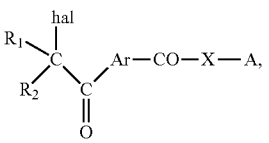

in which
$R_1$, $R_2$, Ar and X are as defined above, including the preferred definitions,
hal is Cl, Br, I, $OCOR_{20}$ or $OSO_2R_{20}$,
and, in a second step, conducting a Wittig reaction with the reaction product thus obtained, using a phosphonium salt of the formula (X)

$$R_7R_8CH\text{—}P(phenyl)_3{}^+Z^- \quad (X),$$

in which
$R_7$ and $R_8$ are as defined above, including the preferred meanings, and Z is F, Cl, Br, I or tetrafluoroborate.

Suitable Wittig reagents (phosphonium salts) are obtainable commercially and are mentioned, for example, in Lancaster Chemical Catalogue, Appendix 1, pages A2-A6.

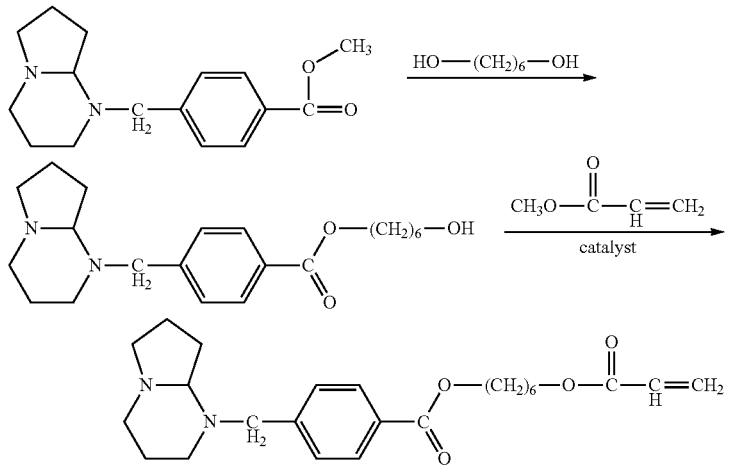

Examples are: methyltriphenylphosphonium bromide, methyltriphenylphosphonium iodide, ethyltriphenylphosphonium chloride, ethyltriphenylphosphonium bromide, ethyltriphenylphosphonium iodide, n-propyltriphenylphosphonium bromide, n-butyltriphenylphosphonium chloride, n-butyltriphenylphosphonium bromide, isobutyltriphenylphosphonium bromide, n-amyltriphenylphosphonium bromide, isoamyltriphenylphosphonium bromide, n-hexyltriphenylphosphonium bromide, n-heptyltriphenylphosphonium bromide, n-octyltriphenylphosphonium bromide, n-nonyltriphenylphosphonium bromide, n-decyltriphenylphosphonium bromide, n-undecyltriphenylphosphonium bromide, n-dodecyltriphenylphosphonium bromide, n-tetradecyltriphenylphosphonium bromide, n-hexadecyltriphenylphosphonium bromide, trimethylsilylmethyltriphenylphosphonium iodide, 2-dimethylaminoethyltriphenylphosphonium bromide, 2-chloroethyltriphenylphosphonium bromide, 2-hydroxyethyltriphenylphosphonium bromide, 3-bromopropyltriphenylphosphonium bromide, 4-bromobutyltriphenylphosphonium bromide, 2-(1,3-dioxan-2-yl)ethyltriphenylphosphonium bromide, cyclopropylmethyltriphenylphosphonium bromide, 4-carboxybutyltriphenylphosphonium bromide, 4-carboethoxybutyltriphenylphosphonium bromide, 4-pentenyltriphenylphosphonium bromide, 5-hexenyltriphenylphosphonium bromide, 3-phenylpropyltriphenylphosphonium bromide, ethylenebis(triphenylphosphonium bromide), trimethylenebis(triphenylphosphonium bromide), tetramethylenebis(triphenylphosphonium bromide), pentamethylenebis(triphenylphosphonium bromide), isopropyltriphenylphosphoni-umiodide, 2-butyltriphenylphosphonium bromide, 2-amyltriphenylphosphonium bromide, cy-clopropyltriphenylphosphonium bromide, cyclopentyltriphenylphosphonium bromide, cyclo-hexyltriphenylphosphonium bromide, cycloheptyltriphenylphosphonium bromide, allylti-phenylphosphonium chloride, allyltriphenylphosphonium bromide, 2-methylallyltriphenylphosphonium chloride, 3-methylallyltriphenylphosphonium chloride, 3,3-dimethylallyltriphenylphosphonium bromide, 2-butene-1,4-bis(triphenylphosphonium chloride), cinnamyltriphenylphosphonium chloride, cinnamyltriphenylphosphonium bromide, pro-pargyltriphenylphosphonium bromide, benzyltriphenylphosphonium chloride, benzyltriphenylphosphonium bromide, benzyltriphenylphosphonium iodide, 2-methylbenzyltriphenylphosphonium chloride, 2-methylbenzyltriphenylphosphonium bromide, 3-methylbenzyltriphenylphosphonium chloride, 4-methylbenzyltriphenylphosphonium chloride, 4-methylbenzyltriphenylphosphonium bromide, 2-hydroxybenzyltriphenylphosphonium bromide, 4-methoxybenzyltriphenylphosphonium chloride, 4-ethoxybenzyltriphenylphosphonium bromide, 4-butoxybenzyltriphenylphosphonium bromide, 4-fluorobenzyltriphenylphosphonium chloride, 4-chlorobenzyltriphenylphosphonium chloride, 4-bromobenzyltriphenylphosphonium bromide, 4-cyanobenzyltriphenylphosphonium chloride, 4-carbomethoxybenzyltriphenylphosphonium bromide, 2-nitrobenzyltriphenylphosphonium bromide hydrate, 4-nitrobenzyltriphenylphosphonium bromide, o-xylylenebis(triphenylphosphonium bromide), p-xylylenebis(triphenylphosphonium chloride), p-xylylenebis(triphenylphosphonium bromide), 1-naphthylmethyltriphenylphosphonium chloride, benzhydryltriphenylphosphonium chloride, hydroxymethyltriphenylphosphonium chloride, methoxymethyltriphenylphosphonium chloride, chloromethyltriphenylphosphonium iodide, methylthiomethyltriphenylphosphonium chloride, phenylthiomethyltriphenylphosphonium chloride, 1,3-dithian-2-yltriphenylphosphonium chloride, formylmethyltriphenylphosphonium chloride, acetonyltriphenylphosphonium chloride, acetonyltriphenylphosphonium bromide, phenacyltriphenylphosphonium bromide, α-methylphenacyltriphenylphosphonium bromide, carbomethoxymethyltriphenylphosphonium chloride, carbomethoxymethyltriphenylphosphonium bromide, carboethoxymethyltriphenylphosphonium chloride, carboethoxymethyltriphenylphosphonium bromide, 1-carboethoxyethyltriphenylphosphonium bromide, methyl 4-(triphenylphosphonio)crotonate bromide, 1-carboethoxycyclopropyltriphenyl-phosphonium tetrafluoroborate, cyanomethyltriphenylphosphonium chloride, 2-(triphenylphosphoranylidene)succinic anhydride, 9-fluorenyltriphenylphosphonium bromide, vinyltri-phenylphosphonium bromide, or 1,2-vinylenebis(triphenylphosphonium bromide).

The reaction of compounds of formula (VI), (VIa) with compounds of formula (IX) are conducted in a manner known per se. Advantageously, a solvent or mixture of solvents is used, examples being hydrocarbons such as benzene, toluene, xylene, etc., halogenated hydrocarbons such as methylene chloride, chloroform, carbon tetrachloride, chlorobenzene, etc., alkanols such as methanol, ethanol, ethylene glycol monomethyl ether, etc., and ethers such as diethyl ether, dibutyl ether, ethylene glycol dimethyl ether, etc., and mixtures of such solvents.

The reaction can judiciously be conducted within a temperature range from −10° C. to 100° C.

Preference is given to reaction temperatures from 10° C. to 50° C.

The Wittig reaction is for example carried out in a conventional manner. It is advantageous to use a solvent or solvent mixture, e.g. hydrocarbons such as benzene, toluene, xylene, etc., halogenated hydrocarbons such as methylene chloride, chloroform, carbon tetrachloride, chlorobenzene, etc., alkanols such as methanol, ethanol, ethylene glycol monomethyl ether, etc. and ethers such as diethyl ether, dibutyl ether, ethylene glycol dimethyl ether, etc. and mixtures of these solvents.

The reaction can be carried out within a temperature range from −10° C. to 100° C. Ranges are preferably from 10° C. to 70° C.

The compounds of the formula (II) can also be prepared by reacting a compound of the formula (VI)

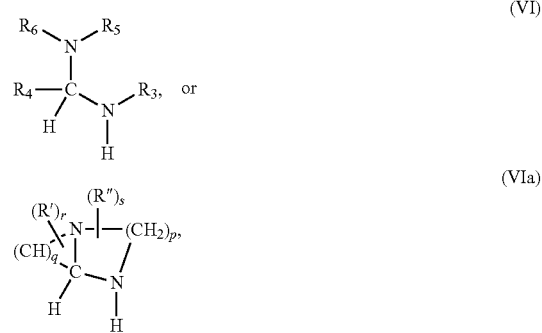

in which

R$_3$, R$_4$, R$_5$, R$_6$, R', R", p, q, r and s are as defined above, including the preferred meanings, with a compound of the formula (XII)

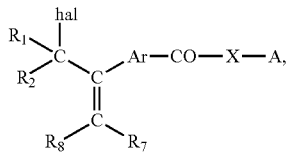

(XII)

in which

R$_1$, R$_2$, R$_7$, R$_8$, Ar and X are as defined above, including the preferred definitions, hal is Cl, Br, I, OCOR$_{20}$ or OSO$_2$R$_{20}$, under reaction conditions known to a person skilled in the art, e.g. as described above for the reaction of (VI) or (VIa) with (VII).

Compounds, wherein n is greater than 1 are prepared in analogoues manner by employing appropriate n-valent starting materials instead of the monovalent compounds of formula (IX). That is the appropriate n-halogenides are employed. Another method is to first prepare the monoester and by way of transesterification or aminolyis with a suitable ≥n-functional polyalcohol or ≥n-functional polyamine introduce the n-valent group.

The methods to prepare compounds of the formula (III) are in analogy to the methods described above for the compounds of the formula (I). However the starting material of the formula (VII) is replaced by

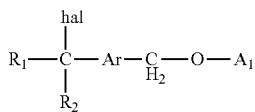

(XI)

in which

R$_1$, R$_2$, Ar and A$_1$ are as defined above, including the preferred definitions, hal is a halogen atom, OCOR$_{20}$ or OSO$_2$R$_{20}$, and R$_{20}$ is C$_1$-C$_8$alkyl, perfluoroalkyl or aryl which is substituted by one or more C$_1$-C$_4$alkyl or by fluorine. hal is preferably bromine or chlorine.

Another method to prepare the compounds of the formula III is to reduce the ester component of a compound of the formula I, e.g. with lithiumaluminum hydride, lithium borohydride, sodium in ethanol (Bouveault-Blanc procedure), hydrogenation over suitable catalysts such as copper chromite or other methods known to the art-skilled person, to the corresponding alcohol and then introduce A$_1$ via reactions known per se, e.g. substitution or addition reactions:

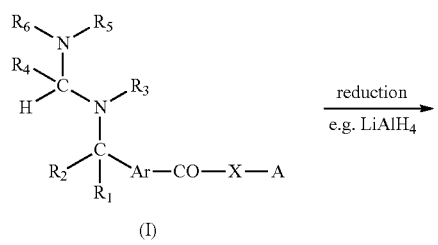

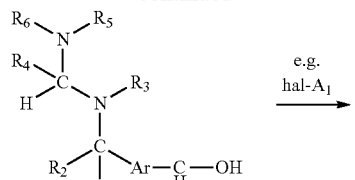

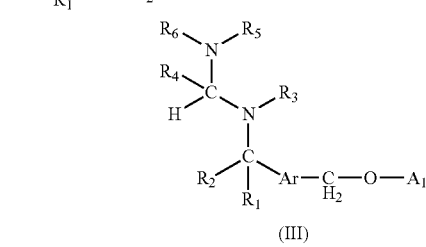

(III)

The reactions shown above are based on conventional chemistry and the person skilled in the art is familiar therewith and knows about the appropriate conditions to take.

They include—but are not limited to—for example ether formation under the conditions of the Williamson ether synthesis, esterification with suitable carboxylic acid or carboxylic acid chlorides, transesterification with suitable esters, ring opening of cyclic esters such as caprolactone, addition to isocyanates or epoxides. Compounds, wherein n is greater than 1 are prepared in analogoues manner by employing appropriate n-valent starting materials instead of the monovalent compounds such as hal-A$_1$. That is for example the appropriate n-halogenides, n-carboxylic acids, n-carboxylic acid chlorides, n-carboxylic esters, n-isocyanates, or n-epoxides are employed for the above mentioned reaction of the alcohol group.

Additionally, compounds of the formula (III) can also be prepared by reacting a compound of the formula (V)

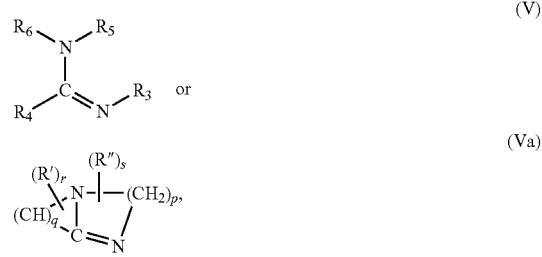

in which

R$_3$, R$_4$, R$_5$, R$_6$, R', R", p, q, r and s are as defined above, including the preferred definitions, with a compound of the formula (VII)

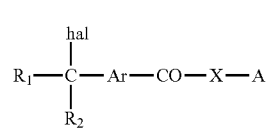

(VII)

in which

R$_1$, R$_2$, Ar and X are as defined above, including the preferred definitions, hal is a halogen atom, OCOR$_{20}$ or OSO$_2$R$_{20}$, and R$_{20}$ is C$_1$-C$_8$alkyl, perfluoroalkyl or aryl which is substituted by one or more C$_1$-C$_4$alkyl or by fluorine;

and subjecting the reaction product to subsequent reduction.

hal is preferably bromine or chlorine.

Compounds of formula (III) with n=1 and A$_1$=H are obtained by this reaction sequence.

These compounds can be further transformed by methods known to the person skilled in the art, and discussed before, into compounds of formula (III) with n=1-10 and A$_1$ as defined above, including the preferred definitions, but different from H.

The reaction described above produces a quaternary ammonium salt. This salt can be isolated or else converted directly by treatment with an appropriate reducing agent into the compounds of the formula (I) according to the invention. Reduction to the compounds of the formula (I) according to the invention can be carried out in accordance with a variety of processes which are known to the person skilled in the art. Suitable reducing agents, for example, are metal hydrides such as lithium aluminium hydride, sodium borohydride, sodium cyanoborohydride or dibutylaluminium hydride. Likewise suitable are reducing agents such as polymethylhydrosiloxanes in combination with an appropriate activator (Lawrence et al., J. Chem. Soc. Perkin Trans. I. (1999), 3381). Additionally, the catalytic reduction can be carried out with hydrogen, using the metal catalysts which are customary in the art and are known to the person skilled in the art.

The reduction conditions have to be selected in a way that both the more reactive immonium group of the reaction product and the less reactive group —CO—X-A are reduced, either parallel or in subsequent reaction steps, in a one-pot reaction. This can be achieved under conditions known to a person skilled in the art, e.g. by using at least three, preferentially more mole-equivalents of a metal hydride such as sodium borohydride or lithium aluminium hydride. Monovalent (n=1) compounds (III) with A$_1$=H are obtained under these conditions. These compounds can be further transformed into monovalent (n=1) or multivalent (n>1) by the reactions described before.

It is appropriate to use a solvent or mixture of solvents, examples being hydrocarbons such as benzene, toluene, xylene, etc., ethers such as diethyl ether, dibutyl ether, tert-butyl methyl ether, ethylene glycol dimethyl ether or tetrahydrofuran. Under specific conditions, depending on the base used, alkanols such as methanol, ethanol, etc. are also suitable.

The reaction can be carried out, for example, within a temperature range from −30° C. to +100° C. Preference is given to ranges from −10° C. to +30° C.

To prepare compounds of formula (III) wherein A$_1$ is alkanoyl, alkenoyl or aroyl, in other words to introduce different ester groups, the corresponding compound (III) with n=1 and A$_1$=H can be subjected to a conventional transesterification reaction known to the person skilled in the art.

The transesterification reaction is performed with a suitable ≥n-functional polyester in order to introduce the n-valent group. Suitably, a "≥n"="more than n"-functional polyalcohol or polyamine is used, as generally not all alcohol or amine groups take part in the esterification or amidation reaction.

Similary as discussed above for the compounds of the formula (I) and (II) also here, depending on the reaction conditions, e.g. the ratio of the starting compound (III) in which n=1 and A$_1$=H, and the polyfunctional ester "uniform compounds", i.e. compounds wherein all or a defined number of the polyfunctional groups have reacted, as well "mixed compounds", i.e. a mixture of compounds wherein different numbers of the polyfunctional groups have reacted, or blends of "mixed compounds" are obtained.

When a lactone is used instead of an ester under conditions known to the person skilled in the art, compounds (III) with n=1 are obtained, in which the lactone moiety is incorporated once or several times in the group A$_1$.

Similar considerations apply for the corresponding aminolysis reactions. For example to prepare compounds of formula (III) wherein A$_1$ is alkylaminocarbonyl or arylaminocarbonyl, the corresponding compound (III) with n=1 and A$_1$=H can be subjected to a conventional reaction with an isocyanate under reaction conditions known to the person skilled in the art.

When, for example a monofunctional isocyanate is used for the urethane formation reaction, compounds of formula (III) with n=1 are obtained, while, if a polyfunctional amine or a "≥n"="more than n"-functional isocyanate, is employed in the reaction, "uniform compounds", "mixed compounds", as well as mixtures of both can be obtained, depending on the reaction conditions.

As mentioned above, in the preparation of the photolatent bases of formula (I), (II) and (III) of the invention, isomer mixtures may be formed. These mixtures can be separated, for example, by customary methods which are known to the person skilled in the art. However, it is also possible to use each of the isomer mixtures formed as photolatent bases directly.

To prepare the n-valent starting materials of the formulae (VII), (IX) and (XI), which are employed in the above-described reactions for the preparation of the compounds of the formula (I), (II) and (III), for example the compounds listed below with n-valent linking groups are suitable in the context of the present application.

For example, a diol is reacted with a compound of the formula VII to give the corresponding di-valent starting material, which then is reacted to the compound of formula I:

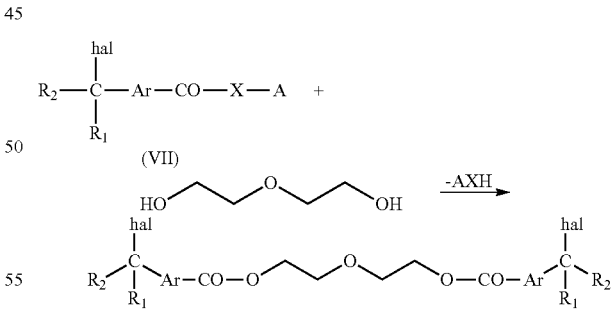

The below listing of starting materials to prepare n-valent compounds of the formulae (VII), (IX) and (XI), has to be understood as a non-limiting scope of examples.

(1) examples of suitable diols and oligo-alcohols

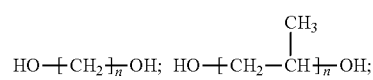

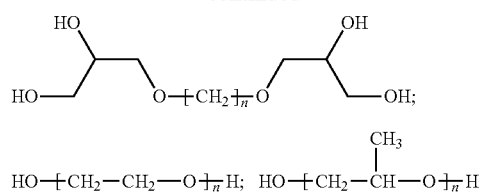

with for example n=1-20;

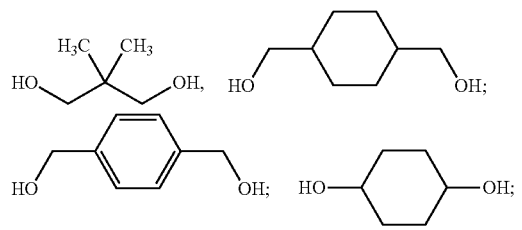
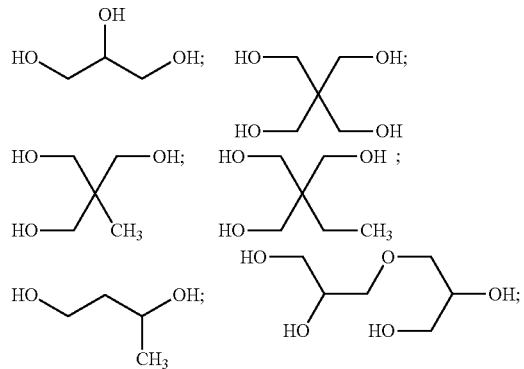
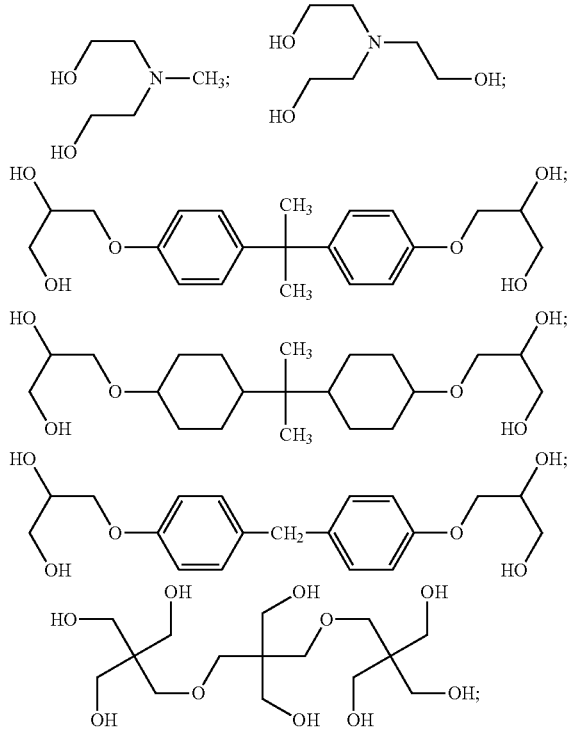

R = C$_1$—C$_3$-Alkyl  $q$ = 3-5  $p$ = 1-6  $s$ = 2-6  $r$ = 1-6

H$+$O—CH$_2$—CH$_2$$\}_m$$+$O—$(CH_2)_q$—CO$\}_p$—OH;

$m$ = 1-6  $q$ = 3-5  $p$ = 1-6

HO$+$CO—$(CH_2)_q$—O$\}_p$$+$$(CH_2)_4$—O$\}_m$H;

$q$ = 3-5  $p$ = 1-6  $m$ = 1-6

H$+$O—CH(CH$_3$)—CH$_2$$\}_m$$+$O—$(CH_2)_q$—CO$\}_p$—OH;

$m$ = 1-6  $q$ = 3-5  $p$ = 1-6

HO$+$CO$+$(CH$_2$)$_q$—O$\}_p$$+$CH$_2$—CH(CH$_3$)—O$\}_m$H;

$q$ = 3-5  $p$ = 1-6  $m$ = 1-6

HO$+$O$+$(CH$_2$)$_4$$\}_m$$+$O—(CH$_2$)$_q$—CO$\}_p$—OH;

$m$ = 1-6  $q$ = 3-5  $p$ = 1-6

HO$+$CO$+$(CH$_2$)$_q$—O$\}_p$$+$(CH$_2$)$_4$—O$\}_m$H.

$q$ = 3-5  $p$ = 1-6  $m$ = 1-6

(2) Examples of suitable dithiols and polythiols

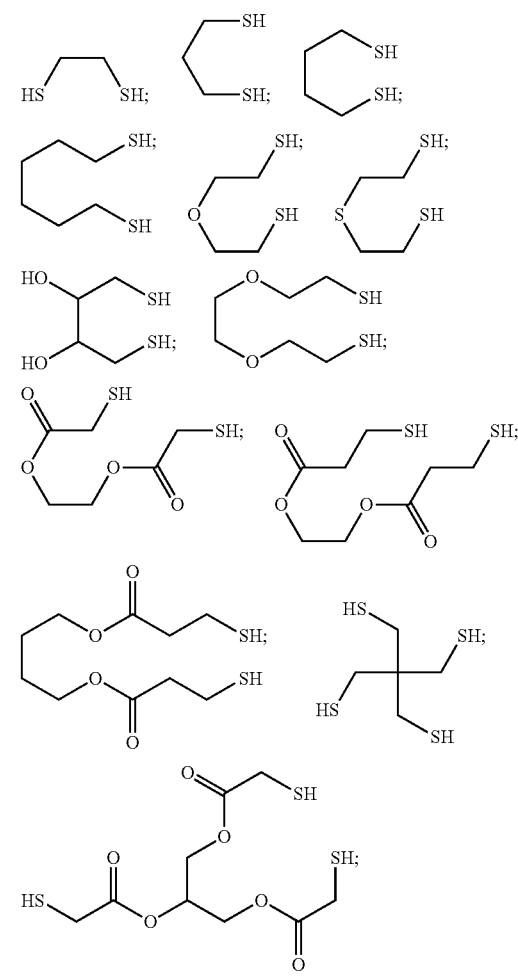

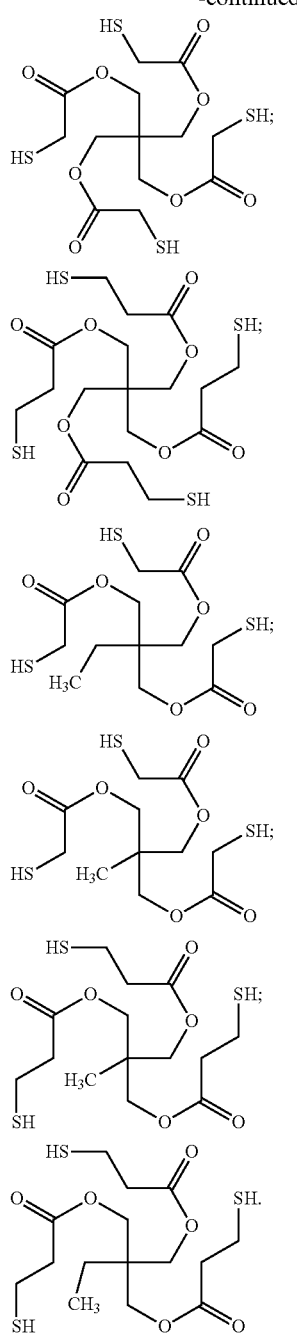
(3) examples of suitable dicarboxylic acids and polycarboxylic acids
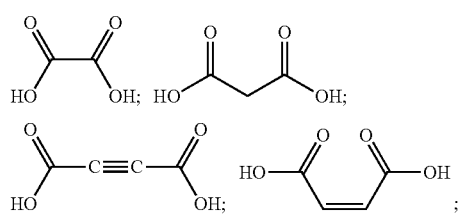
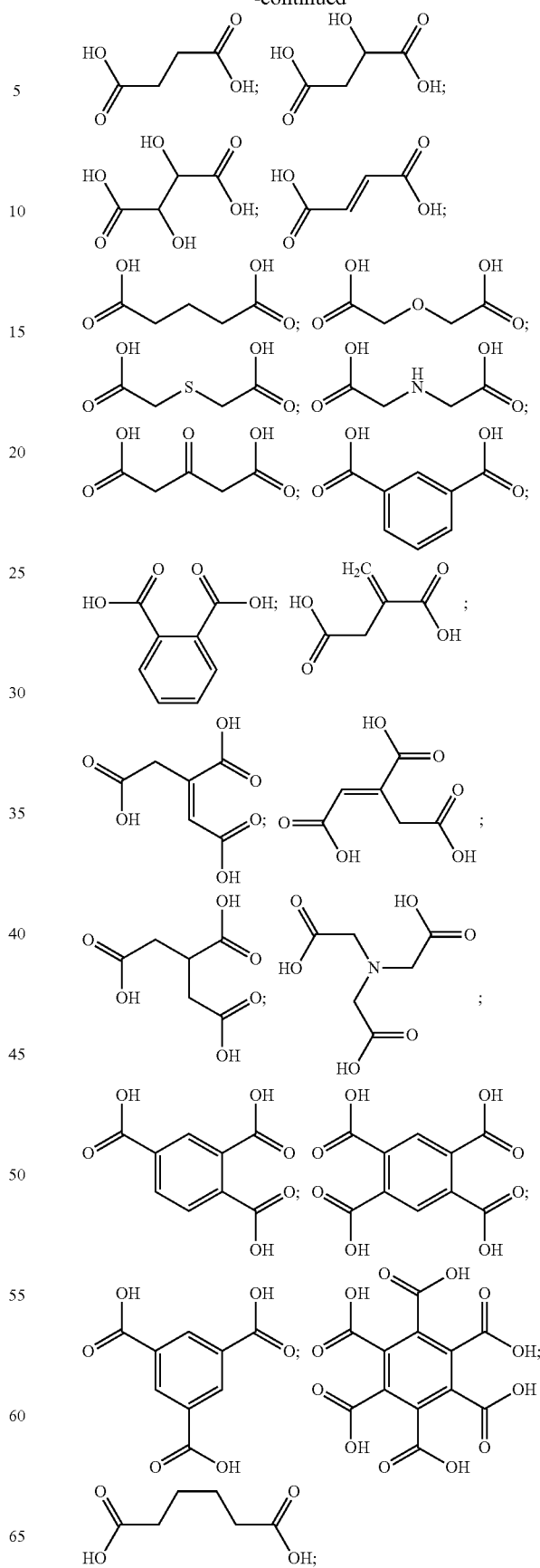

-continued
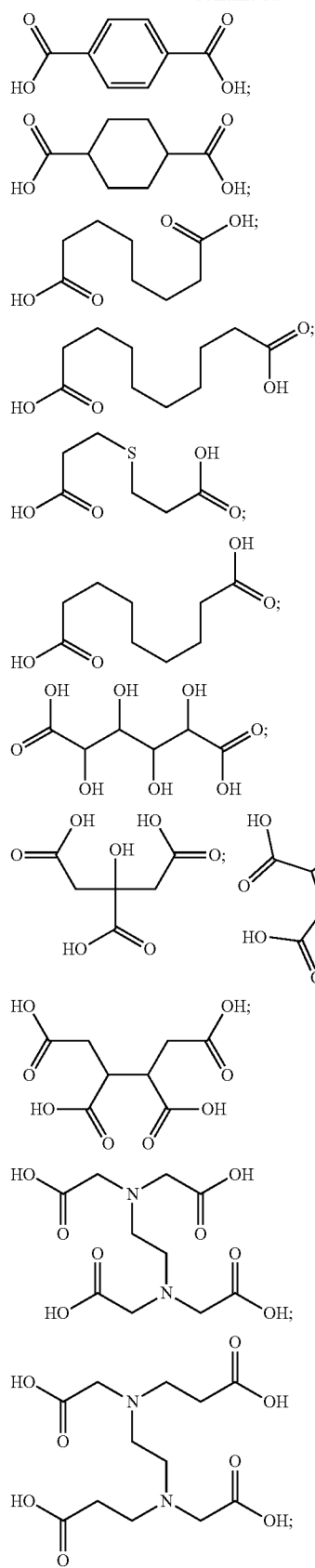
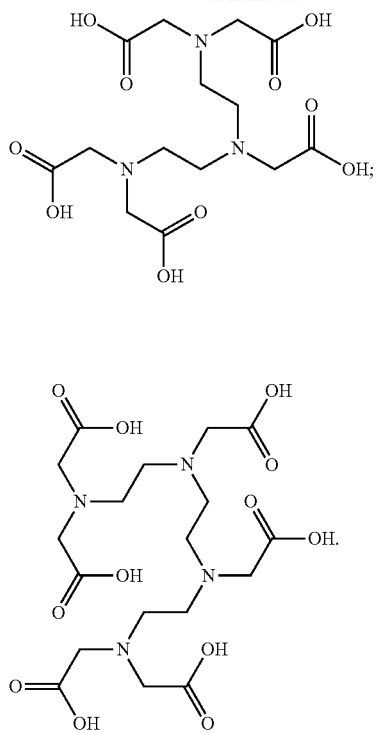
(4) examples of suitable acid chlorides
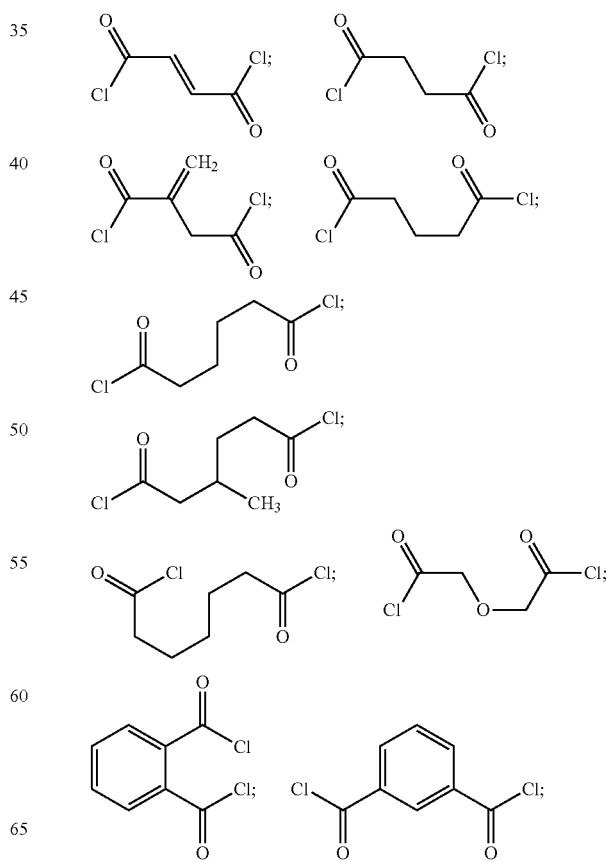

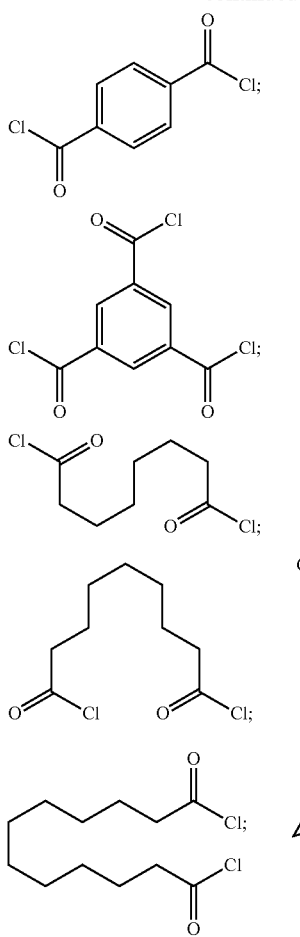
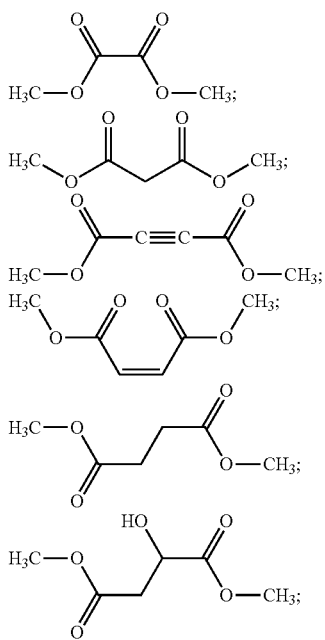
(5) examples of suitable di- and polycarboxylic acids esters
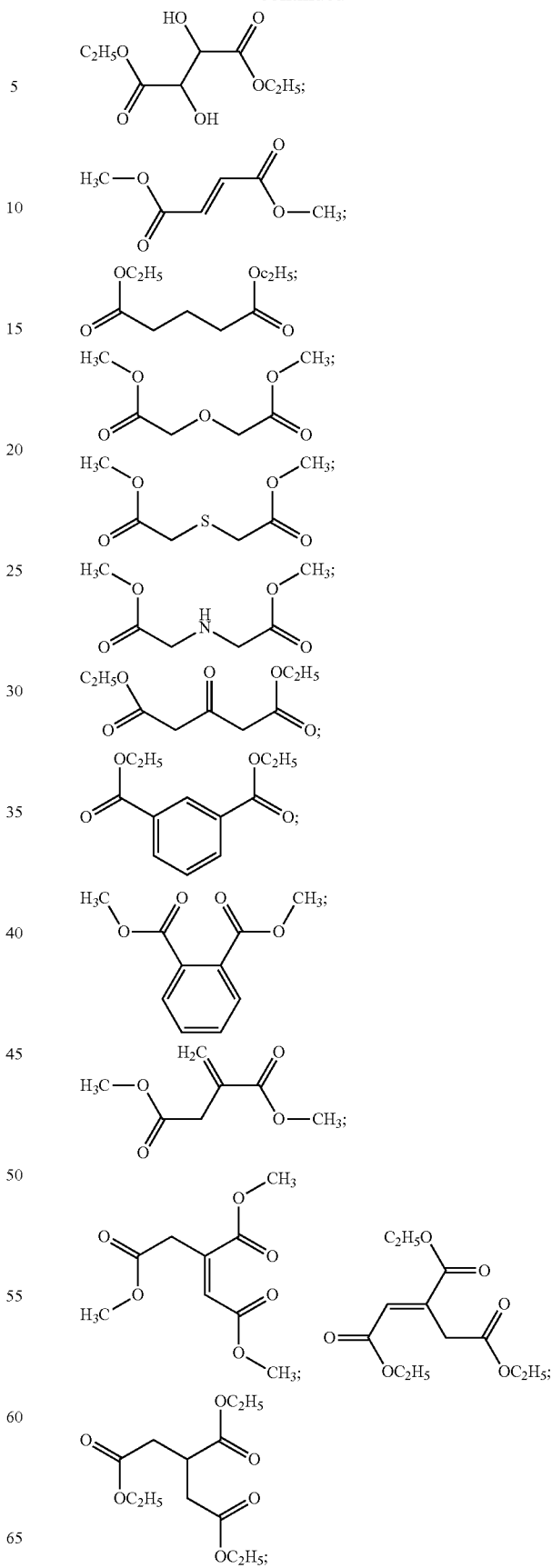

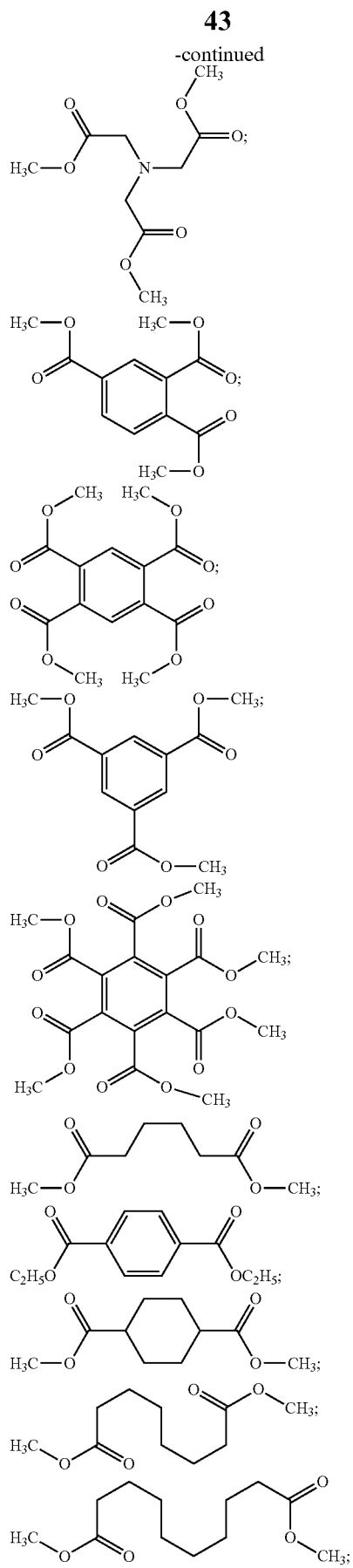
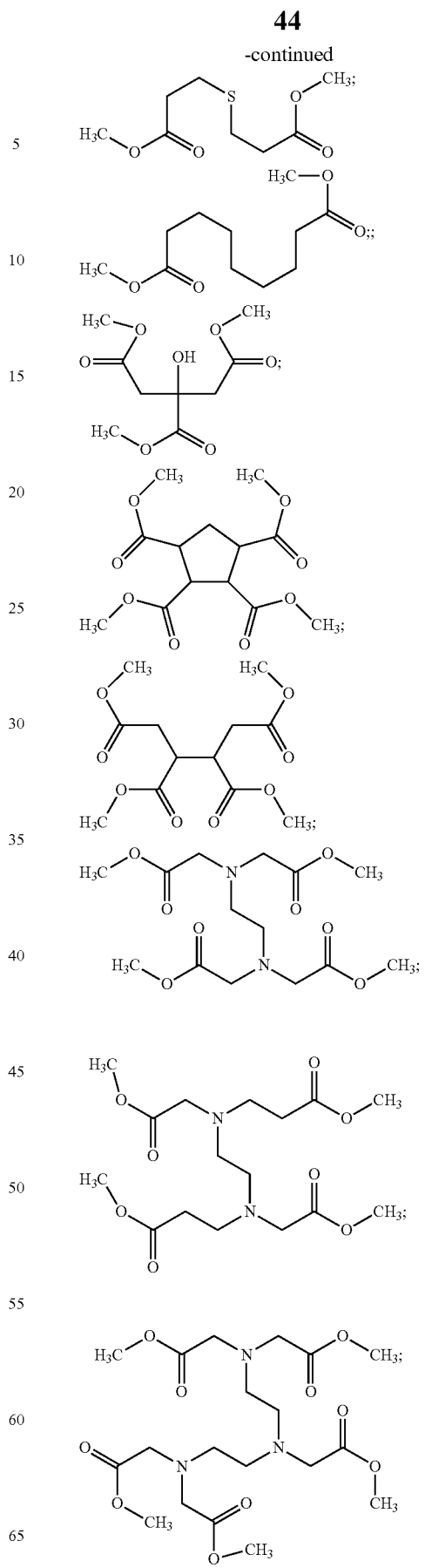

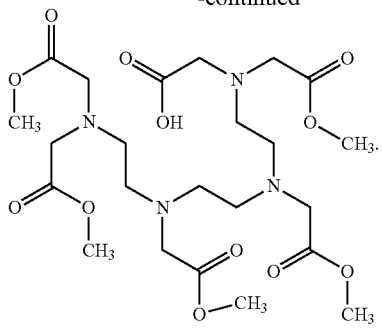
(6) examples of suitable diamines and polyamines (polyalkylene imines)
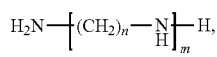
with, for example, n=1-6 and m≥1;
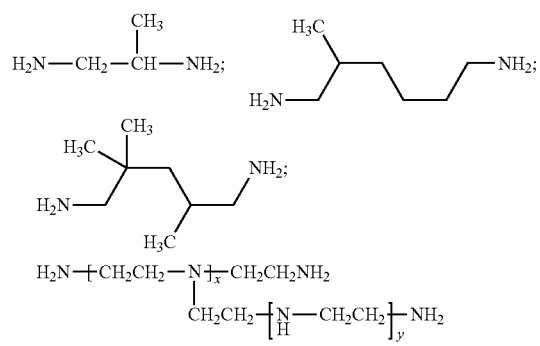
with e.g. x and y≥1;
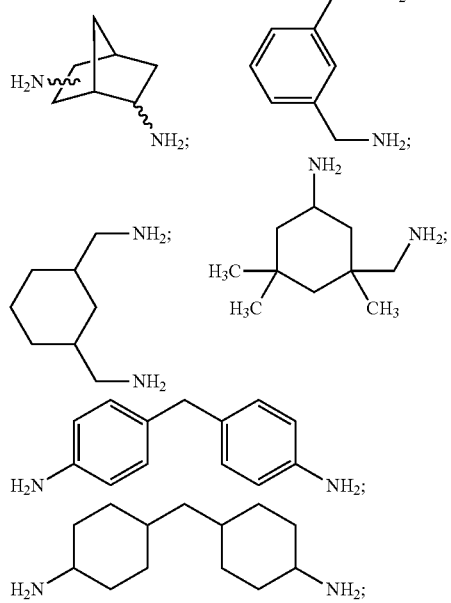
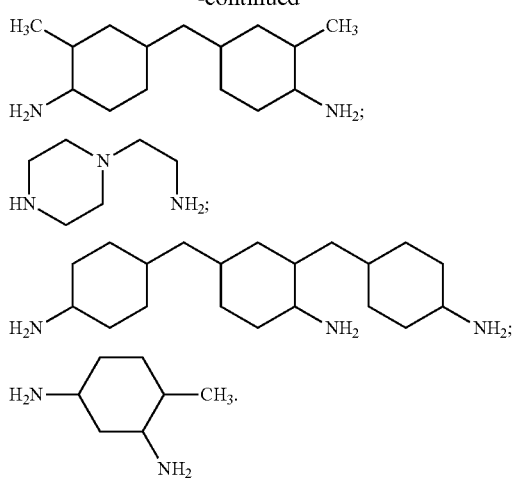
It is also possible to use epoxides, isocyanates or lactones in the reaction for compounds of the formula III. Examples of suitable compounds of this kind are
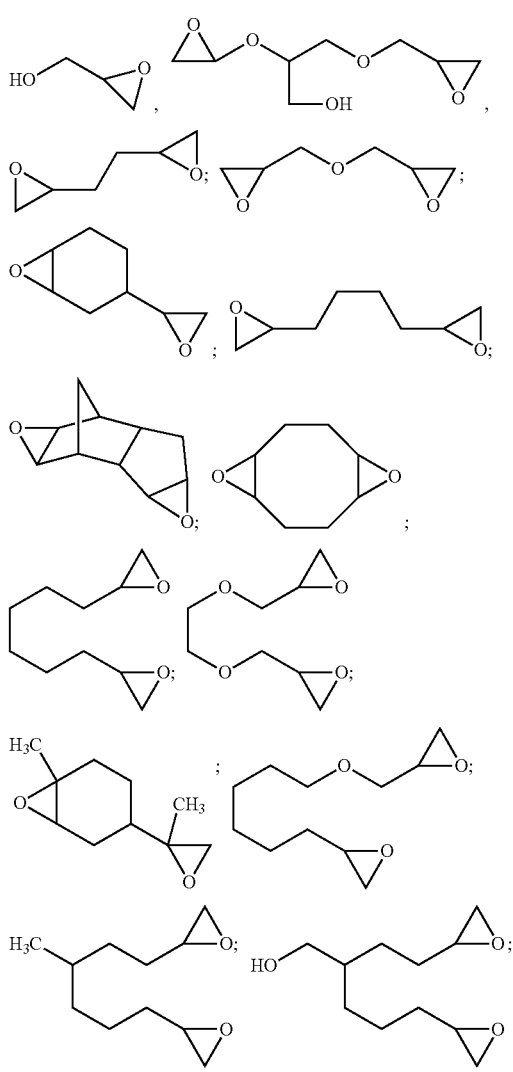

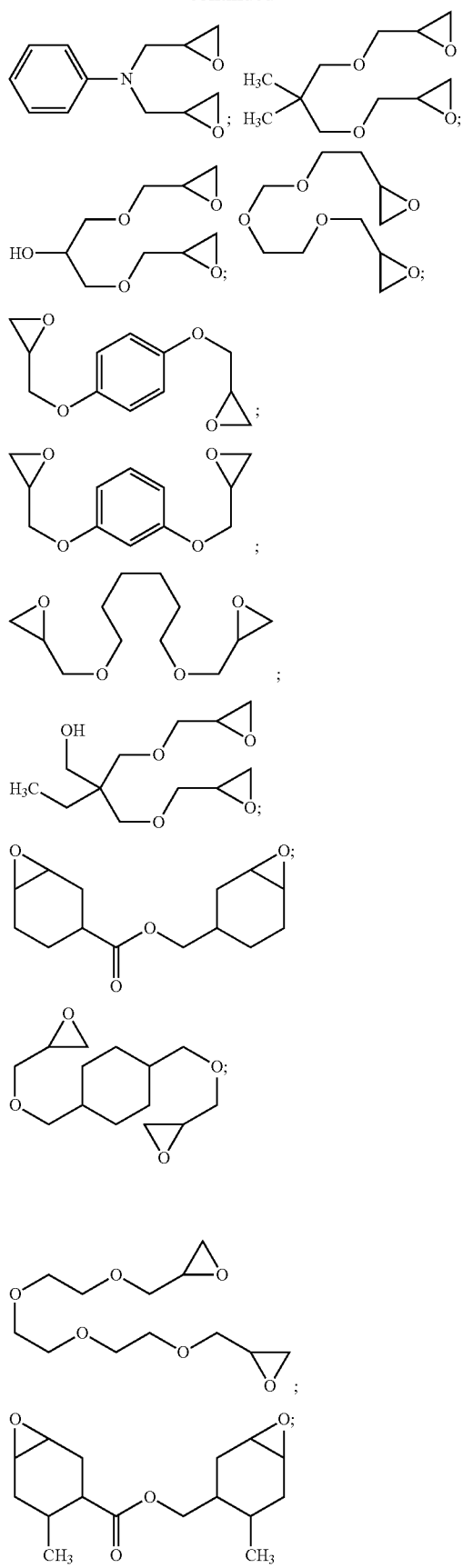
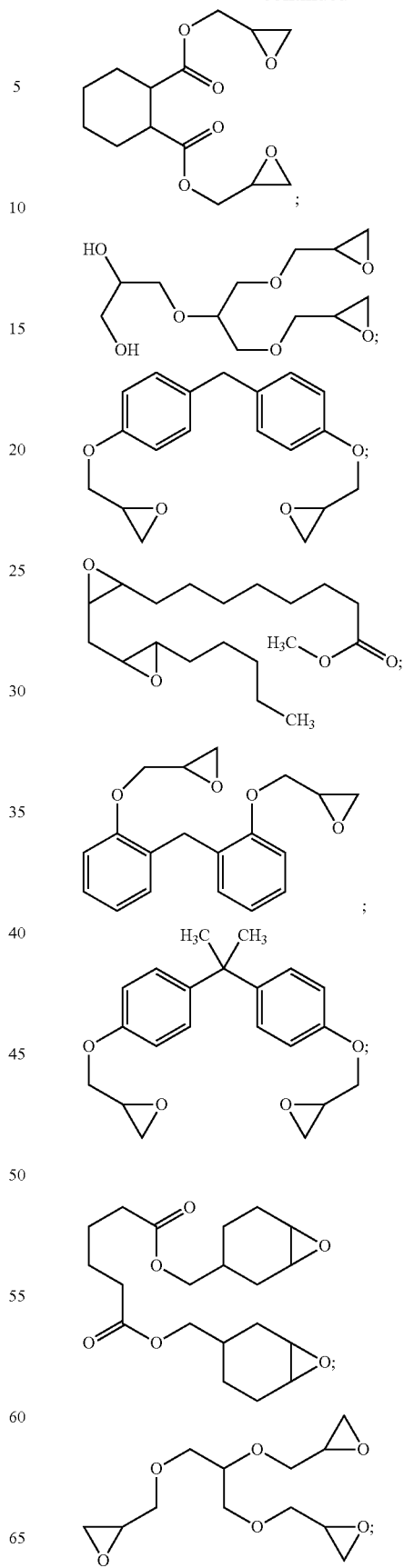

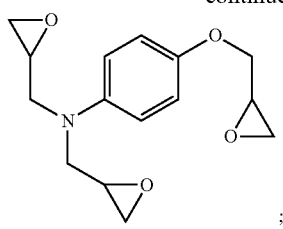
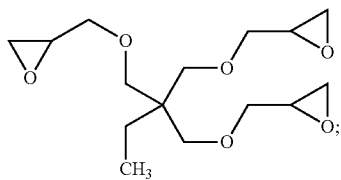
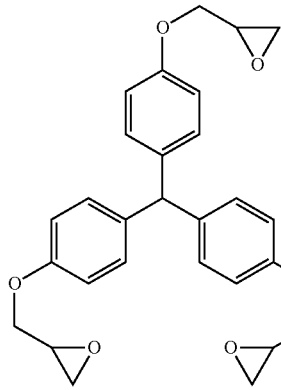
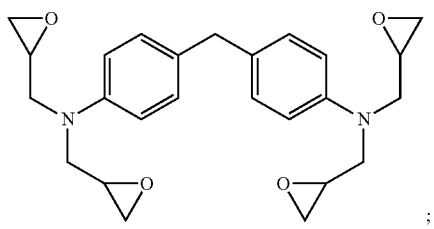
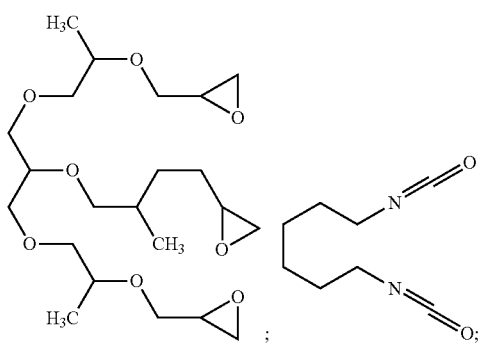
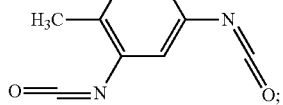
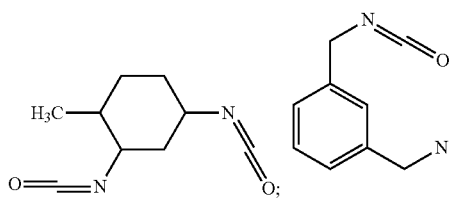
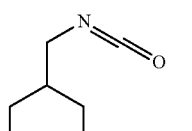
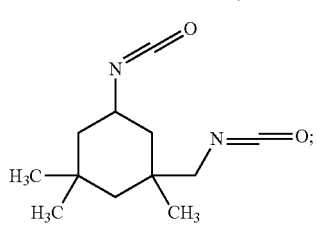
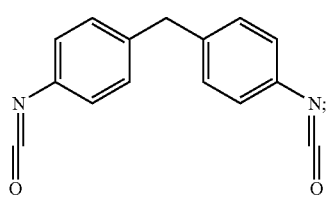
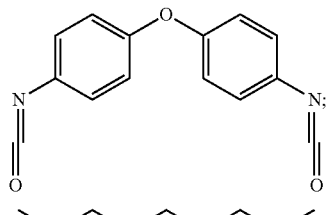
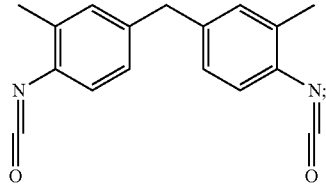
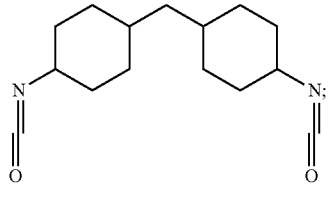
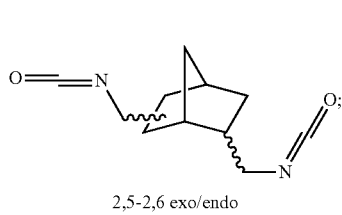
2,5-2,6 exo/endo
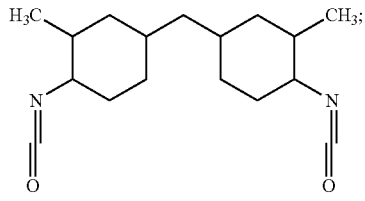

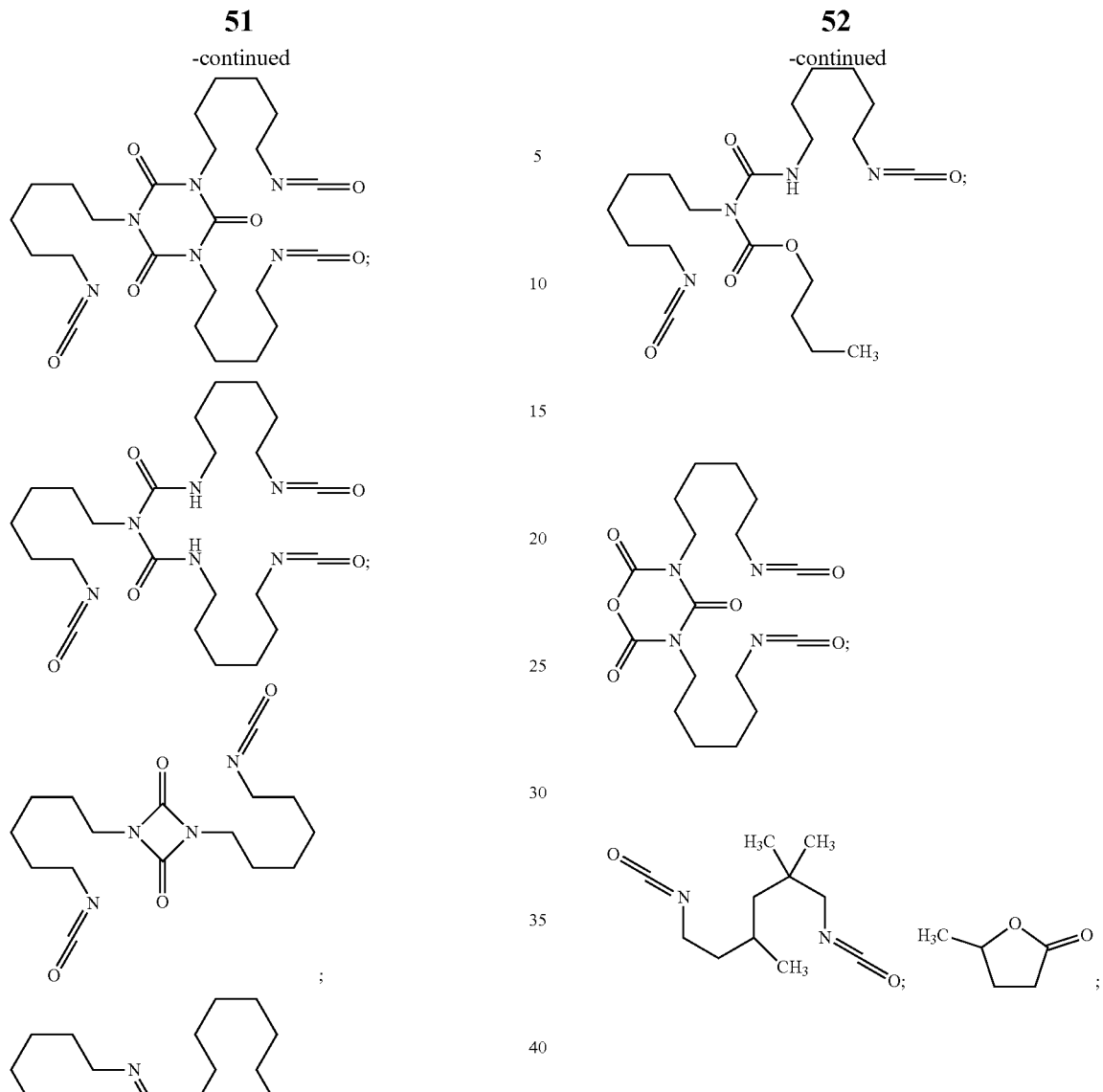
Reaction with a lactone, for example results in the formation of the corresponding photolatent base with a long chain substitutent:
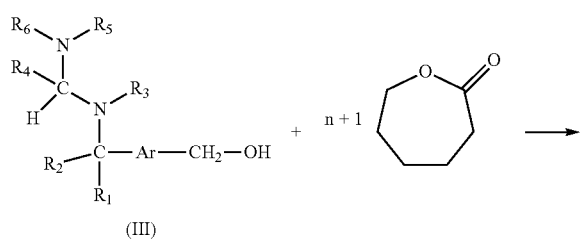

-continued

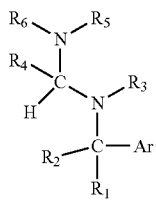

(III)'

The compounds of the formula (I), (II) and (III) of the present invention, where X is O; n is 1; A is hydrogen or $C_1$-$C_{18}$-alkyl; and $A_1$ is hydrogen or $C_2$-$C_{18}$-alkanoyl, i.e. compounds of the formula

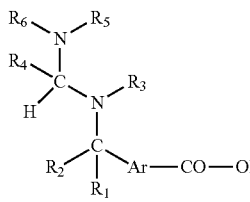

(I')

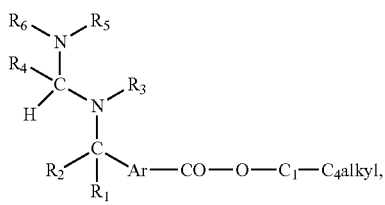

(I")

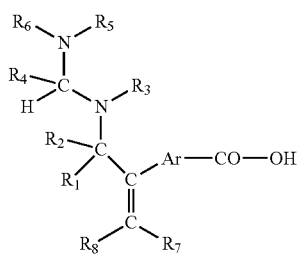

(II')

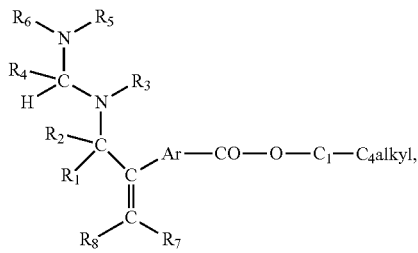

(II")

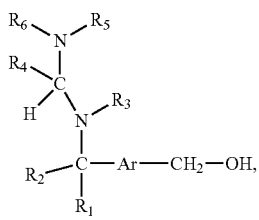

(III')

wherein $R_1$, $R_2$, $R_3$, $R_4$, $R_5$, $R_6$, $R_7$, $R_8$ and Ar are defined as above, are suitable as starting materials for the preparation of polyfunctional photolatent amines by reacting said compounds of formula (I), (II) or (III) with polyfunctional alcohols, amines, thiols, epoxides, carboxylic acids, carboxylic acid chlorides or carboxylic acid esters.

Examples of such polyfunctional alcohols, amines, thiols, epoxides, carboxylic acids, carboxylic acid chlorides or carboxylic acid esters are customary in the art and known to the skilled person. Specific examples are given above.

Accordingly, subject of the present invention also is the use of a photolatent base compound of the formula (I), (II) or (III) according to claim 1, wherein
X is O;
n is 1;
A is hydrogen or $C_1$-$C_{18}$-alkyl; and
$A_1$ is hydrogen or $C_2$-$C_{18}$-alkanoyl;
as starting material for the preparation of polyfunctional photolatent amines by reacting said compounds of formula (I), (II) or (III) with polyfunctional alcohols, amines, thiols, epoxides, isocyanates, carboxylic acids or carboxylic acid chlorides.

Photolatent base compounds of the formula (I), (II) and (III) of the present invention, wherein X s O; n is 1; A is hydrogen or $C_1$-$C_{18}$-alkyl; and $A_1$ is hydrogen or $C_2$-$C_{18}$-alkanoyl, i.e. compounds of the formula (I'), (I"), (II'), (II") and (III') as described above, are further useful components in the preparation of oligomers, such as for example polyester oligomers, polyurethane oligomers or poly(caprolactone) oligomers, which are end-capped with photolatent amine groups.

Oligomers in this context are to be understood as non-monomeric, low-molecular polymer compounds. The physical properties of oligomers in general do change to a measurable ex-tend if one constitutional unit is added or deleted, while this is not the case for a polymer. Dimeric, trimeric, tetrameric etc. compounds in this context are considered as oligomers; for example compounds of a molecular mass higher than 1000 g/mol up to about 10000 g/mol.

Therefore, subject of the invention also is the use of a photolatent base compound of the formula (I), (II) or (III) according to claim 1, wherein
X is O;
n is 1;
A is hydrogen or $C_1$-$C_{18}$-alkyl; and
$A_1$ is hydrogen or $C_2$-$C_{18}$-alkanoyl;
as components for the preparation of oligomers which are end-capped with photolatent amine groups.

In accordance with the invention, the compounds of the formula (I), (II) and (III) can be used as photolatent bases. That is, the compounds of the formula (I), (II) and (III) release a base upon exposure to electromagnetic radiation. Thus, subject of the invention is also a process to prepare a base compound, by irradiating a compound of the formula (I), (II) or (III); in particular a process for preparing a compound of the formula (V)

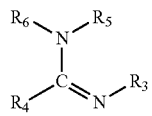

in which

R$_3$, R$_4$, R$_5$ and R$_6$ are as defined in claim 1;

which process comprises subjecting a compound of the formula (I), (II) or (III) according to claim 1 to irradiation with light having a wavelength of from 200 nm to 650 nm, where appropriate in the presence of a sensitizer (C).

The invention further provides a composition comprising (A) at least one photolatent base compound of the formula (I), (II) or (III) according to claim 1; and (B) at least one organic compound which is capable of a base-catalysed addition, condensation or substitution reaction or which is converted into a different form by a base-catalysed reaction.

The base-catalysed polymerization, addition, condensation or substitution reaction may be carried out with low molecular mass compounds (monomers), with oligomers, with polymeric compounds, or with a mixture of such compounds. Examples of reactions which can be conducted both on monomers and on oligomers/polymers using the photoinitiators of the invention are the Knoevenagel reaction and the Michael addition reaction or the addition reaction of polyols with poly(isocyanates). Where appropriate, the presence of further components, such as atmospheric humidity in the case of the base-catalyzed crosslinking of isocyanates or acryloyloxysilanes or acyloxysilanes, is beneficial to or necessary for the reaction. This is disclosed, for example, in EP 1092757. Furthermore, some of the compounds undergoing a crosslinking reaction can be present in a blocked form. Typical examples are blocked isocyanates such as for example disclosed in European Patent Application No. 06121469.8, the disclosure of which hereby is incorporated by reference. Further examples are given below.

Of particular importance are compositions in which component (B) is an organic material which is polymerized or crosslinked by a base-catalyzed reaction.

The organic material may be in the form of monofunctional or polyfunctional monomers, oligomers or polymers.

Particularly preferred oligomeric/polymeric systems are binders such as are customary in the coatings and adhesives industry and known to the person skilled in the art.

Examples of base-catalysable binders of this kind are:

a) acrylic copolymers with alkoxysilane and/or alkoxysiloxane side groups, examples being the polymers described in U.S. Pat. Nos. 4,772,672, 4,444,974 or EP 1092757;

b) two-component systems comprising hydroxyl-containing polyacrylates, polyesters and/or polyethers and aliphatic or aromatic polyisocyanates;

c) two-component systems comprising functional polyacrylates and polyepoxide, the polyacrylate containing thiol, amino, carboxyl and/or anhydride groups, as described, for example, in EP 898202;

d) two-component systems comprising fluorine-modified or silicone-modified, hydroxyl-containing polyacrylates, polyesters and/or polyethers and aliphatic or aromatic polyisocyanates;

e) two-component systems comprising (poly)ketimines and aliphatic or aromatic polyisocyanates;

f) two-component systems comprising (poly)ketimines and unsaturated acrylic resins or acetoacetate resins or methyl α-acrylamidomethylglycolate;

h) two-component systems comprising (poly)oxazolidines and polyacrylates containing anhydride groups or unsaturated acrylic resins or polyisocyanates;

i) two-component systems comprising epoxy-functional polyacrylates and carboxyl-containing or amino-containing polyacrylates;

l) polymers based on allyl glycidyl ether;

m) two-component systems comprising a (poly)alcohol and/or (poly)thiol and a (poly)isocyanate;

n) two-component systems comprising an α,β-ethylenically unsaturated carbonyl compound and a polymer containing activated CH$_2$ groups, the activated CH$_2$ groups being present either in the main chain or in the side chain or in both, as is described, for example, in EP 161697 for (poly)malonate groups. Other compounds containing activated CH$_2$ groups are (poly)acetoacetates and (poly)cyanoacetates.

o) Two-component systems comprising a polymer containing activated CH$_2$ groups, the activated CH$_2$ groups being present either in the main chain or in the side chain or in both, or a polymer containing activated CH$_2$ groups such as (poly)acetoacetates and (poly)cyanoacetates, and a polyaldehyde crosslinker, such as terephthalaldehyde. Such systems are described, for example, in Urankar et al., Polym. Prepr. (1994), 35, 933.

p) Two-component or one-component systems comprising blocked isocyanates and a hydrogen donor. Such systems are described for example in European Patent Application No. 06121469.8, the disclosure of which hereby is incorporated by reference.

q) Thiol Michael systems. Examples are described by F. Cellesi et al. in Biomaterials (2004), 25(21), 5115.

Within this group of base-catalysable binders, the following are particularly preferred:

a) acrylic copolymers with alkoxysilane and/or alkoxysiloxane side groups, examples being the polymers described in U.S. Pat. No. 4,772,672, 4,444,974 or EP 1092757 and an application of which is described in WO 2005/100482 A1;

b) two-component systems comprising hydroxyl-containing polyacrylates, polyesters and/or polyethers and aliphatic or aromatic polyisocyanates;

c) two-component systems comprising functional polyacrylates and a polyepoxide, the polyacrylate containing thiol, amino, carboxyl and/or anhydride groups;

i) two-component systems comprising epoxy-functional polyacrylates and carboxyl-containing or amino-containing polyacrylates;

m) two-component systems comprising a (poly)alcohol and/or (poly)thiol and a (poly)isocyanate, n) two-component systems comprising an α,β-ethylenically unsaturated carbonyl compound and a polymer containing activated CH$_2$ groups, the activated CH$_2$ groups being present either in the main chain or in the side chain or in both; and p) Two-component or one-component systems comprising blocked isocyanates and a hydrogen donor. Such systems are described below and for example in European Patent Application No. 06121469.8, the disclosure of which hereby is incorporated by reference.

q) Thiol Michael systems

Two-component systems comprising an α,β-ethylenically unsaturated carbonyl compound and a (poly)malonate and their preparation are described in EP 161687. The malonate group may either be attached in the main chain or in a side chain of a polyurethane, polyester, polyacrylate, epoxy resin, polyamide or polyvinyl polymer. The $\alpha,\beta$-ethylenically unsaturated carbonyl compound can be any double bond activated by a carbonyl group. Examples are esters or amides of acrylic acid or methacrylic acid. In the ester groups it is also possible for there to be additional hydroxyl groups. Diesters and triesters are possible as well.

Typical are, for example, hexanediol diacrylate or trimethylolpropane triacrylate. Instead of acrylic acid it is also possible to use other acids and their esters or amides, such as crotonic acid or cinnamic acid, for example.

The components of the system react with one another under base catalysis at room temperature to form a cross-linked coating system which is suitable for a large number of applications. Because of its already good weathering stability it is also suitable, for example, for exterior applications and can where necessary be further stabilized by UV absorbers and other light stabilizers.

Further suitable components (B) in the compositions of the invention include epoxy systems.

Epoxy resins suitable for preparing curable mixtures of the invention comprising epoxy resin components B) are the epoxy resins which are customary in epoxy resin technology. Examples of such resins are:

Polyglycidyl esters and poly($\beta$-methylglycidyl) ester, obtainable by reacting a compound having at least two carboxyl groups in the molecule with epichlorohydrin or $\beta$-methylepichlorohydrin, respectively. The reaction takes place appropriately in the presence of bases.

As the compound having at least two carboxyl groups in the molecule it is possible to use aliphatic polycarboxylic acids. Examples of such polycarboxylic acids are oxalic acid, succinic acid, glutaric acid, adipic acid, pimelic acid, suberic acid, azeleic acid or dimerized or trimerized linoleic acid. It is, however, also possible to use cycloaliphatic polycarboxylic acids, such as tetrahydrophthalic acid, 4-methyltetrahydrophthalic acid, hexahydrophthalic acid or 4-methylhexahydrophthalic acid. It is also possible for aromatic polycarboxylic acids to be used, such as phthalic acid, isophthalic acid or terephthalic acid.

Polyglycidyl ethers or poly-($\beta$-methylglycidyl) ethers obtainable by reacting a compound containing at least two free alcoholic hydroxyl groups and/or phenolic hydroxyl groups with epichlorohydrin or $\beta$-methylepichlorohydrin, respectively, under alkaline conditions, or in the presence of an acidic catalyst with subsequent alkali treatment.

The glycidyl ethers of this type derive, for example, from acyclic alcohols, such as from ethylene glycol, diethylene glycol and higher poly(oxyethylene) glycols, propane-1,2-diol or poly(oxypropylene) glycols, propane-1,3-diol, butane-1,4-diol, poly(oxytetramethylene) glycols, pentane-1,5-diol, hexane-1,6-diol, hexane-2,4,6-triol, glycerol, 1,1,1-trimethylolpropane, pentaerythritol, sorbitol, and from polyepichlorohydrins. They also derive, however, for example, from cycloaliphatic alcohols, such as 1,4-cyclohexanedimethanol, bis(4-hydroxy-cyclohexyl)methane or 2,2-bis(4-hydroxycyclohexyl)propane, or possess aromatic nuclei, such as N,N-bis(2-hydroxyethyl)aniline or p,p'-bis (2-hydroxyethylamino)diphenylmethane. The glycidyl ethers may also derive from mononuclear phenols, such as from resorcinol or hydroquinone, for example, or are based on polynuclear phenols, such as bis(4-hydroxyphenyl)methane, 4,4'-dihydroxybiphenyl, bis(4-hydroxyphenyl) sulfone, 1,1,2,2-tetrakis(4-hydroxyphenyl)ethane, 2,2-bis(4-hydroxyphenyl)propane, 2,2-bis(3,5-dibromo-4-hydr-oxyphenyl)propane, and also from novolaks obtainable by condensation of aldehydes, such as formaldehyde, acetaldehyde, chloral or furfuraldehyde, with phenols, such as phenol, or with phenols substituted in a nucleus by chlorine atoms or $C_1$-$C_9$alkyl groups, such as 4-chlorophenol, 2-methylphenol, or 4-tert-butylphenol, or by condensation with bisphenols, those of the type specified above.

Poly(N-glycidyl) compounds obtainable by dehydrochlorinating the reaction products of epichlorohydrin with amines containing at least two amine hydrogen atoms. These amines are, for example, aniline, n-butylamine, bis(4-aminophenyl)methane, m-xylylenediamine or bis(4-methylaminophenyl)methane.

The poly(N-glycidyl) compounds also include, however, triglycidyl isocyanurate, N,N'-diglycidyl derivatives of cycloalkyleneureas, such as ethyleneurea or 1,3-propyleneurea, and di-glycidyl derivatives of hydantoins, such as 5,5-dimethylhydantoin.

Poly-(S-glycidyl) compounds, examples being di-S-glycidyl derivatives deriving from dithiols, such as ethane-1, 2-dithiol or bis(4-mercaptomethylphenyl) ether.

Cycloaliphatic epoxy resins, examples being bis(2,3-epoxycyclopentyl) ether, 2,3-epoxycyclopentyl glycidyl ether, 1,2-bis(2,3-epoxycyclopentyloxy)ethane and 3,4-epoxycyclohexyl-methyl 3',4'-epoxycyclohexanecarboxylate.

It is, however, also possible to use epoxy resins where the 1,2-epoxide groups are attached to different heteroatoms and/or functional groups; these compounds include, for example, the N,N,O-triglycidyl derivative of 4-aminophenol, the glycidyl ether glycidyl ester of salicylic acid, N-glycidyl-N'-(2-glycidyloxypropyl)-5,5-dimethylhydantoin and 2-glycidyloxy-1,3-bis(5,5-dimethyl-1-glycidylhydantoin-3-yl)propane.

As component (B) it is also possible to use mixtures of epoxy resins. Also in accordance with the invention, therefore, are compositions comprising as component (B) an epoxy resin or a mixture of different epoxy resins.

The photolatent bases of the present invention are in particular suitable for curing isocyanate-based formulations. With the photolatent base compounds according to the present invention an improved stability in said systems is given and an enhanced cure-speed is achieved. The isocyanate formulations may for example comprise the isocyanate or isothiocyanate in a blocked form.

In particular interesting therefore are compositions comprising as component (B) a (poly)alcohol and/or polythiol and a isocyanate or isothiocyanate, wherein the isocyanate or isothiocyanate optionally is a (poly)blocked isocyanate or (poly)blocked isothiocyanate.

Blocked isocyanates are known in the art and for example described in a review article by D. A. Wicks, Z. W. Wicks in *Progress in Organic Coatings*, 41 (2001), 1-83, as well as by C. Gürtler, M. Homann, M. Mager, M. Schelhaas, T. Stingl, Farbe+Lack 2004, 110(12), 34; both documents incorporated herein by reference.

The terms "isocyanate" and isothiocyanates are used herein to refer to mono- and polyisocyanates and to mono- and polyisothiocyanates.

In general the term covers any compound containing one or more —N=C=Y groups in which Y is oxygen or sulfur. Examples of polyisocyanates suitable for the present invention include aliphatic compounds such as trimethylene, tetramethylene, pentamethylene, hexamethylene, 1,2-propylene, 1,2-butylene, 2,3-butylene, 1,3-butylene, ethylidine and butylidene diisocyanates. Additionally, the cycloalkylene diisocyanates can be employed such as 1,3-cyclopentane, 1,4-cyclohexane, and 1,2-cyclohexane diisocyanates. Aromatic diisocyanates are also suitable, such as m-phenylene, p-phenylene, 4,4'-diphenyl, 1,5-naphthalene and 1,4-napthalene diisocyanates as well as the aliphatic-aromatic diisocyanates such as 4,4'-diphenylene methane, 2,4- or 2,6-tolylene or mixtures thereof, 4,4'-toluidine, and 1,4-xylylene diisocyanates. Substituted aryl or aromatic diisocyanates may also be employed such as dianisidine diisocyanate, 4,4'-diphenylether diisocyanate and chlorodiphenylene diisocyanate, 1,8-diisocyanato-menthane, 1-methyl-2,4-diisocyanatocyclohexane, chlorophenylene diisocyanates, diphenyl-methane-4,4'-diisocyanate and naphthalene-1,5-diisocyanate. Additionally, the triisocyanates such as triphenyl methane-4,4',4"-triisocyanate, 1,3,5-triisocyanate benzene and 2,4,6-triisocyanate toluene may also be employed. Further tetraisocyanates may be utilized such as for example 4,4'-diphenol-dimethyl methane-2,2',5,5'-tetraisocyanate as well as other isocyanates such as xylylene-diisothiocyanate, isopropylbenzene-diisocyanate and polymerized polyisocyanates such as toluene diisocyanate dimers and trimers; dianisidine diisocyanate (CAS Registry No. 91-93-0); toluidine diisocyanate (CAS Registry No. 91-97-4); biuret of hexamethylene diisocyanate (CAS Registry No. 4035-89-6); isophorone diisocyanate (CAS Registry No. 4098-71-9); polymeric diphenol ethane diisocyanate (CAS Registry No. 9016-87-9) or 4,4'-dicyclohexylmethane diisocyanate. Various mixtures of isocyanates may also be used especially two, three, or four component mixtures.

The organic polyisocyanates may also be a prepolymer derived from a polyol and a polyisocyanate so that the polyol contains an isocyanate group or groups where the polyols include polyether polyols or polyester polyols or simple polyols such as glycols, including ethylene glycol and propylene glycol as well as glycerol, trimethylolpropane, hexanetriol, pentaerythritol, and the like.

The above summary of suitable isocynate components is not to be understood as limiting for the present invention, but only as list of illustrative examples.

As noted herein, the isocyanate of the component (B) of the present invention comprises a blocked isocyanate which is to say that the reactive isocyanate groups are reacted with any suitable blocking agent.

Examples of component (B) also are bis(cyclic ureas). These are blocked aliphatic diisocyanates and are preferred in some embodiments because no byproducts are formed upon release of the reactive isocyanate groups. These compounds can be referred to as self blocked isocyanates. Examples of these bis-cyclic ureas are described by Ulrich, ACS Svmm. Ser. 172 519 (1981, Sherwood, J. Coat. Technol. 54 (689), 61 (1982) and Kirk-Othmer Encyclopedia of Chemical Technology, Third Edition, Volume 23, p. 584 all of which are incorporated herein by reference.

Suitable blocking agents for the isocyanates are the ones known in the art, for example alcohols, phenols, amines, imides, amides, guanidines, amidines, triazoles, pyrazoles, active methylene compounds, ketoximes, oximes, malonesters, alkylacetoacetates, formiates, lactams, imidazoles, triazoles, pyrazoles, CH-acidic cyclic ketones and mercaptans.

Examples are aliphatic, cycloaliphatic, aromatic, or alkyl monoalcohol or phenolic compounds such as, for example, lower aliphatic alcohols including methyl, ethyl, chloroethyl, propyl, butyl, amyl, hexyl, heptyl, octyl, nonyl, decyl and lauryl alcohols, 3,3,5-trimethylhexanol and the like. The aromatic-alkyl alcohols include for example phenylcarbinol and ethylphenylcarbinol. Glycol ethers may be employed such as ethyl glycol monoethyl ether, ethyl glycol monobutyl ether and equivalents thereof. Examples of phenolic compounds which may be employed comprise phenol, substituted phenols such as cresol, xylenol, nitrophenol, chlorophenol, ethyl phenol, t-butyl phenol and 2,5-di-t-butyl-4-hydroxy toluene.

Examples of other blocking agents that may be employed include tertiary hydroxyl amines such as diethylethanolamin, lactams such as caprolactam and oximes such as methyl ethyl ketone oxime, acetone oxime and cyclohexanone oxime.

Specific examples are butanonoxime, diisoproylamine, 1,2,4-triazole, dimethyl-1,2,4-triazole, imidazole, ethylates of malonic and acetic acid, acetoneoxime, 3,5-dimethylpyrazole, epsilon-caprolactame, N-methyl-, N-ethyl, N-(iso)propyl, N-n-butyl, N-iso-butyl-, N-tert.-butylbenzylamine or, 1,1-dimethylbenzylamine, N-alkyl-N-1,1-dimethylmethylphenylamine; adducts of benzylamine and compounds with activated double bonds, such as malonic acid esters, N,N-dimethylaminopropylbenzylamine and other compounds comprising tertiary amine groups, where appropriate substituted benylamines and/or dibenzylamine.

Use of the oximes and phenols in some instances is desirable because some specific polyisocyanates blocked with these oximes or phenols uncap at relatively low temperatures.

Examples of suitable CH-acidic ketones are given in WO 04/058849 and incorporated herein by reference. Preferred are cyclopentanon-2-carboxymethylester, cyclopentanon-2-carboxyethylester, cyclopentanon-2-carboxynitrile, cyclohexanon-2-carboxymethylester, cyclohexanon-2-carboxyethylester, cyclopentanon-2-carbonylmethane, especially cyclopentanon-2-carboxymethylester, cyclopentanon-2-carboxyethylester, cyclohexanon-2-carboxymethylester and cyclohexanon-2-carboxyethylester, in particular cyclopentanon-2-carboxyethylester and cyclohexanon-2-carboxyethylester.

The compounds of the formula (I), (II) and (III) of the present invention are for example also suitable as photolatent bases in formulations as described in WO 01/92362, the disclosure of which herein is incorporated by reference.

The compositions contain the photoinitiator, component (A), in an amount, for example, of from 0.01 to 20% by weight, preferably from 0.01 to 10% by weight, based on component (B).

Component (B) may also comprise compounds which are converted into a different form by exposure to bases. These are, for example, compounds which under base catalysis alter their solubility in suitable solvents, by elimination of protective groups, for example. Examples are chemically amplified photoresist formulations which react under base catalysis, as described, for example, by Leung in Polym. Mat. Sci. Eng. 1993, 68, 30.

Further examples of suitable components (B) which are converted into a different form under base catalysis are given later on below in connection with the description of photoresist applications.

In addition to the photoinitiator, component (A), the photopolymerizable mixtures may include various additives. Examples of these are thermal inhibitors which are intended to prevent premature polymerization, such as hydroquinone, hydroquinone derivatives, para-hydroxytempo, p-methoxyphenol, β-naphthol or sterically hindered phenols such as 2,6-di(tert-butyl)-p-cresol, for example. To increase the dark storage stability it is possible, for example, to use copper compounds, such as copper naphthenate, stearate or octoate, phosphorus compounds, such as triphenylphosphine, tributylphosphine, triethyl phosphite, triphenyl phosphite or tribenzyl phosphite, quaternary ammonium compounds, such as tetramethylammonium chloride or trimethylbenzylammonium chloride, or hydroxylamine derivatives, such as N-diethyl-hydroxylamine or the ammonium or aluminium salt of N-nitrosophenylhydroxylamine, e.g. cupferron. To exclude atmospheric oxygen during polymerization it is possible to add paraffin or similar waxlike substances, which owing to their lack of solubility in the polymer migrate to the surface at the beginning of polymerization where they form a transparent surface layer which prevents the ingress of air. It is likewise possible to apply an oxygen-impermeable layer. Light stabilizers which can be added, in a small amount, are UV absorbers such as those, for example, of the hydroxyphenylbenzotriazole, hydroxy-phenylbenzophenone, oxalamide or hydroxyphenyl-s-triazine type. Individual compounds or mixtures of these compounds can be used, with or without the employment of sterically hindered amines (HALS).

Examples of such UV absorbers and light stabilisers are disclosed in WO 04/074328, page 12, line 9 to page 14, line 23, said disclosure hereby is incorporated by reference.

Examples of further additives are: Fillers and reinforcing agents, for example calcium carbonate, silicates, glass fibres, glass beads, asbestos, talc, kaolin, mica, barium sulfate, metal oxides and hydroxides, carbon black, graphite, wood flour and flours or fibres of other natural products, synthetic fibres.

Other additives, for example plasticizers, lubricants, emulsifiers, pigments, rheological additives, catalysts, levelling assistants, optical brighteners, flameproofing agents, antistatics, blowing agents.

As stated above, examples of further additives are pigments. Said pigments may be organic or inorganic and are, for example, from the 1-aminoanthraquinone, anthanthrone, anthrapyrimidine, azo, azomethine, quinacridone, quinacridonequinone, quinophthalone, dioxazine, diketopyrrolopyrrole, flavanthrone, indanthrone, isoindoline, isoindolinone, isoviolanthrone, perinone, perylene, phthalocyanine, pyranthrone or thioindigo series, including those, where applicable, in the form of metal complexes or lakes. Azos may be, for example, mono- or disazo pigments from any known sub-class, obtainable, for example, by coupling, condensation or lake formation.

By way of example, examples of organic pigments include Colour Index Pigment Yellow 3, 12, 13, 14, 17, 24, 34, 42, 53, 62, 74, 83, 93, 95, 108, 109, 110, 111, 119, 123, 128, 129, 139, 147, 150, 164, 168, 173, 174, 184, 188, 191, 191:1, 193, 199, Pigment Orange 5, 13, 16, 34, 40, 43, 48, 49, 51, 61, 64, 71, 73, Pigment Red 2, 4, 5, 23, 48:1, 48:2, 48:3, 48:4, 52:2, 53:1, 57, 57:1, 88, 89, 101, 104, 112, 122, 144, 146, 149, 166, 168, 177, 178, 179, 181, 184, 190, 192, 194, 202, 204, 206, 207, 209, 214, 216, 220, 221, 222, 224, 226, 254, 255, 262, 264, 270, 272, Pigment Brown 23, 24, 33, 42, 43, 44, Pigment Violet 19, 23, 29, 31, 37, 42, Pigment Blue 15, 15:1, 15:2, 15:3, 15:4, 15:6, 16, 28, 29, 60, 64, 66, Pigment Green 7, 17, 36, 37, 50, Pigment White 6, Pigment Black 7, 12, 27, 30, 31, 32, Vat Red 74, 3,6-di(3'-cyanophenyl)-2,5-dihydro-pyrrolo[3,4-c]pyrrole-1,4-dione or 3-phenyl-6-(4'-tert-butyl-phenyl)-2,5-dihydro-pyrrolo[3,4-c]pyrrole-1,4-dione.

Preference is given to azobenzimidazolone, disazo and polycyclic pigments and also to isoindolinones and diketopyrrolopyrroles.

Special preference is given to the pigment being a quinacridone, dioxazine, perylene, diketopyrrolopyrrole or disazo condensation pigment. Quinacridones are preferably prepared by oxidation of dihydroquinacridones using hydrogen peroxide, as described, for example, in U.S. Pat. No. 5,840,901 or WO-02/077104.

The pigments may be single chemical compounds or mixtures of a plurality of components, including solid solutions or mixed crystals containing a plurality of chemical compounds. Preference is given to uniformly crystalline pigments as they usually yield greater colour saturation than physical mixtures and mixed phases. If duller shades are nevertheless desired in the final application, this may be achieved by toning down with colorants of different colour in a manner known per se.

In addition to the additives indicated above it is also possible for additional coinitiators or sensitizers to be present. In general these are aromatic ketones or dyes which improve the overall quantum yield by means, for example, of energy transfer or electron transfer. Examples of suitable dyes which can be added as coinitiators are triarylmethanes, for example malachite green, indolines, thiazines, for example methylene blue, xanthones, thioxanthones, oxazines, acridines or phenazines, for example safranine, and rhodamines of the formula

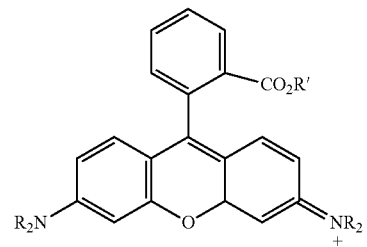

in which R is alkyl or aryl and R' is hydrogen or an alkyl or aryl radical, for example Rhodamine B, Rhodamine 6G or Violamine R, and also Sulforhodamine B or Sulforhodamine G. Likewise suitable are fluorones such as, for example, 5,7-diiodo-3-butoxy-6-fluorone.

The invention further provides a composition as described above comprising in addition to components (A) and (B) a sensitizer (C).

Preferred components (C) are aromatic ketones, such as substituted or unsubstituted benzophenones, thioxanthone, anthraquinone, or dyes such as oxazines, acridines, phenazines and rhodamines and corresponding derivatives.

Likewise suitable in this context are combinations of dyes with borates, as are described, for example, in U.S. Pat. No. 4,772,530, GB 2 307 474, GB 2 307 473, GB 2 307 472 and EP 775 706.

Particular preference is given to substituted benzophenones or thioxanthones. Examples of suitable benzophenones are benzophenone, 4,4'-bis(dimethylamino)benzophenone, 4,4'-bis-(diethylamino)benzophenone, 4,4'-bis(ethylmethylamino)benzophenone, 4,4'-diphenylbenzophenone, 4,4'-diphenoxybenzophenone, 4,4'-bis(p-isopropylphenoxy)benzophenone, 4-methylbenzophenone, 2,4,6-trimethylbenzophenone, 4-phenylbenzophenone, 2-methoxycar-bonylbenzophenone, 4-benzoyl-4'-methyldiphenyl sulfide, 4-methoxy-3,3'-methylbenzophenone, isopropylthioxanthone, chlorothioxanthone, 1-chloro-4-propoxythioxanthone, 2,4-dimethylthioxanthone, 2,4-diethylthioxanthone, 1,3-dimethyl-2-(2-ethylhexyloxy) thioxanthone. Likewise preferred are mixtures of benzophenones and/or thioxanthones such as, for exam-pie, a mixture of benzophenone and 4-methylbenzophenone or of 4-methylbenzophenone and 2,4,6-trimethylbenzophenone.

Further examples of such photosensitizers (C), which can be used either individually or as a mixture, are 1. Thioxanthones Thioxanthone, 2-isopropylthioxanthone, 3-isopropylthioxanthone, 2-chlorothioxanthone, 3-chlorothioxanthone, 2-dodecylthioxanthone, 2,4-diethylthioxanthone, 2,4-dimethylthioxanthone, 1-methoxycarbonylthioxanthone, 2-ethoxycarbonylthioxanthone, 3-(2-methoxyeth-oxycarbonyl)thioxanthone, 4-butoxycarbonylthioxanthone, 3-butoxycarbonyl-7-methylthio-xanthone, 1-cyano-3-chlorothioxanthone, 1-ethoxycarbonyl-3-chlorothioxanthone, 1-ethoxycarbonyl-3-ethoxythioxanthone, 1-ethoxycarbonyl-3-aminothioxanthone, 1-ethoxycarbonyl-3-phenylsulfuryl-thioxanthone, 3,4-di-[2-(2-methoxyethoxy)ethoxycarbonyl] thioxanthone, 1-ethoxycarbonyl-3-(1-methyl-1-morpholinoethyl)thioxanthone, 2-methyl-6-dimethoxymethylthio-xanthone, 2-methyl-6-(1,1-dimethoxybenzyl)thioxanthone, 2-morpholinomethylthioxanthone, 2-methyl-6-morpholinomethylthioxanthone, N-allylthioxanthone-3,4-dicarboximide, N-octyl-thioxanthone-3,4-dicarboximide, N-(1,1,3,3-tetramethylbutyl)thioxanthone-3,4-dicarboximide, 1-phenoxythioxanthone, 6-ethoxycarbonyl-2-methoxythioxanthone, 6-ethoxycarbonyl-2-me-thylthioxanthone, thioxanthone 2-polyethylene glycol esters, 2-hydroxy-3-(3,4-dimethyl-9-oxo-9H-thioxanthon-2-yloxy)-N, N, N-trimethyl-1-propanaminium chloride;

2. Benzophenone and benzophenone derivatives

Benzophenone, 4-phenylbenzophenone, 4-methoxybenzophenone, 4,4'-dimethoxybenzo-phenone, 4,4'-dimethylbenzophenone, 4,4'-dichlorobenzophenone, 4,4'-dimethylaminoben-zophenone, 4,4'-diethylaminobenzophenone, 4-methylbenzophenone, 2,4,6-trimethylbenzophenone, 4-(4-methylthiophenyl)benzophenone, 3,3'-dimethyl-4-methoxybenzophenone, methyl-2-benzoylbenzoate, 4-(2-hydroxyethylthio)benzophenone, 4-(4-tolylthio)benzophenone, 4-benzoyl-N, N, N-trimethylbenzenemethanaminium chloride, 2-hydroxy-3-(4-benzoylphen-oxy)-N,N,N-trimethyl-1-propanaminium chloride monohydrate, 4-(13-acryloyl-1,4,7,10,13-pentaoxatridecyl)benzophenone, 4-benzoyl-N, N-dimethyl-N-[2-(1-oxo-2-propenyl)-oxy] ethylbenzenemethanaminium chloride; [4-(2-hydroxy-ethylsulfanyl)-phenyl]-(4-isopropyl-phenyl)-methanone; biphenyl-[4-(2-hydroxy-ethylsulfanyl)-phenyl]-methanone; biphenyl-4-yl-phenyl-methanone; biphenyl-4-yl-p-tolyl-methanone; biphenyl-4-yl-m-tolyl-methanone; [4-(2-hydroxy-ethylsulfanyl)-phenyl]-p-tolyl-methanone; [4-(2-hydroxy-ethylsulfanyl)-phenyl]-(4-isopropyl-phenyl)-methanone; [4-(2-hydroxy-ethylsulfanyl)-phenyl]-(4-methoxy-phenyl)-methanone; 1-(4-benzoyl-phenoxy)-propan-2-one; [4-(2-hydroxy-ethylsulfanyl)-phenyl]-(4-phenoxy-phenyl)-methanone; 3-(4-benzoyl-phenyl)-2-dimethylamino-2-methyl-1-phenyl-propan-1-one; (4-chloro-phenyl)-(4-octylsulfanyl-phenyl)-methanone; (4-chloro-phenyl)-(4-dodecylsulfanyl-phenyl)-methanone; (4-bromo-phenyl)-(4-octylsulfanyl-phenyl)-methanone; (4-dodecylsulfanyl-phenyl)-(4-methoxy-phenyl)-methanone; (4-benzoyl-phenoxy)-acetic acid methyl ester; biphenyl-[4-(2-hydroxy-ethylsulfanyl)-phenyl]-methanone;

3. 3-Acylcoumarins

3-Benzoylcoumarin, 3-benzoyl-7-methoxycoumarin, 3-benzoyl-5,7-di(propoxy)coumarin, 3-benzoyl-6,8-dichlorocoumarin, 3-benzoyl-6-chlorocoumarin, 3,3'-carbonylbis[5,7-di(prop-oxy)coumarin], 3,3'-carbonylbis(7-methoxy-coumarin), 3,3'-carbonylbis(7-diethylaminocoumarin), 3-isobutyroylcoumarin, 3-benzoyl-5,7-dimethoxycoumarin, 3-benzoyl-5,7-diethoxycoumarin, 3-benzoyl-5,7-dibutoxy-coumarin, 3-benzoyl-5,7-di(methoxyethoxy)coumarin, 3-benzoyl-5,7-di(allyloxy)coumarin, 3-benzoyl-7-dimethyl-aminocoumarin, 3-benzoyl-7-diethylamino-coumarin, 3-isobutyroyl-7-dimethylaminocoumarin, 5,7-dimethoxy-3-(1-naphthoyl)coumarin, 5,7-dimethoxy-3-(1-naphthoyl) coumarin, 3-benzoylbenzo[f]coumarin, 7-diethylamino-3-thienoylcoumarin, 3-(4-cyanobenzoyl)-5,7-dimethoxycoumarin;

4. 3-(Aroylmethylene)thiazolines

3-Methyl-2-benzoylmethylene-β-naphthothiazoline, 3-methyl-2-benzoylmethylenebenzothiazoline, 3-ethyl-2-propionylmethylene-β-naphthothiazoline;

5. Other carbonyl compounds

Acetophenone, 3-methoxyacetophenone, 4-phenylacetophenone, benzil, 2-acetylnaphthalene, 2-naphthaldehyde, 9,10-anthraquinone, 9-fluorenone, dibenzosuberone, xanthone, 2,5-bis(4-diethylaminobenzylidene)cyclopentanone, α-(para-dimethylaminobenzylidene) ketones, such as 2-(4-dimethylaminobenzylidene)indan-1-one or 3-(4-dimethylaminophenyl)-1-indan-5-yl-propenone, 3-phenylthiophthalimide, N-methyl-3,5-di(ethylthio)phthalimide.

It is evident, that the photolatent base compounds of the formula (I), (II) and (III) optionally also are used in combination with other known photolatent base compounds [as further additive (C)]. Such compounds are for example described in WO 97/31033, WO 98732756, WO 98/38195, WO 98/41524, EP 898202, WO 00/10964 and WO 03/33500. In particular combinations of the compounds of formula (I), (II) or (III) with α-aminoketones, such as for example (4-morpholino-benzoyl)-1-(4-methylbenzyl)-1-dimethylamino propane, (4-morpholino-benzoyl)-1-benzyl-1-dimethylamino propane or 2-benzyl-2-dimethylamino-1-(3,4-dimethoxyphenyl) butanone-1 or with

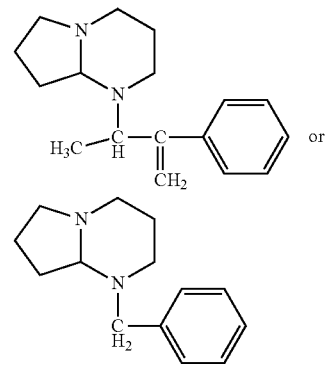

are of interest.

In addition to the above-described base-catalysable (curable) binders, component (B), the composition may also include other binders as well. Further olefinically unsaturated compounds, for example, are possible. The unsaturated compounds may include one or more olefinically double bonds. They may be of low molecular mass (monomeric) or higher molecular mass (oligomeric). Examples of monomers having a double bond are alkyl or hydroxyalkyl acrylates or methacrylates, such as methyl, ethyl, butyl, 2-ethylhexyl or 2-hydroxyethyl acrylate, isobornyl acrylate, methyl methacrylate or ethyl methacrylate. Silicone acrylates are also of interest. Further examples are acrylonitrile, acrylamide, methacrylamide, N-substituted (meth)acrylamides, vinyl esters such as vinyl acetate, vinyl ethers such as isobutyl vinyl ether, styrene, alkyl- and halostyrenes, N-vinylpyrrolidone, vinyl chloride or vinylidene chloride.

Examples of monomers having two or more double bonds are the diacrylates of ethylene glycol, propylene glycol, neopentyl glycol, hexamethylene glycol or bisphenol A, 4,4'-bis-(2-acryloyloxyethoxy)diphenylpropane, trimethylolpropane triacrylate, pentaerythritol triacrylate or tetraacrylate, vinyl acrylate, divinyl benzene, divinyl succinate, diallyl phthalate, triallyl phosphate, triallyl isocyanurate or tris(2-acryloylethyl) isocyanurate.

Examples of polyunsaturated compounds of relatively high molecular mass (oligomers) are acrylated epoxy resins, acrylated polyesters or polyesters containing vinyl ether groups or epoxy groups, polyurethanes and polyethers. Further examples of unsaturated oligomers are unsaturated polyester resins which are mostly prepared from maleic acid, phthalic acid and one or more diols and have molecular weights of from about 500 to 3000. In addition it is also possible to employ vinyl ether monomers and oligomers, and also maleate-terminated oligomers with polyester, polyurethane, polyether, polyvinyl ether and epoxy main chains. In particular, combinations of vinyl ether-functional oligomers and polymers as are described in WO 90/01512 are very suitable. Also suitable, however, are copolymers of vinyl ether and maleic acid functionalized monomers. Unsaturated oligomers of this kind can also be referred to as prepolymers.

It is evident, that also monomers or oligomers which have more than one specific functionalization in the molecule are suitable in the compositions according to the invention, for example an oligomer bearing an acrylate function and an isocyanate as well. Any other combinations of functionalities is also considered as part of the composition according to the invention. Such "multi"-functionalized compounds may for example be used instead of or in addition to a "single" functionalized compound or a mixture of "single" functionalized compounds.

Particularly suitable examples are esters of ethylenically unsaturated carboxylic acids and polyols or polyepoxides, and polymers having ethylenically unsaturated groups in the chain or in side groups, such as unsaturated polyesters, polyamides and polyurethanes and copolymers thereof, alkyd resins, polybutadiene and butadiene copolymers, polyisoprene and isoprene copolymers, polymers and copolymers having (meth)acrylic groups in side chains, and mixtures of one or more such polymers.

If, in addition, use is made of such free-radically curable monomers, oligomers/polymers then it is judicious to add a further photoinitiator which dissociates into free radicals. Such photoinitiators are known and are produced industrially. Examples are benzophenone, benzophenone derivatives, for example those as mentioned above as suitable sensitzers, ketal compounds, as for example benzildimethylketal (IRGACURE® 651); acetophenone, acetophenone derivatives, for example α-hydroxycycloalkyl phenyl ketones, such as for example 1-hydroxy-cyclohexyl-phenyl-ketone (IRGACURE® 184), 2-hydroxy-2-methyl-1-phenyl-propan-one (DAROCUR® 1173), 1-(4-dodecylbenzoyl)-1-hydroxy-1-methyl-ethane, 1-(4-isopropyl-benzoyl)-1-hydroxy-1-methyl-ethane, 1-[4-(2-hydroxyethoxy)-phenyl]-2-hydroxy-2-methyl-1-propan-1-one (IRGACURE®2959); 2-hydroxy-1-{4-[4-(2-hydroxy-2-methyl-propionyl)-benzyl]-phenyl}-2-methyl-propan-1-one (IRGACURE®127); 2-hydroxy-1-{4-[4-(2-hydroxy-2-methyl-propionyl)-phenoxy]-phenyl}-2-methyl-propan-1-one, dialkoxyacetophenones, α-aminoacetophenones, e.g. (4-methylthio-benzoyl)-1-methyl-1-morpholinoethane (IRGACURE® 907), (4-morpholinobenzoyl)-1-benzyl-1-dimethylamino-propane (IRGACURE® 369), (4-morpholinobenzoyl)-1-(4-methylbenzyl)-1-dimethylaminopropane (IRGACURE® 379), (4-(2-hydroxy-ethyl)aminobenzoyl)-1-benzyl-1-dimethylaminopropane), (3,4-dimethoxybenzoyl)-1-benzyl-1-dimethylaminopropane; 4-aroyl-1,3-dioxolanes, benzoin alkyl ethers and benzil ketals, such as benzil dimethyl ketal, phenylglyoxalates and derivatives thereof, e.g. oxo-phenyl-acetic acid 2-(2-hydroxy-ethoxy)-ethyl ester, dimeric phenylglyoxalic esters, e.g. oxo-phenyl-acetic acid 1-methyl-2-[2-(2-oxo-2-phenyl-acetoxy)-propoxy]-ethyl ester (IRGACURE® 754); mono-acylphosphine oxides, such as (2,4,6-trimethylbenzoyl)diphenylphosphine oxide (DAROCUR® TPO) bisacylphosphine oxides, such as bis(2,6-dimethoxybenzoyl)(2,4,4-trimethylpent-1-yl)phosphine oxide, bis(2,4,6-trimethylbenzoyl)phenylphosphine oxide (IRGACURE® 819) or bis(2,4,6-trimethylbenzoyl)(2,4-dipentoxyphenyl)phosphine oxide, trisacylphosphine oxides, oxime esters, e.g. 1,2-octanedione 1-[4-(phenylthio)phenyl]-2-(O-benzoyloxime) (IRGACURE® OXE01), ethanone 1-[9-ethyl-6-(2-methyl benzoyl)-9H-carbazol-3-yl]-1-(O-acetyloxime) (IRGACURE® OXE02), 9H-thioxanthene-2-carboxaldehyde 9-oxo-2-(O-acetyloxime), peresters, e.g. benzophenone tetracarboxylic peresters as described for example in EP 126541, ferrocenium compounds or titanocenes, such as dicyclopentadienylbis(2,6-difluoro-3-pyrrolophenyl)titanium, for example.

Examples are specified in EP-A-284 561. Polymer systems of this kind, in which curing/crosslinking takes place by different mechanisms, are also referred to as hybrid systems. The DAROCUR® and IRGACURE® compounds are available from Ciba Specialty Chemicals.

The compositions of the invention can also have added to them non-reactive binders, which is particularly judicious if the photopolymerizable compounds are liquid or viscous substances. The amount of the non-reactive binder can be, for example, 5-95%, preferably 10-90% and, in particular, 40-90% by weight, based on the overall solids content. The choice of non-reactive binder is made in accordance with the field of use and with the properties required for this use, such as the possibility for development in aqueous and organic solvent systems, adhesion to substrates, and sensitivity to oxygen.

Examples of suitable binders are polymers having a molecular weight of around 5000-2,000,000, preferably 10,000-1,000,000. Examples are: homo- and copolymeric acrylates and methacrylates, for example copolymers of methyl methacrylate/ethyl acrylate/methacrylic acid, poly (alkyl methacrylates), poly(alkyl acrylates); cellulose esters and ethers, such as cellulose acetate, cellulose acetate butyrate, methylcellulose, ethylcellulose; polyvinylbutyral, polyvinylformal, cyclized rubber, polyethers such as polyethylene oxide, polypropylene oxide, polytetrahydrofuran; polystyrene, polycarbonate, polyurethane, chlorinated polyolefins, polyvinyl chloride, copolymers of vinyl chloride/vinylidene chloride, copolymers of vinylidene chloride with acrylonitrile, methyl methacrylate and vinyl acetate, polyvinyl acetate, copoly(ethylene/vinyl acetate), polymers such as polycaprolactam and poly(hexamethylene adipamide) and polyesters such as poly(ethylene glycol terephtalate) and poly(hexamethylene glycol succinate).

The invention additionally provides a process for carrying out base-catalysed reactions which comprises subjecting a composition as described above to irradiation with light having a wavelength of from 200 nm to 650 nm.

In some cases it may be advantageous to carry out heating prior to, during or after exposure to light. In this way it is possible in many cases to accelerate the crosslinking reaction.

It is evident, that heating of the formulation prior to the exposure to light may also be appropriate, in particular for example in case of hot melt (adhesive) systems, where the composition is molten for coating of the substrate and afterwards is cured. In other words, here the heating is not preformed in order to accelerate the curing, but for application of the formulation to the substrate.

Also in accordance with the invention is the use of a photolatent base compound of the formula (I), (II) or (III) as described above as a photoinitiator for photochemically induced, base-catalysed polymerization, addition or substitution reactions; as well as the use of said compounds for preparing coatings, adhesives, inks, moulding compounds or photostructured layers, and the process described above for preparing coatings, adhesives, inks, moulding compounds or photostructured layers.

The invention additionally provides a coated substrate coated on at least one surface with a composition as described above, and also a process for photographically producing relief images, in which a coated substrate is subjected to imagewise exposure and then the unexposed portions are removed with a solvent. Of particular interest here is the abovementioned exposure to light by means of a laser beam.

A further subject of the invention is a polymerized or crosslinked composition as described above.

The sensitivity of the novel compositions to light generally extends from about 200 nm through the UV region and into the infrared region (about 20,000 nm, in particular 1200 nm) and therefore spans a very broad range. Suitable radiation comprises, for example, sunlight or light from artificial light sources. Therefore, a large number of very different types of light source can be used. Both point sources and flat radiators (lamp carpets) are suitable. Examples are carbon arc lamps, xenon arc lamps, medium-pressure, high-pressure and low-pressure mercury lamps, doped if desired with metal halides (metal halogen lamps), micro-wave-stimulated metal vapour lamps, excimer lamps, superactinic fluorescent tubes, fluorescent lamps, incandescent argon lamps, electronic flashlights, xenon flashlights, photographic flood lamps, light emitting diodes (LED), organic light emitting diodes (OLED), electron beams and X-rays, produced by means of synchrotrons or laser plasma. The distance between the lamp and the substrate according to the invention which is to be exposed can vary depending on the application and on the type and/or power of the lamp, for example between 2 cm and 150 cm. Also especially suitable are laser light sources, for example excimer lasers. Lasers in the visible region or in the IR region can also be employed. Very advantageous here is the high sensitivity of the novel materials and the possibility of adapting the absorption wavelength to the laser line by using a dye as coinitiator. By this method it is possible to produce printed circuits in the electronics industry, lithographic offset printing plates or relief printing plates, and also photographic image recording materials.

Curing may further be effected by exposing the composition comprising the photolatent bases according to the invention to a corona discharge or to a plasma, for example a plasma provided by a discharge in an arc or in a plasma chamber.

Depending on the light source used it is advantageous in many cases to employ a sensitizer, as described above, whose absorption spectrum coincides as closely as possible to the emission spectrum of the radiation source.

The compositions of the invention can be employed for various purposes, for example as printing inks, such as for example flexo-printing inks or inks for sheet-fed printing, as clear-coats, as white paints, for example for wood or metal, as coating materials, inter alia for paper, wood, metal or plastic, as powder coatings, as daylight-curable exterior coatings for marking buildings and roads, for photographic reproduction processes, for holographic recording materials, for image recording processes or for the production of printing plates which can be developed using organic solvents or aqueous-alkaline media, for the production of masks for screen printing, as dental filling materials, as adhesives, including pressure-sensitive adhesives, as laminating resins, as etch resists or permanent resists and as solder masks for electronic circuits, for the production of three-dimensional articles by mass curing (UV curing in transparent moulds) or by the stereolithography process, as is described, for example, in U.S. Pat. No. 4,575,330, for the preparation of composite materials (for example styrenic polyesters, which may contain glass fibres and/or other fibres and other assistants) and other thick-layer compositions, for the coating or encapsulation of electronic components, or as coatings for optical fibres.

Of particular interest is the use of the compositions of the invention for preparing decorative coatings, such as exterior coatings on substrates of all kinds, for example buildings, fences, chipboard panels, and as a coating on stone, concrete or metal, for the coating of vehicles, for example, such as cars, railways or aircraft. The compositions may likewise be used in automotive OEM finishing and automotive refinishing, and also for the finishing of car bodies, plastic parts for cars and body-mounted car parts. The initiators of the invention can be used in a multicoat system in the surfacer, base coat or clearcoat. Their use in pigmented topcoats is also possible.

In surface coatings, it is common to use mixtures of a prepolymer with polyunsaturated monomers which also contain a monounsaturated monomer. The prepolymer here is primarily responsible for the properties of the coating film, and varying it allows the skilled worker to influence the properties of the cured film. The polyunsaturated monomer functions as a crosslinker, which renders the coating film insoluble. The monounsaturated monomer functions as a reactive diluent, by means of which the viscosity is reduced without the need to use a solvent.

The photocurable compositions of the invention are suitable, for example, as coating materials for substrates of all kinds, examples being wood, textiles, paper, ceramic, glass, plastics such as polyesters, polyethylene terephthalate, polyolefins or cellulose acetate, especially in the form of films, and also metals such as Al, Cu, Ni, Fe, Zn, Mg or Co and GaAs, Si or $SiO_2$, on which it is the intention to apply a protective coating or, by imagewise exposure, an image.

The substrates can be coated by applying a liquid composition, a solution or suspension to the substrate. The choice of solvent and the concentration depend predominantly on the type of composition and the coating process. The solvent should be inert: in other words, it should not undergo any chemical reaction with the components and should be capable of being removed again after the coating operation, in the drying process. Examples of suitable solvents are ketones, ethers and esters, such as methyl ethyl ketone, isobutyl methyl ketone, cyclopentanone, cyclohexanone, N-methylpyrrolidone, dioxane, tetrahydrofuran, 2-methoxyethanol, 2-ethoxyethanol, 1-methoxy-2-propanol, 1,2-dimethoxyethane, ethyl acetate, n-butyl acetate and ethyl 3-ethoxypropionate.

Using known coating processes, the solution is applied uniformly to a substrate, for example by spin coating, dip coating, knife coating, curtain coating, brushing, spraying—especially electrostatic spraying—and reverse roll coating and by electrophoretic deposition. It is also possible to apply the photosensitive layer to a temporary, flexible support and then to coat the final substrate, for example a copper-clad circuit board, by means of layer transfer via lamination.

The amount applied (layer thickness) and the nature of the substrate (layer support) are functions of the desired field of application. The range of layer thicknesses generally comprises values from about 0.1 µm to more than 100 µm.

The radiation-sensitive compositions of the invention can also be subjected to imagewise exposure. In this case they are used as negative resists. They are suitable for electronics (galvanoresists, etch resists and solder resists), for the production of printing plates, such as offset printing plates, flexographic and relief printing plates or screen printing plates, for the production of marking stamps, and can be used for chemical milling or as microresists in the production of integrated circuits. There is a correspondingly wide range of variation in the possible layer supports and in the processing conditions of the coated substrates.

Where the radiation-sensitive compositions of the invention are resins which are converted from a water-insoluble form into a water-soluble form under the influence of the photochemically liberated amine, they can be used as positive resists on imagewise exposure to light. Examples of such resins are polystyrene resins containing benzisoxazol and phenol groups, as described by Niu et al. in J. Polym. Mater. Sci. Eng. (1996), 75, 427, or polyhydroxystyrene resins some or all of whose hydroxyl groups have been protected by carbonate groups which can be eliminated under base catalysis, as described, for example, by Urankar et al. in Macromolecules (1997), 30, 1304.

The term "imagewise" exposure relates both to exposure through a photomask containing a predetermined pattern, for example a slide, exposure by a laser beam which is moved under computer control, for example, over the surface of the coated substrate and so generates an image, and irradiation with computer-controlled electron beams.

Following the imagewise exposure of the material and prior to developing, it may be advantageous to carry out a brief thermal treatment, in which only the exposed parts are thermally cured. The temperatures employed are generally 50-150° C. and preferably 80-130° C.; the du-ration of the thermal treatment is generally between 0.25 and 10 minutes.

A further field of use for photocuring is that of metal coating, for example the surface-coating of metal panels and tubes, cans or bottle tops, and photocuring on polymer coatings, for example of floor or wall coverings based on PVC.

Examples of the photocuring of paper coatings are the colourless varnishing of labels, record sleeves or book covers.

The use of the compounds of the invention for curing shaped articles made from composite compositions is likewise of interest. The composite composition is made up of a self-supporting matrix material, for example a glass-fibre fabric, or else, for example, of plant fibres [cf. K.-P. Mieck, T. Reussmann in Kunststoffe 85 (1995), 366-370], which is impregnated with the photocuring formulation. Shaped articles which are produced from composite compositions using the compounds according to the invention are of high mechanical stability and resistance. The compounds of the invention can also be used as photocuring agents in moulding, impregnating and coating compositions, as are described, for example, in EP-A-7086. Examples of such compositions are fine coating resins on which stringent requirements are placed with respect to their curing activity and resistance to yellowing, or fibre-reinforced mouldings such as planar or longitudinally or transversely corrugated light diffusing panels.

The novel compounds of the formula (I), (II) and (III) are also suitable in applications as described in WO 2005/100482, the disclosure of which hereby is incorporated by reference. Described are compositions based on siloxanes terminated polymers, which are hardened by radiation and humidity, in particular a curable composition comprising
  (i) at least one silyl-terminated polymer and
  (ii) at least one photolatent base,
wherein the silyl-terminated polymer consists of a linear or branched base-polymer without silane groups, which base-polymer is end-capped by silane groups.

The compounds of the formula (I), (II) and (III) of the present invention are suitable as photolatent base compound, that is component (ii), in the above described composition.

The compositions according to the present invention are also useful in hot-melt adhesives, which are heated to be applied to a substrate and then crosslinked via exposure to irradiation. In such composition for example isocyanate compositions, in particular blocked isocyanates as described above are employed. Accordingly, for example, the pre-polymerized adhesives containing isocyanate and the reactive groups protected or not can for example be processed at high temperature and coated onto the substrate following the hotmelt process, afterwards full cure is achieved by an additional curing step involving the reactive groups, which is realized by photoactivation of the photolatent catalyst.

Hotmelt adhesives are interesting as pressure sensitive adhesives (PSA) and suitable to re-place the use of solvent based compositions, which from an environmental point of view are un wanted. The hotmelt extrusion process in order to achieve the high flow viscosity necessitates high application temperatures. The compositions of the present invention comprising reactive groups are suitable as crosslinkers in the preparation of a hotmelt coating, where the crosslinkers enter into a chemical reaction with the functional comonomers of the (meth)acrylate PSA. After the coating operation, the PSAs are first crosslinked thermally, or, implementing the dual crosslinking mechanism, the PSA is subsequently crosslinked with UV light. UV crosslinking irradiation, for example takes place by means of shortwave ultraviolet radiation in a wavelength range from 200 to 400 nm, depending on the photolatent bases and/or sensitizer. Such systems and processes are for example described in US 2006/0052472.

The photolatent bases of the present invention also are suitable in redox-curable formulations as for example described in EP Application No. 08150721.2 of Jan. 28, 2008.

Such formulations comprise
  (a) at least a photolatent base compound of the formula (I), (II) or (III) as defined above; and
  (b) a radically polymerizable compound; and
  (c) a free radical initiator capable to be reduced by amines and/or amidines, in particular a peroxide, and optionally,
  (d) an initiator which is capable of curing (b), in particular a radical photoinitiator. Compositions according to the present invention are also suitable in UV-curable adhesives.

Such UV-curable adhesives are preferably OH/NCO or SH/NCO systems as described above in blocked or unblocked form. These adhesives are produced by the condensation reaction of an organic polyisocyanate with an active hydrogen-containing compound.

The isocyanate compound is for example any aromatic, aliphatic, cycloaliphatic, acryl aliphatic, or heterocyclic isocyanate or polyisocyanate, and the prepolymers or mixtures thereof.

The term "polyisocyanates", as already mentioned above, includes diisocyanates, triisocyanates, tetraisocyanates, etc., and mixtures thereof. Suitable isocyanate compounds are commercially available from Bayer under the name Desmodur® or from Rhodia under the trade name Tolonate®.

The active hydrogen containing compound in the adhesive has functional groups which are for example selected from the group consisting of COOH, OH, $NH_2$, NH, $CONH_2$, —SH, and CONH. Preferably the active hydrogen containing compound is OH or SH resulting in OH/NCO and SH/NCO resins.

OH/NCO systems are known as polyurethane adhesives. Polyurethane adhesives usually are one-component polyurethane adhesives (1K PU adhesives) or two-component polyurethane adhesives (1K PU adhesives) and one- or two-pack isocyanate free polyurethane adhesives (e.g. blocked isocyanates).

Polyester polyols and polyether polyols preferably used as active hydrogen containing compound in OH/NCO resins are commercially available materials. Suitable polyesterpolyols are commercially available, for example under the trade name Desmophen® and Baycoll®.

Multifunctional aliphatic amine chain extender may be present and include ethylene diamine, 1,4-butanediamine, isophorene diamine, triethylenetetraamine, and triethylene oxide diamine. Furthermore desiccants may be present such as Baylith L.

Suitable thiol group containing compounds are those as described in WO 01/92362 or the ones as given above. As disclosed therein the most preferred thiol-functional compounds are pentaerythritol tetrakis (3-mercaptopropionate) and 3-mercaptopropionate.

The adhesive composition optionally also contains other additive compounds customary in the art, for example, antioxidants such as for example sterically hindered amines (HALS), phosphites or phenolic antioxidants, filler resins, thickeners, fluidity adjusting agents, plasticizers, defoaming agents and the like.

Exposure of the adhesive is for example carried out prior to or after the lamination. Exposure after the lamination may result in faster curing. Exposure prior to the lamination, for example allows the use of opaque substrates. Furthermore, the diamine catalyst usually present in OH/NCO or SH/NCO systems is for example replaced by the latent base of the formula (I), (II) or (III).

Thus, the photolatent base compounds of the present invention also are suitable in a method of bonding a first substrate to a second substrate, comprising the steps of (i) applying an UV-curable adhesive resin composition comprising a photolatent base of the compound of formula (I), (II) or (III) as described above, to at least one transparent surface of at least one of said first and second substrates, (ii) bringing said first and second substrates together with said adhesive composition there between, (iii) exposing said adhesive composition to actinic radiation to effect curing.

Further, the photo photolatent base compounds of the present invention also are suitable in a method of bonding a first substrate to a second substrate, comprising the steps of (i) applying an UV-curable adhesive resin composition comprising a photolatent base of the compound of formula (I), (II) or (III) as described above, to at least one surface of at least one of said first and second substrates, (iii) exposing said adhesive composition to actinic radiation; and (ii) bringing said first and second substrates together with said adhesive composition there between.

Examples of the method and components employed therein are given in WO 08/009575, the disclosure of which herein is incorporated by reference.

The photolatent base compounds of the present inveniton also are suitable for incorporation in to hotmelt adhesives or plastisols which are usually are processed at elevated temperature (e.g. between 120° C. and 240° C.) prior to use.

The photolatent base compounds of formula (I), (II) and (III) according to the present invention also may be employed in a process wherein a composition of matter, comprising said photolatent base compounds, is subjected to irradiation before being further processed.

Such processes are for example described in WO 06/008251, EP 1002587 and WO 04/069427, the disclosure of said documents hereby is incorporated by reference.

The photolatent base compounds of the present invention are also suitable for curing og thiirane based resins as for example described in EP1564255, the disclosure of which hereby is incorporated by reference.

Such formulations comprise at least one photolatent base compound of the formula (I), (II) or (III) as described above, and at least one episulfide compound having two or more thiirane rings in its molecule, for example a compound

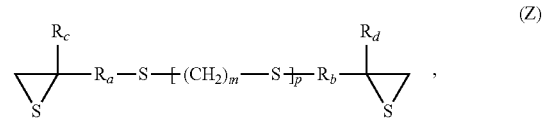

wherein p is an integer from 0-4, m is an integer from 0-6, $R_c$ and $R_d$ independently of each other are hydrogen or a mono-valent $C_1$-$C_{10}$hydrocarbon group and $R_a$ and $R_b$ independently of each other are a divalent $C_1$-$C_{10}$hydrocarbon group. Preferably, (Z) is bis(2,3-epithiopropyl) sulfide or bis(2,3epithiopropyl) disulfide. Such episulfide compound having two or more thiirane rings in its molecule (Z) in the present application accordingly refer to component (B) as given in the composition claims.

A further use of the novel compounds of the formula (I), (II) and (III) according to the present invention resides in UV-dose indicator formulations. The compounds of the present invention are incorporated in said forumations as photolatent bases, which upon irradiation release the base. The base then activates the color formation via a suitable colorant compound, which also is present in the formulation.

Thus, another subject of the invention is a composition comprising (a) a base-responsive colorant;

(b) a photolatent base compound of the formula (I), (II) or (III);

which is in particular suited for the determination of the dose of radiation which has been ab-sorbed by the irradiated coating.

Examples of corresponding UV-dose indicator systems are given in EP Patent Application No. 06119455.1 (Aug. 24, 2006), the disclosure of which herein is incorporated by reference.

The examples which follow illustrate the invention in more detail, without restricting the scope said examples only. Parts and percentages are, as in the remainder of the description and in the claims, by weight, unless stated otherwise. Where alkyl radicals having more than three carbon atoms are referred to in the examples without any mention of specific isomers, the n-isomers are meant in each case.

Example 1 Preparation of 4-(hexahydro-pyrrolo[1,2-a]pyrimidin-1-ylmethyl)-benzoic Acid Methyl Ester

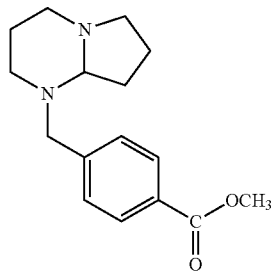 [SMILES: COC(=O)c1ccc(CN2CCCN3CCCC32)cc1]

1.1 Preparation of octahydro-pyrrolo[1,2-a]pyrimidine 600 g of tert-butyl methyl ether and 99.35 g (0.8 mol) of 2,3,4,6,7,8-hexahydro-pyrrolo[1,2-a]pyrimidine (DBN) are placed in a 2.5 l reaction flask and heated to reflux (55° C.). 18.22 g (0.48 mol) of lithium aluminium hydride are added to this solution over two hours. After the addition, the grey suspension is stirred at 55° C. for 30 minutes. The suspension is then cooled down to 5° C. and hydrolyzed by addition of 18 g water, 18 g of a 10% sodium hydroxide solution and another 54 g water under vigorous stirring. The suspension is filtered over a celite filter material (Hyflo Supra Cel® provided by Fluka; No. 56678) and the filter cake is washed with 400 g of tert-butyl methyl ether. The yellow filtrate is dried over $Na_2SO_4$, and concentrated in vacuum. Yield: 66.44 g (66%) of octahydro-pyrrolo[1,2-a]pyrimidine obtained as an orange oil. The structure is confirmed by $^{13}$C-NMR spectroscopy.

1.2 Preparation of 4-(hexahydro-pyrrolo[1,2-a]pyrimidin-1-ylmethyl)-benzoic acid methyl ester 2.3 g (18 mmol) of octahydro-pyrrolo[1,2-a]pyrimidine are added dropwise to a colorless solution of 2.06 g (9 mmol) of methyl 4-(bromomethyl)-benzoate in 30 g toluene while stirring. Stirring is continued for 20 hours at room temperature, giving a white slightly viscous and sticky suspension. The suspension is filtered off, and the filtrate is concentrated in vacuum. 4-(hexahydro-pyrrolo[1,2-a]pyrimidin-1-ylmethyl)-benzoic acid methyl ester is obtained as a white solid with a melting point of 112.4° C.–113.9° C. Yield 1.9 g (77%).

Example 2 Preparation of 4-(hexahydro-pyrrolo[1,2-a]-pyrimidin-1-ylmethyl)-benzoic Acid Butyl Ester

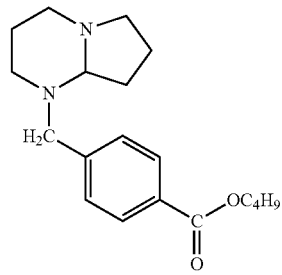

10 g of 1-butanol and 2.1 g (0.0075 mol) of 4-(hexahydro-pyrrolo[1,2-a]pyrimidin-1-ylmethyl)-benzoic acid methyl ester (of example 1) are placed in a flask equipped with a stirrer and distillation equipment. 0.07 g (0.0083 mol) of lithium hydride is subsequently added to this solution. The suspension is heated over a period of an hour to 130° C. (oil bath temperature). At this temperature 1-butanol begins to distill off. When no more alcohol is left, the reaction is cooled to room temperature, diluted with dichloromethane and extracted with water. The organic phase is dried over $K_2CO_3$, and concentrated in vacuum. The slightly yellowish oil crystallizes upon stirring with heptane. The suspension is filtered providing 1.1 g (46%) 4-(hexahydro-pyrrolo[1,2-a]pyrimidin-1-ylmethyl)-benzoic acid butyl ester as a white solid with a melting point of 64-67° C.

Examples 3-6

The compounds of the following examples 3-6 are prepared according to the method described in example 2, except that the alcohols reported in Table 1 are used instead of 1-butanol.

TABLE 1

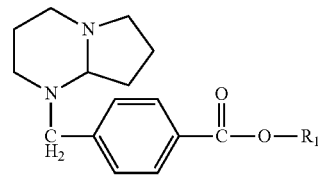

| Ex. | alcohol | $R_1$ | yield | mp [° C.] |
|---|---|---|---|---|
| 3 | 1-hexanol | $C_6H_{13}$ | 54% | 48-50° C. |
| 4 | hexane-1,6-diol | $(CH_2)_6$—OH | 70% | oil |
| 5 | 2-methoxy ethanol | $(CH_2)_2OCH_3$ | 30% | oil |
| 6 | diethyleneglycole monoethylether | $(CH_2)_2$—O—$(CH_2)_2$—$OC_2H_5$ | 25% | oil |

Examples 7-9

The compounds of the following examples 7 and 8 are prepared according to the method as described in example 2, except that the polyols reported in Table 2 are used instead of 1-butanol. Example 9 is obtained under the conditions as set out in example 2, using the compound of example 4 as alcohol starting material.

TABLE 2
| Ex. | alcohol | R₂ | yield | mp [° C.] |
|---|---|---|---|---|
| 7 | ethyleneglycol | CH₂CH₂ | 5% | solid |
| 8 | 1,1,1-tris(hydroxymethyl) propane | —CH₂—C(C₂H₅)(CH₂OH)—CH₂— | 17% | viscous oil |
| 9 | 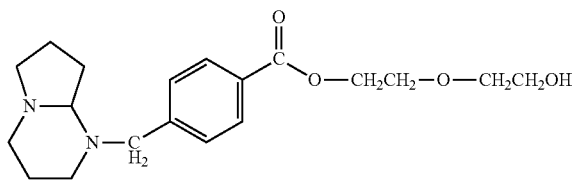 (= compound of ex. 4) | (CH₂)₆ | 15% | solid |
Example 10: 4-(Hexahydro-pyrrolo[1,2-a]pyrimidin-1-ylmethyl)-benzoic acid 2-(2-hydroxy-ethoxy)-ethyl ester and diethyleneglycole di[4-(hexahydro-pyrrolo[1,2-a]pyrimidin-1-ylmethyl)-benzoate]
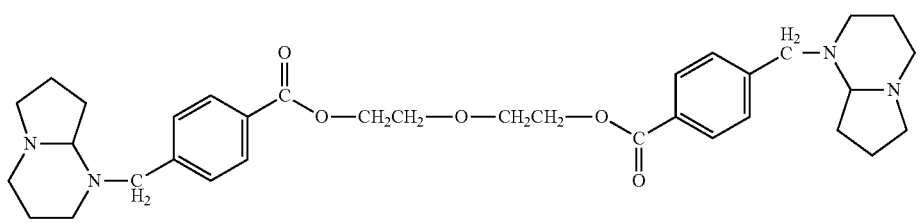

The compounds of this example are prepared according to the procedure as described for the compound of example 2, but using diethylene glycol as alcohol. The product is obtained as a yellowish liquid consisting of approximately 50% of 4-(hexahydro-pyrrolo[1,2-a]pyrimidin-1-ylmethyl)-benzoic acid 2-(2-hydroxy-ethoxy)-ethyl ester and 50% di[4-(hexahydro-pyrrolo[1,2-a]pyrimidin-1-ylmethyl)-benzoate]. The structures are confirmed by $^1$H-NMR analysis.

Example 11 Preparation of [4-(hexahydro-pyrrolo[1,2-a]pyrimidin-1-ylmethyl)-phenyl]-methanol

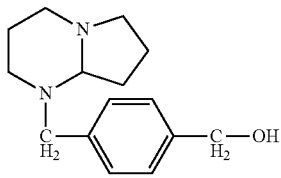 [SMILES: OCc1ccc(CN2CCCN3CCCC32)cc1]

80 g of tetrahydrofuran (THF) and 2.1 g (0.055 mol) lithium aluminium hydride are placed in a reaction flask. A solution of 8 g (0.03 mol) 4-(hexahydro-pyrrolo[1,2-a]pyrimidin-1-ylmethyl)-benzoic acid methyl ester (prepared as described in example 1) in 80 g THF is slowly added at room temperature to the grey suspension. The reaction is stirred for another two hours and subsequently hydrolyzed under vigorous stirring by the addition of 2 g water, 2 g of a 10% sodium hydroxide solution and another 6 g of water. The suspension is filtered, the organic phase dried over $K_2CO_3$ and concentrated in vacuum. 2.95 g (40%) of [4-(hexahydro-pyrrolo[1,2-a]pyrimidin-1-ylmethyl)-phenyl]-methanol are thus obtained as colourless oil. The structure is confirmed by $^1$H-NMR analysis.

$^1$H-NMR (300 MHz, CDCl$_3$), δ [ppm]: 7.33 (q, 4H); 4.68 (s, 2H. —C$\underline{H}_2$OH); 3.93 (d, 1H, 1H of —C$\underline{H}_2$—NR$_2$); 3.15-3.05 (m, 3H, 1H of —C$\underline{H}_2$—NR$_2$ and C(4)$\underline{H}_2$—); 2.82 (m. 1H, H—C(6)); 2.43 (m, 1H), 2.25 (m, 2H), 2.15-1.65 (m, 8H); 1.5 (m, 1H).

Example 12 Preparation of hexanoic acid 4-(hexahydro-pyrrolo[1,2-a]pyrimidin-1-ylmethyl)-benzyl ester

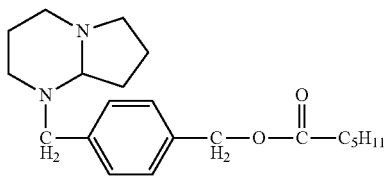

4 g (0.031 mol) of capronic acid methyl ester and 1.9 g (0.0075 mol) of [4-(hexahydro-pyrrolo[1,2-a]pyrimidin-1-ylmethyl)-phenyl]-methanol (compound of example 11) are dissolved in 40 g toluene and placed in a 100 ml reaction flask. 0.14 g (0.017 mol) of lithium hydride are added and the suspension is heated to 125° C. oil bath temperature. The reaction mixture is stirred at this temperature for another 4 hours and then cooled to room temperature. 40 g of water are slowly added under vigorous stirring, the phases are separated and the organic phase is dried over $K_2CO_3$. The solvent is distilled off in vacuum, providing 2.1 g (81%) of 4-(hexahydro-pyrrolo[1,2-a]pyrimidin-1-ylmethyl)-benzyl ester as a slightly pink oil. The structure is confirmed by $^1$H-NMR analysis.

$^1$H-NMR (300 MHz, CDCl$_3$), δ [ppm]: 7.34 (q, 4H); 5.1 (s, 2H. —COO—C$\underline{H}_2$—); 3.93 (d, 1H, one H of —C$\underline{H}_2$—NR$_2$); 3.1 (m, 3H); 2.82 (m, 1H, H—C(6)); 2.45-2.2 (m, 4H); 2.15-1.6 (m, 10H); 1.45 (m, 1H), 1.3 (m, 4H), 0.85 (t, 3H, CH$_3$—CH$_2$—).

Example 13 Preparation of hexanedioic acid 4-(hexahydro-pyrrolo[1,2-a]pyrimidin-1-ylmethyl)-benzyl ester methyl ester

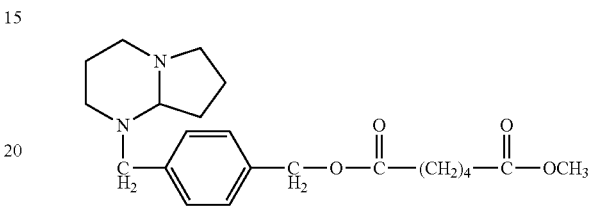

The compound of example 13 is prepared according to the method as given in example 12, except that hexanedioic acid dimethyl ester is used instead of capronic acid methyl ester. 4-(Hexahydro-pyrrolo[1,2-a]pyrimidin-1-ylmethyl)-benzyl ester methyl ester is obtained in 41% yield as colorless oil. The structure is confirmed by $^1$H-NMR analysis.

$^1$H-NMR (400 MHz, CDCl$_3$) δ [ppm]: 7.34 (q, 4H); 5.1 (s, 2H. —COO—C$\underline{H}_2$—); 3.93 (d, 1H, one H of —C$\underline{H}_2$—NR$_2$); 3.67 (s, 3H, C$\underline{H}_3$OCO—); 3.15 (m, 3H); 2.85 (m, 1H, H—C(6)); 2.5-2.25 (m, 4H); 2.15-2.0 (m, 2H); 1.95-1.65 (m, 11H); 1.45 (m, 1H).

Example 14 Preparation of 4-(octahydro-pyrimido[1,2-a]azepin-1-ylmethyl)-benzoic Acid Methyl Ester

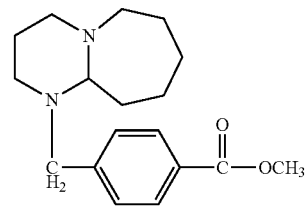 [SMILES: COC(=O)c1ccc(CN2CCCN3CCCCCC32)cc1]

14.1 Preparation of decahydro-pyrimido[1,2-a]azepine

Decahydro-pyrimido[1,2-a]azepine is prepared according to the method as described in example 1a, but using 2,3,4,6,7,8,9,10-octahydro-pyrimido[1,2-a]azepine (DBU) instead of DBN as starting material. 8 g (65%) decahydro-pyrimido[1,2-a]azepine are obtained as a yellow oil. The structure is confirmed by $^{13}$C-NMR spectroscopy.

14.2 Preparation of 4-(octahydro-pyrimido[1,2-a]azepin-1-ylmethyl)-benzoic acid methyl ester 4-(Octahydro-pyrimido[1,2-a]azepin-1-ylmethyl)-benzoic acid methyl ester is prepared according to the method as described in example 1b. 7 g (84%) of 4-(octahydro-pyrimido[1,2-a]azepin-1-ylmethyl)-benzoic acid methyl ester are obtained as a yellow oil. The structure is confirmed by ¹H-NMR and ¹³C-NMR spectroscopy.

¹H-NMR (300 MHz, CDCl₃) δ [ppm]: 7.96 (d, 2H); 7.41 (d, 2H); 3.93 (d, 1H, one H of —C$\underline{H}_2$—NR₂); 3.88 (s, 3H, —COOC$\underline{H}_3$); 3.55 (d, 1H, one H of —C$\underline{H}_2$—NR₂); 3.37 (m, 1H); 3.1-2.95 (m, 2H); 2.8-2.35 (m, 4H); 2.05-1.7 (m, 10H).

Example 15 Preparation of 4-(octahydro-pyrimido [1,2-a]azepin-1-ylmethyl)-benzoic Acid Hexyl Ester

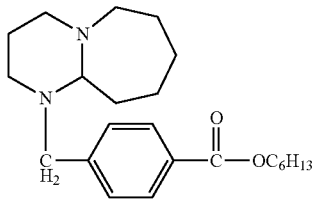

The compound of example 15 is prepared according to the method as described in example 2 but using 4-(octahydro-pyrimido[1,2-a]azepin-1-ylmethyl)-benzoic acid methyl ester (compound of example 14) and 1-hexanol as starting materials. 2 g (82%) of 4-(octahydro-pyrimido[1,2-a]azepin-1-ylmethyl)-benzoic acid hexyl ester are obtained as a yellowish oil. The structure is confirmed by ¹H- and ¹³C-NMR spectroscopy.

¹H-NMR (300 MHz, CDCl₃) δ [ppm]: 7.99 (d, 2H); 7.38 (d, 2H); 4.3 (t, 2H, —COO—C$\underline{H}_2$—); 3.93 (d, 1H, one H of —C$\underline{H}_2$—NR₂); 3.55 (d, 1H, one H of —C$\underline{H}_2$—NR₂); 3.39 (m, 1H); 3.1-2.95 (m, 2H); 2.8-2.35 (m, 4H); 2.05-1.25 (m, 18H); 0.9 (t, 3H, —CH₂—C$\underline{H}_3$).

Example 16 Preparation of potassium 4-(hexahydro-pyrrolo[1,2-a]pyrimidin-1-ylmethyl)-benzoate

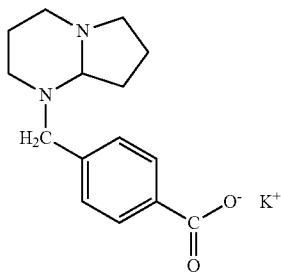

25 g of methanol and 5.5 g (0.02 mol) of 4-(hexahydro-pyrrolo[1,2-a]pyrimidin-1-ylmethyl)-benzoic acid methyl ester (of example 1) are placed in a flask. 1.1 g (0.02 mol) potassiumhydroxide are added and the reaction mixture is stirred at room temperature. After 5 days the solution is concentrated in vacuum. 4-(hexahydro-pyrrolo[1,2-a]pyrimidin-1-ylmethyl)-benzoate is obtained as a white solid. Yield 3.7 g (62%).

¹H-NMR (300 MHz, CDCl₃), δ [ppm]: 7.65 (d, 2H); 6.91 (d, 2H); 3.71 (d, 1H, 1H of —C$\underline{H}_2$—NR₂); 3.23 (s, 3H, —COOCH₃); 3.10-2.95 (m, 2H); 2.88 (d, 1H, 1H of —C$\underline{H}_2$—NR₂); 2.64 (d, 1H); 2.35-1.55 (m, 10H).

Example 17 Preparation of 4-(hexahydro-pyrrolo[1, 2-a]pyrimidin-1-ylmethyl)-benzoic acid 2-(9-oxo-9H-thioxanthen-3-ylsulfanyl)-ethyl ester

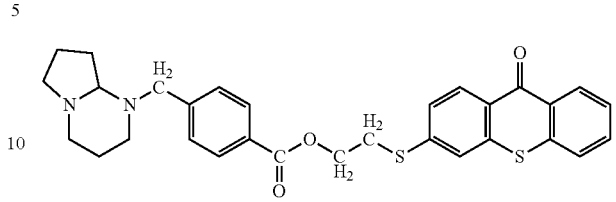

100 g of toluene, 3.24 g (0.0113 mol) of 3-(2-hydroxy-ethylsulfanyl)-thioxanthen-9-one (which was prepared according to the method described in EP354458 and 2.1 g (0.0075 mol) of 4-(hexahydro-pyrrolo[1,2-a]pyrimidin-1-ylmethyl)-benzoic acid methyl ester (of example 1) are placed in a flask equipped with a stirrer and distillation equipment. 0.17 g (0.021 mol) of lithium hydride are subsequently added to the reaction mixture. The suspension is heated to 120° C. (oil bath temperature), stirred for 24 hours and then cooled to room temperature. 40 g of water are slowly added under vigorous stirring, the phases are separated and the organic phase is dried over MgSO₄. The solvent is distilled off in vacuum, providing 1.5 g (38%) of 4-(hexahydro-pyrrolo[1,2-a]pyrimidin-1-ylmethyl)-benzoic acid 2-(9-oxo-9H-thioxanthen-3-ylsulfanyl)-ethyl ester as yellow solid. The structure is confirmed by ¹H-NMR analysis.

¹H-NMR (300 MHz, CDCl₃), δ [ppm]: 8.63-8.57 (2 d, 2H, H—C(1') and H—C(8'); 7.86 (d, 2H); 7.65-7.45 (m, 5H); 7.36 (d, 2H); 4.54 (t, 2H, —COO—C$\underline{H}_2$—CH₂—S—); 3.83 (d, 1H, 1H of —C$\underline{H}_2$—NR₂); 3.40 (t, 2H, —COO—C$\underline{H}_2$—CH₂—S—); 3.15-3.05 (m, 3H); 2.75 (d, 1H); 2.45-1.55 (m, 10H).

Example 18 Preparation of 4-(hexahydro-pyrrolo[1, 2-a]pyrimidin-1-ylmethyl)-benzoic acid 2-(4-benzoyl-phenylsulfanyl)-ethyl ester

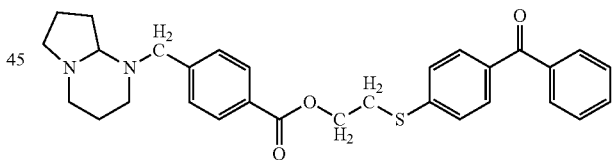

40 g of toluene, 2.9 g (0.0113 mol) of [4-(2-hydroxyethylsulfanyl)-phenyl]-phenyl-methanone (prepared as described in U.S. Pat. No. 4,297,513 A) and 2.1 g (0.0075 mol) of 4-(hexahydro-pyrrolo[1,2-a]pyrimidin-1-ylmethyl)-benzoic acid methyl ester (of example 1) are placed in a flask equipped with a stirrer and distillation equipment. 0.07 g (0.0083 mol) of lithium hydride is subsequently added to the reaction mixture. The suspension is heated to 120° C. (oil bath temperature), stirred for six hours at this temperature and then cooled to room temperature. 40 g of water are slowly added under vigorous stirring, the phases are separated and the organic phase is dried over MgSO₄. The solvent is distilled off in vacuum, providing 1.3 g (34%) of 4-(hexahydro-pyrrolo[1,2-a]pyrimidin-1-ylmethyl)-benzoic acid 2-(4-benzoyl-phenyl-sulfanyl)-ethyl ester as a light brown solid. The structure is confirmed by ¹H-NMR analysis.

¹H-NMR (300 MHz, CDCl₃), δ [ppm]: 7.93 (d, 2H); 7.80-7.70 (2d, 4H, 2H—C(1') and 2H—C(10')); 7.56 (t, 1H, H—C(8')); 7.50-7.35 (m, 6H); 4.55 (t, 2H, —COO—CH₂—CH₂—S—); 3.93 (d, 1H, 1H of —CH₂—NR₂); 3.39 (t, 2H, —COO—CH₂—CH₂—S—); 3.15-3.05 (m, 3H); 2.62 (d, 1H); 2.45-1.55 (m, 10H).

Example 19 Preparation of 4-(hexahydro-pyrrolo[1,2-a]pyrimidin-1-ylmethyl)-benzoic Acid Isopropyl Ester

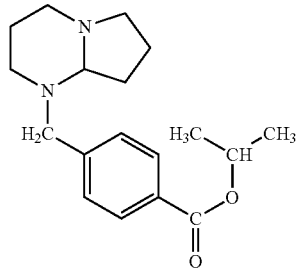 [SMILES: CC(C)OC(=O)c1ccc(CN2CCCN3CCCC32)cc1]

160 g of 2-propanol and 5.5 g (0.02 mol) of 4-(hexahydro-pyrrolo[1,2-a]pyrimidin-1-ylmethyl)-benzoic acid methyl ester (of example 1) are placed in a flask 1.1 g (0.02 mol) of sodium methoxide (30% solution in methanol) is added. After stirring for 5 hours the colourless solution is concentrated in vacuum. 4-(hexahydro-pyrrolo[1,2-a]pyrimidin-1-ylmethyl)-benzoic acid isopropyl ester is obtained as a white solid. Yield 2.1 g (35%)

¹H-NMR (300 MHz, CDCl₃), δ [ppm]: 7.96 (d, 2H); 7.44 (d, 2H); 5.24 (sept, 1H, (CH₃)₂CH—O—); 3.95 (d, 1H, 1H of —CH₂—NR₂); 3.15-3.05 (m, 3H); 2.79 (d, 1H); 2.45 (dxd, 1H); 2.26 (q, 1H); 2.15-1.55 (m, 8H); 1.32 (d, 6H, (CH₃)₂CH—O—).

Example 20 Preparation of 4-(hexahydro-pyrrolo[1,2-a]pyrimidin-1-ylmethyl)-benzoic Acid Allyl Ester

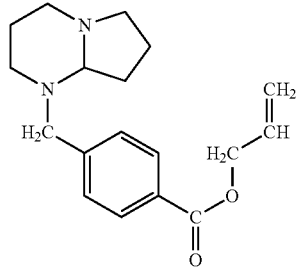 [SMILES: C=CCOC(=O)c1ccc(CN2CCCN3CCCC32)cc1]

The compound of example 20 is prepared according to the method described in example 19, except that the alcohol used is prop-2-en-1-ol. 4-(Hexahydro-pyrrolo[1,2-a]pyrimidin-1-ylmethyl)-benzoic acid allyl ester is obtained as white solid.

¹H-NMR (300 MHz, CDCl₃), δ [ppm]: 7.99 (d, 2H); 7.46 (d, 2H); 6.04 (dxdxt, 1H, CH₂=CH—CH₂—O—); 5.44 (dxd, $J_{trans}$=18 Hz, 1H, CH₂=CH—CH₂—O—); 5.28 (dxd, $J_{cis}$=9 Hz, 1H, CH₂=CH—CH₂—O—); 4.82 (dxdxd, 2H, CH₂=CH—CH₂—O—); 3.95 (d, 1H, 1H of —CH₂—NR₂); 3.15-3.05 (m, 3H); 2.80 (d, 1H); 2.45 (dxd, 1H); 2.26 (q, 1H); 2.15-1.55 (m, 8H).

Example 21 Preparation of N-allyl-4-(hexahydro-pyrrolo[1,2-a]pyrimidin-1-ylmethyl)-benzamide

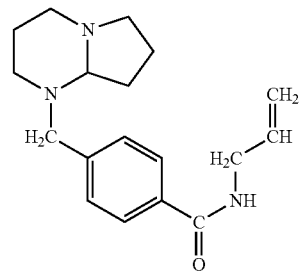 [SMILES: C=CCNC(=O)c1ccc(CN2CCCN3CCCC32)cc1]

The compound of example 21 is prepared according to the method described in example 19, except that allyl amine is used instead of allyl alcohol. The product is obtained as yellowish oily solid.

¹H-NMR (300 MHz, CDCl₃), δ [ppm]: 7.73 (d, 2H); 7.46 (d, 2H); 6.26 (broad t, 1H, CH₂=CH—CH₂—NH—); 5.93 (dxdxt, 1H, CH₂=CH—CH₂—NH—); 5.29 (dxd, $J_{trans}$=18 Hz, 1H, CH₂=CH—CH₂—NH—); 5.22 (dxd, $J_{cis}$=9 Hz, 1H, CH₂=CH—CH₂—NH—); 4.08 (dxdxd, 2H, CH₂=CH—CH₂—NH—); 3.94 (d, 1H, 1H of —CH₂—NR₂); 3.15-3.05 (m, 3H); 2.80 (d, 1H); 2.45 (dxd, 1H); 2.25 (q, 1H); 2.15-1.55 (m, 8H).

Example 22 Preparation of 4-(hexahydro-pyrrolo[1,2-a]pyrimidin-1-ylmethyl)-N-hexyl-benzamide

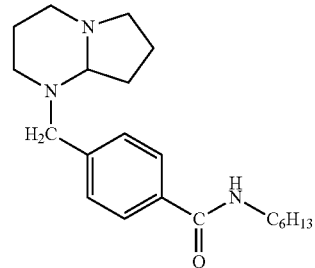

9.9 g (0.04 mol) of 4-(hexahydro-pyrrolo[1,2-a]pyrimidin-1-ylmethyl)-benzoic acid methyl ester (of example 1) and 16.2 g (0.16 mol) of hexylamine are placed in a flask. 0.2 g (0.004 mol) of sodium cyanide is added. The suspension is heated to 130° C. (oil bath temperature), stirred for 24 hours at this temperature and then cooled to room temperature. The reaction mixture is dissolved in 50 g of dichloromethane and 20 g of water are added. The phases are separated and the organic phase is dried over MgSO₄. The solvent is distilled off in vacuum, providing 4-(hexahydro-pyrrolo[1,2-a]pyrimidin-1-ylmethyl)-N-hexyl-benzamide as a white solid with a melting point of 121-126° C. Yield 3.9 g (28%)

¹H-NMR (300 MHz, CDCl₃), δ [ppm]: 7.70 (d, 2H); 7.42 (d, 2H); 6.11 (broad t, 1H, —CONH—); 3.95 (d, 1H, 1H of —CH₂—NR₂); 3.47 (q, J=7 Hz, 2H, —CO—NH—CH₂—); 3.17-3.09 (m, 3H); 2.82 (d, 1H); 2.46 (dxd, 1H); 2.28 (q, 1H); 2.15-1.25 (m, 16H); 0.88 (t, J=5 Hz, 3H, —CH₂—CH₃).

Example 23 Preparation of 4-(hexahydro-pyrrolo[1,2-a]pyrimidin-1-ylmethyl)-N-(2-hydroxy-ethyl)-benzamide

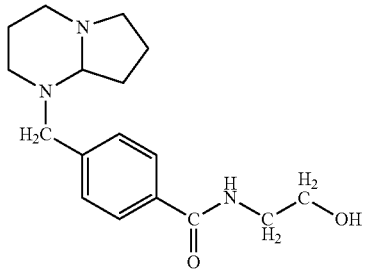 [SMILES: O=C(NCCO)c1ccc(CN2CCCN3CCCC32)cc1]

40 g of tetrahydrofuran (THF) and 0.44 g (0.0013 ml) of 1,3-bis(2,4,6-trimethylphenyl)-imidazolium chloride are placed in a reaction flask. 0.56 g (0.005 mol) of potassium tert-butoxide (solution 1M in THF) are added and the reaction is stirred for two hours at room temperature. 5.4 g (0.0197 mol) of 4-(hexahydro-pyrrolo[1,2-a]pyrimidin-1-ylmethyl)-benzoic acid methyl ester (of example 1) and 1.2 g (0.0197 mol) of ethanolamine are subsequently added to the reaction mixture. After stirring for 12 hours at room temperature, the solvent is distilled off in vacuum. The light brown oil crystallizes upon stirring with diethylether. The suspension is filtered providing 3.1 g (52%) 4-(hexahydro-pyrrolo[1,2-a]pyrimidin-1-ylmethyl)-N-(2-hydroxy-ethyl)-benzamide as a white solid.

$^1$H-NMR (300 MHz, CDCl$_3$), δ [ppm]: 7.72 (d, 2H); 7.43 (d, 2H); 6.80 (broad t, 1H, —CO—NH—CH$_2$—CH$_2$—OH); 3.93 (d, 1H, 1H of —CH$_2$—NR$_2$); 3.83 (t, 2H, —CO—NH—CH$_2$—C$\underline{H}_2$—OH); 3.61 (t, 2H, —CO—NH—C$\underline{H}_2$—CH$_2$—OH); 3.40 (broad s, 1H, —CO—NH—CH$_2$—CH$_2$—O$\underline{H}$); 3.15-3.05 (m, 3H); 2.81 (d, 1H); 2.45 (dxd, 1H); 2.24 (q, 1H); 2.15-1.45 (m, 7H).

Example 24 Preparation of 4-(hexahydro-pyrrolo[1,2-a]pyrimidin-1-ylmethyl)-N-(3-hydroxy-propyl)-benzamide

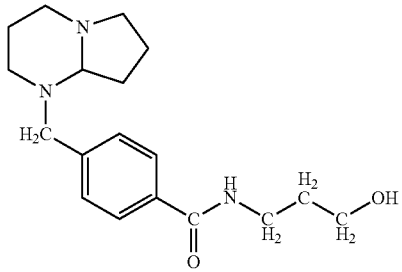 [SMILES: O=C(NCCCO)c1ccc(CN2CCCN3CCCC32)cc1]

The compound of example 24 is prepared according to the method described in example 23, except that the aminoalcohol used is 3-amino-1-propanol. Yellow oily crystals. Yield (69%)

$^1$H-NMR (300 MHz, CDCl$_3$), δ [ppm]: 7.70 (d, 2H); 7.42 (d, 2H); 6.95 (broad t, 1H, —CO—NH—CH$_2$—CH$_2$—CH$_2$—OH); 3.93 (d, 1H, 1H of —CH$_2$—NR$_2$); 3.70 (t, 2H, —CO—NH—CH$_2$—CH$_2$—C$\underline{H}_2$—OH); 3.61 (t, 2H, —CO—NH—CH$_2$—CH$_2$—CH$_2$—OH); 3.15-3.05 (m, 3H); 2.80 (d, 1H); 2.45 (dxd, 1H); 2.24 (q, 1H); 2.15-1.40 (m, 9H).

Example 25 Preparation of 4-(hexahydro-pyrrolo[1,2-a]pyrimidin-1-ylmethyl)-benzoic Acid Ethyl Ester

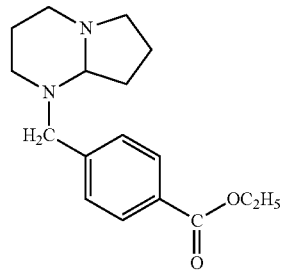

A solution of 7.57 g (0.06 mol) of octahydro-pyrrolo[1,2-a]pyrimidine in 20 g toluene is added dropwise to a colorless solution of 14.6 g (0.06 mol) ethyl 4-(bromomethyl)-benzoate and 6.1 g (0.06 mol) triethylamine in 30 g toluene while stirring. Stirring is continued for 20 hours at room temperature, giving a white slightly viscous and sticky suspension. The suspension is filtered off, and the filtrate is concentrated in vacuum. 4-(Hexahydro-pyrrolo[1,2-a]pyrimidin-1-ylmethyl)-benzoic acid ethyl ester is obtained as a white solid with a melting point of 88.6° C.-92.5° C. Yield 3.2 g (18%).

$^1$H-NMR (300 MHz, CDCl$_3$), δ [ppm]: 7.90 (d, 2H); 7.38 (d, 2H); 4.29 (q, J=7, 2H, —CO—O—C$\underline{H}_2$—CH$_3$); 3.88 (d, 1H, 1H of —CH$_2$—NR$_2$); 3.08 (d, 1H, 1H of —CH$_2$—NR$_2$); 3.05-3.00 (m, 2H); 2.72 (d, 1H); 2.37 (dxd, 1H); 2.20 (q, 1H); 2.15-1.40 (m, 8H); 1.30 (t, J=7, 3H, —CO—O—CH$_2$—C$\underline{H}_3$).

Example 26 Preparation of 1-[4-(hexahydro-pyrrolo[1,2-a]pyrimidin-1-ylmethyl)-phenyl]-ethanone

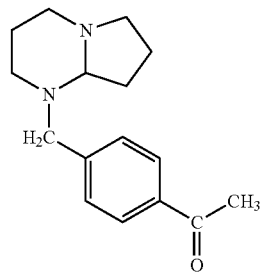 [SMILES: CC(=O)c1ccc(CN2CCCN3CCCC32)cc1]

26.1 Preparation of 1-(4-bromomethyl-phenyl)-ethanone 50 g of acetonitrile, 2.7 g (0.02 mol) of 4-methylacetophenone and 3.9 g (0.022 mol)N-bromosuccinimide are placed in a reaction flask. 0.33 g (0.002 mol) azobisisobutyronitrile (AIBN) are added. The reaction mixture is heated to reflux and stirred for 2 hours at this temperature. The reaction mixture is subsequently cooled down to room temperature and the solvent is distilled off in vacuum. 20 g of toluene is added to the yellow oil, giving a white suspension. The suspension is filtered off, and the filtrate is concentrated in vacuum. 4.2 g of 1-(4-bromomethyl-phenyl)-ethanone are obtained as a yellow oil. The structure is confirmed by ¹H-NMR analysis.

¹H-NMR (300 MHz, CDCl₃), δ [ppm]: 7.96 (d, 2H); 7.50 (d, 2H); 4.52 (s, 2H, —CH₂Br); 2.62 (s, 3H, —CO—CH₃).

26.2 Preparation of 1-[4-(hexahydro-pyrrolo[1,2-a]pyrimidin-1-ylmethyl)-phenyl]-ethanone The compound of example 26.2 is prepared according to the method described in example 25, except that the one of the starting material used is 1-(4-bromomethyl-phenyl)-ethanone (example 26.1). A white solid is obtained with a melting point of 78-85° C. Yield 4.5 g (32%)

¹H-NMR (300 MHz, CDCl₃), δ [ppm]: 7.91 (d, 2H); 7.49 (d, 2H); 3.97 (d, 1H, 1H of —CH₂—NR₂); 3.18 (d, 1H, 1H of —CH₂—NR₂); 3.15-3.10 (m, 2H); 2.82 (d, 1H); 2.60 (s, 3H, —CO—CH₃); 2.46 (dxd, 1H); 2.27 (q, 1H); 2.20-1.45 (m, 8H).

Example 27 Preparation of 3-(hexahydro-pyrrolo[1,2-a]pyrimidin-1-ylmethyl)-benzoic Acid Methyl Ester

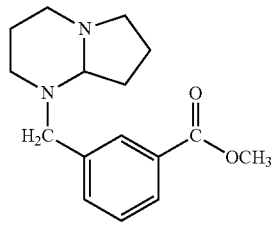 [SMILES: COC(=O)c1cccc(CN2CCCN3CCCC32)c1]

The compound of example 26 is prepared according to the method described in example 1.2, except that the starting material used is methyl 3-(bromomethyl)-benzoate. 3-(Hexahydro-pyrrolo[1,2-a]pyrimidin-1-ylmethyl)-benzoic acid methyl ester is obtained as a yellow oil.

¹H-NMR (300 MHz, CDCl₃), δ [ppm]: 8.02 (s, 1H, H—C(2)); 7.91 (d, 1H, H—C(4)); 7.60 (d, 1H, H—C(6)); 7.37 (t, 1H, H—C(5)); 3.96 (d, 1H, 1H of —CH₂—NR₂); 3.90 (s, 3H, —CO—O—CH₃); 3.13 (d, 1H, 1H of —CH₂—NR₂); 3.15-3.08 (m, 2H); 2.81 (d, 1H); 2.44 (dxd, 1H); 2.25 (q, 1H); 2.15-1.45 (m, 8H).

Example 28 Preparation of 4-(hexahydro-pyrrolo[1,2-a]pyrimidin-1-ylmethyl)-benzoic acid 6-amino-hexyl ester

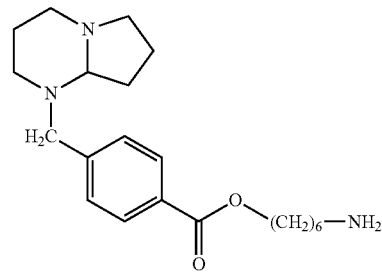

40 g of toluene, 2.6 g (0.023 mol) of 6-amino-1-hexanol and 2.1 g (0.0075 mol) of 4-(hexahydro-pyrrolo[1,2-a]pyrimidin-1-ylmethyl)-benzoic acid methyl ester (of example 1) are placed in a flask equipped with a stirrer and distillation equipment. 0.14 g (0.017 mol) of lithium hydride is subsequently added to the reaction mixture. The suspension is heated to 120° C. (oil bath temperature), stirred for another six hours and then cooled to room temperature. 40 g of water are slowly added under vigorous stirring, the phases are separated and the organic phase is dried over MgSO₄. The solvent is distilled off in vacuum, providing 1.4 g (52%) of 4-(hexahydro-pyrrolo[1,2-a]pyrimidin-1-ylmethyl)-benzoic acid 6-amino-hexyl ester as a light yellow oil. The structure is confirmed by ¹H-NMR analysis.

¹H-NMR (300 MHz, CDCl₃), δ [ppm]: 7.97 (d, 2H); 7.45 (d, 2H); 4.31 (t, 2H, —CO—O—CH₂—); 3.95 (d, 1H, 1H of —CH₂—NR₂); —); 3.15 (d, 1H, 1H of —CH₂—NR₂); 3.15-3.05 (m, 2H); 2.80 (d, 1H); 2.70 (t, 2H, —CH₂—CH₂—NH₂); 2.45 (dxd, 1H); 2.27 (q, 1H); 2.15-1.45 (m, 16H); 1.15 (broad s, 2H, —CH₂—CH₂—NH₂).

Example 29 Preparation of 4-(hexahydro-pyrrolo[1,2-a]-pyrimidin-1-ylmethyl)-benzamide of Poly(Ethylene Imine)

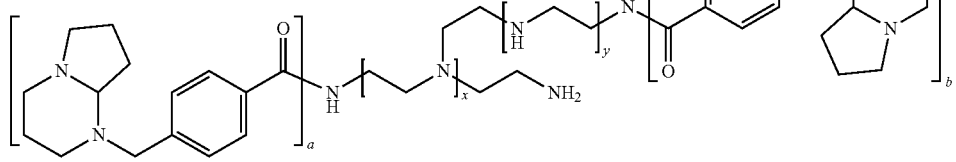

a + b: >0; </=2

10.12 g (0.0369 mol) of 4-(hexahydro-pyrrolo[1,2-a]-pyrimidin-1-ylmethyl)-benzoic acid methyl ester (of example 1) and 10 g poly(ethylene imine) (commercial grade LUPASOL FG; aver-age mole weight: 800 g/mole; provided by BASF) are placed in a flask equipped with stirrer and distillation equipment. The reaction mixture is heated to 130° C. At this temperature the released methanol is distilled off over a period of about 7 hours. The reaction product is a transparent, highly-viscous, yellow-brownish material.

Example 30 Fatty Acid Modification of the Compound of Example 29

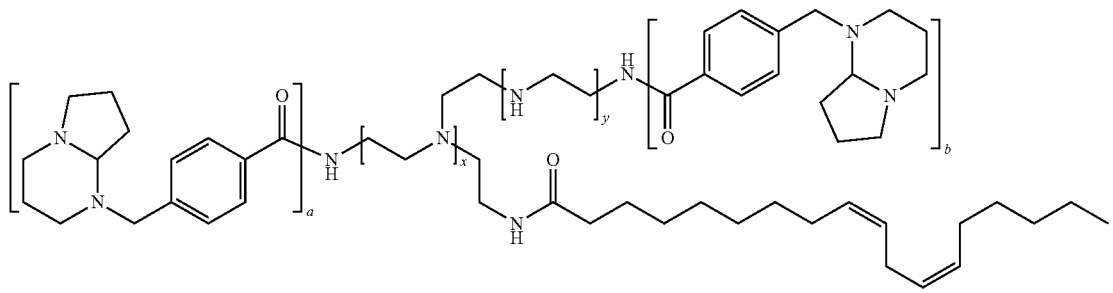

*a* + *b*: >0; </=2

18.83 g of example 29 and 11 g linoleic acid methyl ester are placed in a flask equipped with stirrer and distillation equipment. The reaction mixture is heated to 130° C. At this temperature the released methanol is distilled off over a period of about 7 hours. The reaction product is a transparent, highly-viscous, yellow-brownish material.

Example 31 Siloxane Modification of the Compound of Example 29

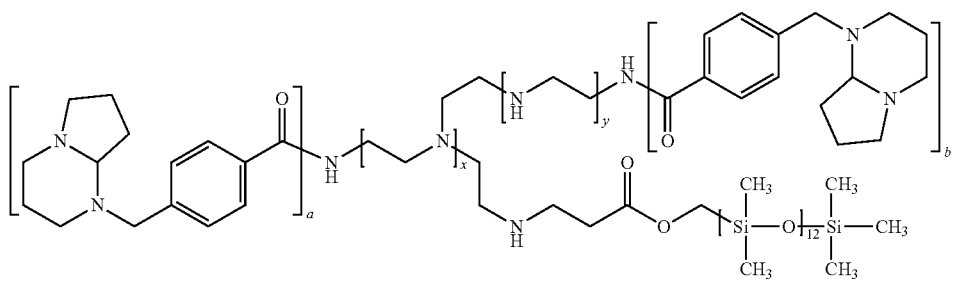

*a* + *b*: >0; </=2

9.79 g of example 29, 20 g 2-propanol and 18.5 g of a monoacryloxymethyl terminated poly-dimethylsiloxane [monofunctional, mole weight: 1000-1200 g/mole] are placed in a flask equipped with stirrer and heated to 50° C. After a reaction period of about 2 h at 50° C. the solvent is removed by distillation under reduced pressure. A transparent, viscous reaction product is obtained.

Example 32 Preparation of 4-(hexahydro-pyrrolo[1,2-a]pyrimidin-1-ylmethyl)-benzoic acid 6-acryloyloxy-hexyl ester

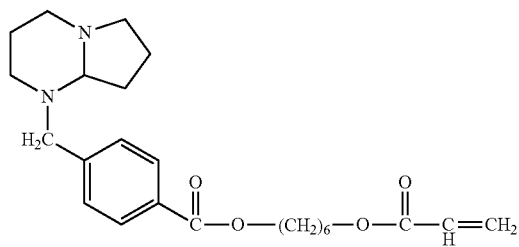

Immobilized lipase (commercially available NOVOZYME 435, provided by NOVO NORDISK A/S; 0.3 g) is added to a solution of 4-(hexahydro-pyrrolo[1,2-a]pyrimidin-1-ylmethyl)-benzoic acid 6-hydroxy-hexyl ester (of example 4, 6.2 g, 17.2 mmol) and acrylic acid methyl ester (2.8 g, 32.5 mmol) in toluene (40 ml). The resulting dispersion is stirred and held at 60° C./600 mbar by means of a rotary evaporator, the progress of the reaction being monitored by GLC. After five hours, the dispersion is filtrated. New enzyme (0.3 g) and acrylic acid methyl ester (2.8 g) are added and the dispersion held another eight hours at 60° C./600 mbar. Filtra-tion and evaporation of volatiles leaves 6.8 g of the title compound as slightly yellow resin. Assay (GLC, area %) >90%. EI-MS ⊐m/z, %⊐ for $C_{24}H_{34}N_2O_4$ (414): found 413 (100%), 414 (35%), 415 (10%).

Example 33 Preparation of 4-(hexahydro-pyrrolo[1,2-a]pyrimidin-1-ylmethyl)-thiobenzoic acid S-butyl ester

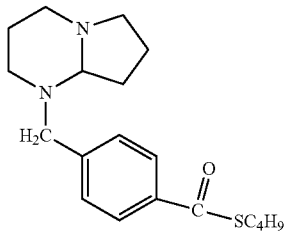

0.13 g (16.6 mmol) lithium hydride are added to a solution of 4.12 g (15 mmol) 4-(hexahydro-pyrrolo[1,2-a]-pyrimidin-1-ylmethyl)-benzoic acid methyl ester (of example 1) and 2-04 g (22.6 mmol) n-butanthiol in 40 ml toluene. The reaction mixture is heated to 60° C. during 24 hours. After cooling the solvent is evaporated and the residue stirred with heptane.

The precipitation formed (4-(hexahydro-pyrrolo[1,2-a]-pyrimidin-1-ylmethyl)-benzoic acid methyl ester) is filtered off, the filtrate evaporated and the residual material treated by the same procedure. 4-(Hexahydro-pyrrolo[1,2-a]pyrimidin-1-ylmethyl)-thiobenzoic acid S-butyl ester is thus obtained as a yellowish sticky solid.

$^{1}$H-NMR (300 MHz, CDCl$_3$), δ [ppm]: 7.98 (d, 2H); 7.41 (d, 2H); 3.94 (d, 1H, 1H of —CH$_2$—NR$_2$); 3.12 (d, 1H, 1H of —CH$_2$—NR$_2$); 3.05-3.00 (m, 2H); 2.72 (d, 1H); 2.69 (t. 2H, —CO—S—CH$_2$—); 2.42 (dxd, 1H); 2.24 (q, 1H); 2.15-1.40 (m, 8H); 1.65 (quintet, 2H, COS—CH$_2$—CH$_2$—C$_2$H$_5$); 1.40 (quintet, 2H, COS—C$_2$H$_4$—CH$_2$—CH$_3$); 0.92 (t, J=7, 3H, —CO—SC$_3$H$_5$—CH$_3$). $^{13}$C-NMR (400 MHz, CDCl$_3$): 191.8 (—CO—S—C$_4$H$_9$). APCI-MS [m/z, %] for C$_{24}$H$_{34}$N$_2$O$_4$ (332.51): found 330 (100%), 250 (55%).

APPLICATION EXAMPLES

Example A1

Component A (=hydroxy component) is prepared by mixing the following ingredients:
  73.0 g of a hydroxyl bearing polyacrylates (70% in butyl acetate); DESMOPHEN® A VP LS 2350; provided by Bayer AG
  0.9 g of an additive (10% in butyl acetate); BYK 333; provided by Byk
  0.7 g of an additive (50% supply form); BYK 355; provided by Byk
  0.7 g of an additive (4% supply form); BYK 141; provided by Byk
  24.7 g of a mixture of xylene/methoxypropylacetate/butylacetate in the ratio 1:1:1 as solvent A photocurable formulation is prepared by mixing the following components:
  0.48 g (=7.3%, based on 100% of the total weight of the formulation) of the photolatent base compound of example 1
  0.28 g (=4.3%) of benzophenone as a sensitizer compound; DAROCUR® BP; provided by Ciba Scecialty Chemicals
  3.76 g (=57.7%) of Component A (as described above)
  2.00 g (=30.7%) of an aliphatic isocyanate (HDI trimer); DESMODUR® N 3390; provided by Bayer AG The photolatent base compound and the sensitizer are dissolved in Component A and the isocyanate component is only added just prior to the application.

The formulation is applied with a slit coater on 30-cm long glass plates (76 μm wet film thickness). The samples are dried for 5 min at room temperature and irradiated using an association of two medium pressure mercury lamps (80 W/cm each) at a belt speed of 5 m/min. As a reference, the operation is repeated in the absence of light. The curing time of the samples is monitored using a drying recorder from Byk-Gardner, where a needle moves for 12 hours at constant speed over the whole length of the coated substrate. Evaluation of the trace in the coating allows an assessment of the curing process, which is divided into three steps, phase 1 consisting of evaporation of the solvent, phase 2 being the first crosslinking, and phase 3 finishing with the achievement of a tack-free coating. After exposure the sample is tackfree after 3 h, while the unirradiated sample is tackfree after 7.5 h.

The results show, that the photolatent base is activated upon irradiation and the released base accelerates the crosslinking process, while without exposure crosslinking takes more than double time, an indication of the high stability of the photolatent base compound.

Example A2

A photocurable formulation is prepared by mixing the following components:
  0.3 g (=2.9%, based on 100% of the total weight of the formulation) of the photolatent base compound of example 1
  0.2 g (=1.9%) of benzophenone as a sensitizer compound; DAROCUR® BP; provided by Ciba Scecialty Chemicals
  10.0 g (=95.2%) of an aliphatic isocyanate (HDI trimer); DESMODUR® N 3390; provided by Bayer AG The photolatent base compound and the sensitizer are dissolved in the isocyanate. 100 μm thick films are applied on glass plates. One sample is irradiated using an association of two medium pressure mercury lamps (80 W/cm each) at a belt speed of 5 m/min, another one is stored in the dark. Samples are further stored for 40 minutes in a desiccator in a humid atmosphere (relative humidity [RH]=95%) at 60° C.

The irradiated sample crosslinks and a dried foam is formed. The sample without light exposure remains tacky.

An indication that the photolatent base compound releases a base upon irradiation which starts the crosslinking process, while without irradiation no sufficient amount of base is released to completely crosslink the formulation.

Example A3

Component A (=hydroxy component) is prepared by mixing the following ingredients:
  36.0% of a trifunctional polypropylene ether polyol; DESMOPHEN® A 5034 BT; provided by Bayer AG
  64.0% of a polyester-polyol; BAYCOLL® VP KA 8576; provided by Bayer AG A photocurable formulation is prepared by mixing the following components:
  2.4% of the photolatent base compound of example 1
  2.4% of isopropylthioxanthone as a sensitizer compound; DAROCUR® ITX; provided by Ciba Scecialty Chemicals 15.8% of butyl acetate as solvent; provided by Aldrich
39.7% of Component A (as described above)
39.7% an aromatic polyisocyanate prepolymer; DESMO-DUR® E 23; provided by Bayer AG The photolatent base compound and the sensitizer are dissolved in the isocyanate shortly before the application. A 100 µm thick film is applied on glass plates (=plate A). The film is dried for 10 minutes at 40° C. A second glass plate (plate B), not coated with the adhesive formulation, is pressed on plate A. After laminating plate A and plate B, the system is exposed to UV light (medium pressure mercury lamp from IST, one pass at a belt speed of 5 m/min with 2 lamps at 80 W/cm). It is no more possible to separate both glass plates after storing the irradiated sample for 100 min.

Example A4

A4.1: Preparation of a Urethane Acrylate Based on Isophorone Diisocyanate and 4-Hydroxy-Butyl Acrylate The reaction is carried out under a nitrogen atmosphere, with all of the commercial chemicals used being employed without further purification.

1566.8 g (13.78 mol of NCO) of isophorone diisocyanate, 2.3 g of dibutyltin dilaurate, 2.3 g of 2,5-di-t-butyl-p-cresol and 802.8 g of butyl acetate are charged to a three-necked flask with condenser and apparatus for dropwise addition. Dry nitrogen is sparged through the reaction mixture and the temperature is slowly increased to 60° C. 1987 g (13.78 mol) of 4-hydroxybutyl acrylate are added, and the reaction solution slowly warms to 80° C. The temperature is held at 80° C. and the dropwise addition apparatus is rinsed with butyl acetate (86.6 g). By titration for the remaining amount of isocyanate, the reaction is monitored, and is ended when the isocyanate content is less than 0.2%, based on solids. A reaction product having the following physical properties is obtained:

Remaining amount of 4-hydroxybutyl acrylate: <0.002% based on solids (HPLC analysis),
Colour: <<Gardner 1,
Viscosity: 43 cPa s (20° C.),
Solids: 79.3% (1 hour at 140° C.),
GPC data (polystyrene standard) $M_n$ 778, $M_w$ 796, d=1.02.

A4.2: Preparation of a Malonate Polyester

The reaction is carried out under a nitrogen atmosphere, with all of the commercial chemicals used being employed without further purification.

In a reaction vessel with stirrer and condenser, 1045 g of 1.5-pentanediol, 1377.4 g of diethyl malonate and 242.1 g of xylene are carefully heated at reflux. The maximum temperature of the reaction mixture is 196° C., while the temperature at the top of the condenser is held at 79° C. In this way 862 g of ethanol are distilled off, corresponding to a conversion of 97.7%. Xylene is then stripped off under reduced pressure at a temperature of 200° C. The polymer obtained has a solid of 98.6%, a viscosity of 2710 mPa s and an acid number of 0.3 mg KOH/g based on solids. $M_n$ is 1838, $M_w$ is 3186, and the colour is 175 on the APHA scale (American Public Health Association; "Hazen" colour number; ISO 6271).

A4.3: Preparation of the photopolymerizable formulation

The two resin components prepared as described in A4.1 and A4.2 are mixed in a weight ratio of 1:2. Then 0.5% of benzophenone (DAROCUR® BP, Ciba Specialty Chemicals) as sensitizer is added to the formulation as well as 2.5% of the photolatent base of example 1. The photolatent base and the sensitizer are well dissolved in the formulation at 50° C. using a magnet stirrer.

Reactivity testing is performed with a dry time measuring apparatus (Byk-Rekorder from Byk Gardner). A needle is drawn at constant rate over a planar glass plate. The formulation comprising the photoinitiator is applied to this glass plate using a doctor blade with a slot height of 75 µm. During the measurement, the measuring apparatus is exposed to light using two daylight lamps (Original Hanau 40 W 001660) at a distance of 1 m. "Stage 1" reflects the time at which the components have not yet reacted with one another. Subsequently, gelling and curing of the formulation start. At the time indicated by "Stage 3" the curing of the formulation is at an end. The shorter is the time taken to reach the individual stages, the more reactive is the formulation. The results are listed in Table 1 in the columns headed "Stage 1" and "Stage 3".

In order to test the hardness and the yellowing, the formulations are applied to white-primed chipboard panels using a doctor blade with a slot height of 100 µm. Curing is effected under 6 TL 40 W/03 (Philips) lamps for a period of 17 hours. This is followed by measurement of the Konig pendulum hardness "PH" in sec (DIN 53157). Furthermore the storage stability of formulation containing the photoinitiator is measured. Therefore the liquid Formulation as described above is stored in a brown glass bottle in a dark place at room temperature. After certain intervals the viscosity is measured with the help of a cone plate Viscosimeter. The re-suits are collected in Table 2 (viscosity is given in Poises). The lower the difference in viscosity after a certain storage time at room temperature compared to a formulation not comprising any photolatent base and sensitizer, the better is the storage stability of the photoinitiator in the formulation.

TABLE 1

| Compound of example | Sensitizer | Stage 1 [h] | Stage 3 [h] | PH [sec] | b* |
|---|---|---|---|---|---|
| 1 | DAROCUR® BP | 3.5 | 4 | 101 | 5.3 |

TABLE 2

| Compound of example | Sensitizer | Viscosity after X days storage at room temperature [Poises] | | |
|---|---|---|---|---|
| | | 0 d | 1 d | 2 d |
| formulation without photolatent base and without sensitzer | | 6.4 | 6.3 | 6.5 |
| 1 | DAROCUR® BP | 6.2 | 6.2 | 6.3 |

Example A5: Curing of a 2-Components Polyurethane System

A polyurethane is the reaction product of two basic components: a polyol (Component A) and a polyisocyanate (Component B).

Component A (=hydroxy component) is prepared by mixing the following ingredients:
73.0 g of a hydroxyl bearing polyacrylates (70% in butyl acetate); DESMOPHEN® A VP LS 2350; provided by Bayer AG
0.9 g of an additive (10% in butyl acetate); BYK 333; provided by Byk 0.7 g of an additive (50% supply form); BYK 355; provided by Byk
0.7 g of an additive (4% supply form); BYK 141; provided by Byk
24.7 g of a mixture of xylene/methoxypropylacetate/butylacetate in the ratio 1:1:1 as solvent Component B: aliphatic polyisocyanate (HDI Trimer) DESMODUR N 3390 BA (from Bayer AG).

A photocurable formulation is prepared by mixing the following components:
  0.94 g (=4.7%, based on 100% of the total weight of the formulation) of the photolatent base compound of example 1.
  0.46 g (=2.3%) of a sensitizer compound, either benzophenone (DAROCUR® BP; provided by Ciba Inc.) or isopropylthioxanthone (DAROCUR® ITX; provided by Ciba Inc.)
  14.7 g (=73.5%) of Component A (as described above)
  3.9 g (=19.5%) of Component B (as described above)

The photolatent base compound and the sensitizer are dissolved in Component A and the isocyanate component is only added just prior to the application.

The formulation is applied with a slit coater on 30-cm long glass plates (76 μm wet film thickness). The samples are then irradiated 15 min. under UV-A light (TL 40 W/05) prior to the curing time measurement; the latter is monitored using a drying recorder from Byk-Gardner, where a needle moves for 6 hours at constant speed over the whole length of the coated substrate. Evaluation of the trace in the coating allows an assessment of the curing process, which is divided into three steps, phase 1 consisting of evaporation of the solvent, phase 2 being the first crosslinking, and phase 3 finishing with the achievement of a tack-free coating. The results are collected in table 3.

TABLE 3

| photolatent base/sensitizer | Without exposure to UV-A | With exposure to UV-A |
|---|---|---|
| of example 1/benzophenone | 20 min. | 5 min. |
| of example 1/isopropylthioxanthone | 30 min. | 10 min. |

The results show that the photolatent base is activated upon irradiation and the released base accelerates the crosslinking process, while without exposure crosslinking takes more than 3 times longer; this is an indication of the high stability of the photolatent base compound.

Example A6: Curing of a 2-Components Epoxy/Thiol System

A photocurable formulation is prepared by mixing the following components:
  Component A (=epoxy-functional component):
  10.0 g (=4.0%, based on 100% of the total weight of the formulation) of a low viscosity BADGE epoxy resin (Rutapox 0162, provided by Hunstman).
  4.0 g (=17.6%) of butyl-acetate.
  0.2 g (=0.9%) of a levelling additive (Byk 306, provided by Byk Chemie)
  Component B (polythiol component):
  7.8 g (=34.3%) of a tetrafunctional polythiol, pentaerythritol-tetramethylpropionate (PETMP, supplied by Bock Thiol Chemicals)
  To these 2 compounds are added:
    0.356 g (=1.6%, based on 100% of the total weight of the formulation, or 1.9% on solids) of a photolatent base, corresponding to one of the examples as indicated in the table 4
    0.356 g of a photosenstizer, either benzophenone (DAROCUR® BP, provided by Ciba Inc.) or [4-(4-methylphenylthio)phenyl]-phenylmethanone (SPEEDCURE BMS, provided by Lambson Ltd.), except in the case of the latent base compounds of Example 17 and Example 18, because both products contain an "internal" sensitizer moiety The photolatent base compound and the sensitizer are dissolved in the mixture of both components A and B. The coating formulation is then applied at about 50 μm dry film thickness, by means of a slit coater onto a 30 cm long glass plate. For each photolatent base compound, one coated glass sample is irradiated using an association of two medium pressure mercury lamps (100 W/cm each) at a belt speed of 5 m/min, while another one is stored in the dark. The tack-free time is then monitored using a drying recorder from Byk-Gardner, where a needle moves for 12 hours at constant speed over the whole length of the coated glass substrate. Evaluation of the trace in the coating allows an assessment of the curing process, which is divided into three steps, phase 1 consisting of evaporation of the solvent, phase 2 being the first crosslinking, and phase 3 finishing with the achievement of a tack-free coating. The results in terms of tack-free time are summarized in below table 4.

TABLE 4

| photolatent base/sensitizer | Pot-life | Tack-free time without exposure | Tack-free time with exposure |
|---|---|---|---|
| No catalyst | >24 hrs. | remains wet | remains wet |
| DBN# (0.5%) | 0 | gels after mixing | gels after mixing |
| compound of ex. 1/ benzophenone | >6 hrs. but <24 hrs. | 270 min. | 30 min. |
| compound of ex. 1/ [4-(4-methylphenyl-thio)phenyl]-phenyl-methanone | >6 hrs. but <24 hrs. | 285 min. | 15 min. |
| compound of ex. 18 | >24 hrs. | 520 min. | 60 min. |

DBN is the base 1,5-diazabicyclo[4.3.0]non-5-ene

The results are an indication that the photolatent base compound releases a base upon irradiation which starts the crosslinking process, while without irradiation no sufficient amount of base is released to completely crosslink the formulation.

Example A7: Curing of a 1-Component Blocked-Isocyanate/Polyol System

Component A is prepared by mixing the following ingredients:
  2.6 g (=19.2% of the total formula) of a polyester polyol (DESMOPHEN® 1100; provided by Bayer AG), as hydroxyl component
  2.0 g (=14.7% of the total formula) of butyl-acetate as diluent.
  Component B
  8.3 g (=61.2%) of blocked isocyanate (DESMODUR® 4282; provided by Bayer AG)

A reference formulation is prepared by mixing the above mentioned components with amidine as non-photolatent catalyst:

0.069 g (=0.5%) of 1,5-diazabicyclo[4.3.0]non-5-ene (DBN)

The test photocurable formulations are prepared by mixing the above mentioned components (A and B) with the following sensitized photolatent amidine compound:
- 0.42 g (=3.1%) of the photolatent base of example 1
- 0.24 g (=1.8%) of isopropylthioxanthone as a sensitizer compound (DAROCUR® ITX; provided by Ciba Inc.)

The catalyst or the photolatent base compound, together with the sensitizer, is dissolved in the mixture of both components A and B. During and after mixing, the formulations are kept protected from light (in the dark) and stored in a jar; the time (after mixing) until the coating formulation is no longer liquid and applicable is observed and recorded in order to determine the pot-life of the formulation and confirm the latency of the photolatent base compound in the absence of exposure to UV light. On the other hand, the coating formulation is applied at about 150 μm wet film thickness, by means of a slit coater, onto a glass plate (size suitable for pendulum hardness measurement). For each coating formulation: 2 coated glass plates are irradiated using an association of two medium pressure mercury lamps (80 W/cm each) at a belt speed of 5 m/min; after UV exposure, one of the glass plates is placed in an oven at 120° C. for 15 min., while the other one is placed in an oven at 150° C. for 15 min. Two other coated glass plates are only put in an oven, one at 120° C. for 15 min. and the other one at 150° C. for 15 min. Following these curing conditions, and when the coating is no longer tacky. The results, in terms of the pendulum hardness according to Konig (PH; according to DIN 53157) of the coatings after curing, as well as the potlife of the frormulations are summarized in the following table 5.

TABLE 5

| | isopropylthioxanthone + compound of ex. 1 | |
|---|---|---|
| | DBN | without UV | with UV |
| PH unblocking: 15 min 120° C. | sticky | sticky | 4.2 |
| PH unblocking: 15 min 140° C. | sticky | 15.4 | 57.4 |
| Potlife | 1 h | | >24 h |

The invention claimed is:

1. A coated substrate coated on at least one surface with a composition comprising:
   (A) at least one photolatent base compound of the formula (Ib), (IIb), (IIIb), (Ic), (IIc), or (IIIc); and
   (B) at least one organic compound which is capable of a base-catalysed addition, condensation or substitution reaction or which is converted into a different form by a base-catalysed reaction;

wherein the photolatent base compound of the formula (Ib), (IIb), (IIIb), (Ic), (IIc), or (IIIc) is defined as follows:

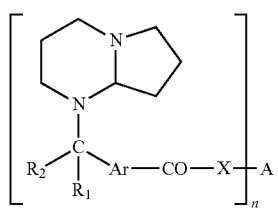
(Ib)

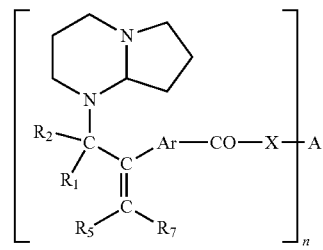
(IIb)

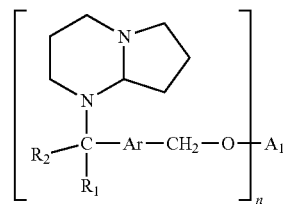
(IIIb)

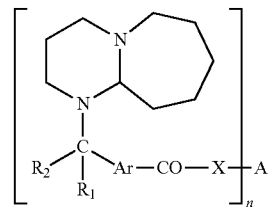
(Ic)

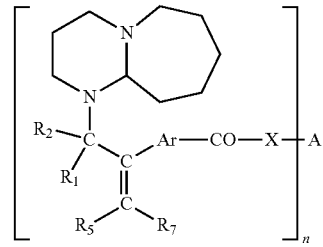
(IIc)

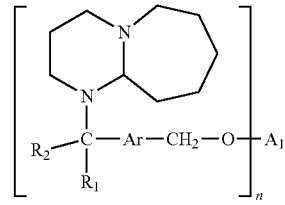
(IIIc)

wherein

Ar is phenylene, biphenylene, naphthylene, anthrylene or anthraquinonylene all of which are unsubstituted or are substituted by one or more $C_1$-$C_4$-alkyl, $C_2$-$C_4$-alkenyl, CN, $OR_{11}$, $SR_{11}$, $CH_2OR_{11}$, $COOR_{12}$, $CONR_{12}R_{13}$ or halogen;

$R_1$, $R_2$, $R_7$ and $R_8$ independently of one another are hydrogen or $C_1$-$C_6$-alkyl;

$R_{11}$ is hydrogen or $C_1$-$C_6$-alkyl;

$R_{12}$ and $R_{13}$ independently of one another are hydrogen;

n is an integer from 1-10;

X is a direct bond, O, S or $NR_{10}$;

A when n is 1, is $C_2$-$C_{18}$-alkyl which is interrupted by one or more O or $N(R'_{13})$ or is uninterrupted $C_1$-$C_{18}$alkyl which is substituted by one or more $C_1$-$C_6$-hydroxyalkyl, $OR_{11}$, $NR_{12}R_{13}$, or $OCOR_{14}$; or A when n is 1, denotes a group

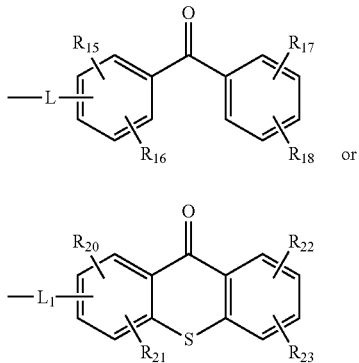

(BP)

or (TX)

or, when X is O, additionally X-A denotes X⁻Y⁺;
A when n is greater than 1,
is an n-valent saturated or unsaturated $C_2$-$C_{50}$hydrocarbon radical, which optionally is interrupted by one or more O, S, N($R'_{13}$), phenylene, naphthylene,

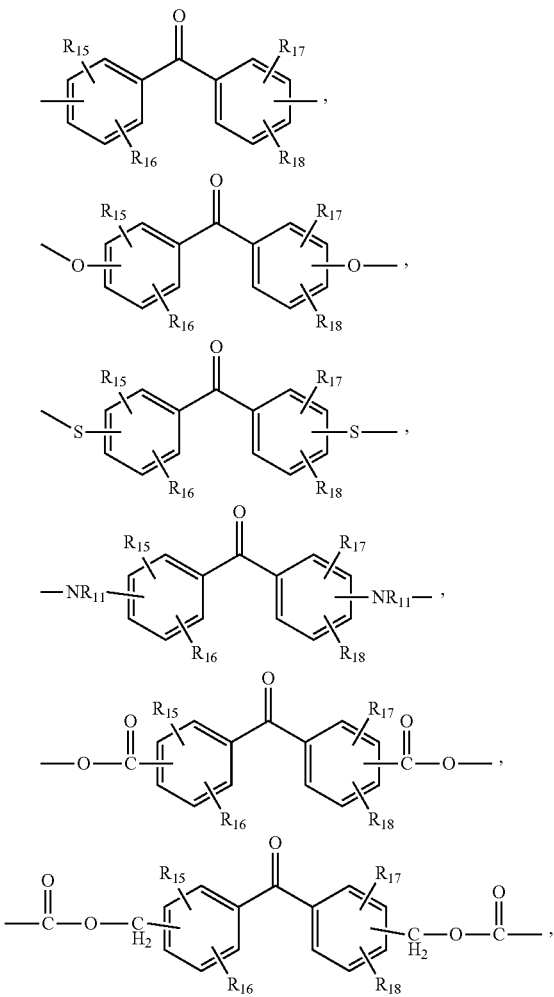

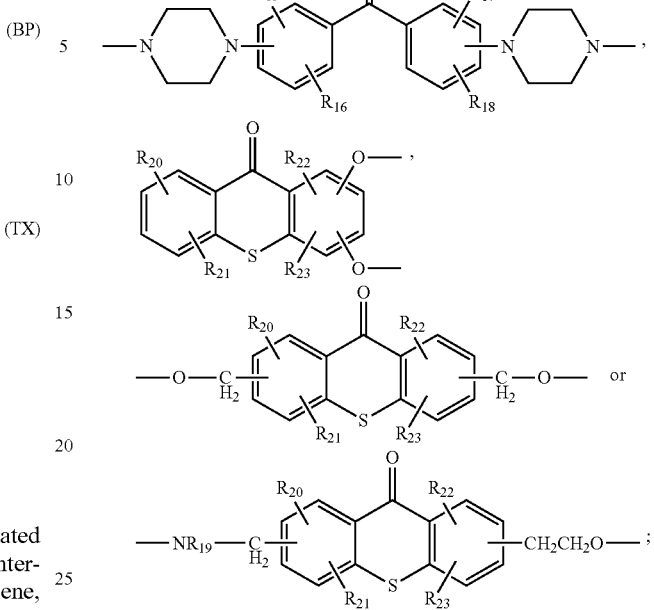

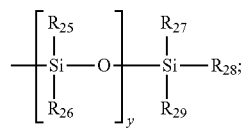

and which uninterrupted or interrupted n-valent saturated or unsaturated $C_2$-$C_{50}$hydrocarbon radical is unsubstituted or is substituted by one or more $C_1$-$C_8$-alkyl, $C_1$-$C_6$-hydroxyalkyl, CN, $OR_{11}$, $SR_{11}$, $NR_{12}R_{13}$, $COOR_{12}$ or halogen;

or A, when X is $NR_{10}$, is a n-valent polyalkylene-imine; wherein the n-valent polyalkylene-imine is uninterrupted or interrupted by one or more (CO), (CO)O or double bonds and wherein the uninterrupted or interrupted n-valent polyalkylene-imine is unsubstituted or substituted by or, if X is O, additionally one or more X-A denote $X_n^-$ $Y^{n+}$ or $X_n^-$ n $Y^+$;

y is an integer from 1-20;
z is an integer from 1-8;
$R'_{13}$ has one of the meanings as given for $R_{12}$ and $R_{13}$ or is a group (TX);
$R_{10}$ has one of the meanings as given for A, when n is 1;
$A_1$, when n is 1, is hydrogen, $C_1$-$C_{18}$alkanoyl, $C_2$-$C_{18}$-alkanoyl which is interrupted by one or more O and/or CO and which uninterrupted or interrupted $C_2$-$C_{18}$alkanoyl is unsubstituted or substituted by one or more $C_1$-$C_4$-alkyl, $C_2$-$C_4$-alkenyl, phenyl, CN, $OR_{11}$, $SR_{11}$, $NR_{12}R_{13}$, $COOR_{12}$ or halogen;
or said uninterrupted or interrupted $C_2$-$C_{18}$alkanoyl is substituted by $C_6$-$C_{10}$-aryl which is unsubstituted or substituted by one or more $C_1$-$C_4$-alkyl, $C_2$-$C_4$-alkenyl, CN, $OR_{11}$, $SR_{11}$, $NR_{12}R_{13}$, or halogen;
or $A_1$ is $C_3$-$C_{18}$-alkenoyl which is unsubstituted or substituted by one or more $C_1$-$C_4$-alkyl, $C_2$-$C_4$-alkenyl, CN, $OR_{11}$, $SR_{11}$, $NR_{12}R_{13}$, $COOR_{12}$, halogen or by $C_6$-$C_{10}$-aryl which is unsubstituted or substituted by one or more $C_1$-$C_4$-alkyl, $C_2$-$C_4$-alkenyl, CN, $OR_{11}$, $SR_{11}$, $NR_{12}R_{13}$ or halogen;

$C_2$-$C_{18}$-alkylaminocarbonyl, which is unsubstituted or substituted by one or more $C_1$-$C_4$-alkyl, $C_2$-$C_4$-alkenyl, CN, $OR_{11}$, $SR_{11}$, $NR_{12}R_{13}$, $COOR_{12}$ or halogen;

$C_6$-$C_{20}$arylaminocarbonyl, which is unsubstituted or substituted by one or more $C_1$-$C_4$-alkyl, $C_2$-$C_4$-alkenyl, $OR_{11}$, $NR_{12}R_{13}$ or halogen;

$C_7$-$C_{20}$-arylalkylaminocarbonyl which is unsubstituted or substituted by one or more $C_1$-$C_4$alkyl, $C_2$-$C_4$-alkenyl, $OR_{11}$, $NR_{12}R_{13}$ or halogen;

$C_7$-$C_{15}$-aroyl or $C_5$-$C_{15}$-heteroaroyl, both of which are unsubstituted or substituted by one or more $C_1$-$C_4$-alkyl, $C_2$-$C_4$-alkenyl, CN, $OR_{11}$, $SR_{11}$, $NR_{12}R_{13}$, or halogen; or $A_1$ when n is 1, denotes a group

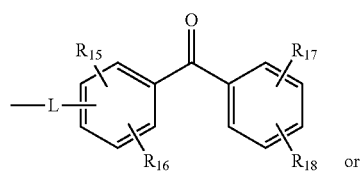 (BP)

or

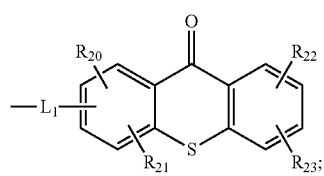 (TX)

$A_1$, when n is greater than 1, is a n-valent $C_2$-$C_{30}$alkanoyl which optionally is interrupted by one or more O and which uninterrupted or interrupted $C_2$-$C_{30}$alkanoyl is unsubstituted or is substituted by one or more $C_1$-$C_4$alkyl, $C_2$-$C_4$-alkenyl, CN, $OR_{11}$, $SR_{11}$, $NR_{12}R_{13}$, $COOR_{12}$ or halogen;

a n-valent $C_8$-$C_{20}$aroyl or $C_6$-$C_{20}$heteroaroyl, both of which are unsubstituted or substituted by one or more $C_1$-$C_4$-alkyl, $C_2$-$C_4$-alkenyl, CN, $OR_{11}$, $SR_{11}$, $NR_{12}R_{13}$, $COOR_{12}$ or halogen;

a n-valent $C_{10}$-$C_{20}$-aralkanoyl, which is unsubstituted or substituted by one or more $C_1$-$C_4$-alkyl, $C_2$-$C_4$-alkenyl, CN, $OR_{11}$, $SR_{11}$, $NR_{12}R_{13}$, $COOR_{12}$ or halogen; or is a n-valent $C_1$-$C_{30}$-alkylaminocarbonyl, which is unsubstituted or substituted by one or more $C_1$-$C_4$-alkyl, $C_2$-$C_4$-alkenyl, CN, $OR_{11}$, $SR_{11}$, $NR_{12}R_{13}$, $COOR_{12}$ or halogen, wherein said unsubstituted or substituted n-valent $C_1$-$C_{30}$-alkylaminocarbonyl optionally consists of several mono-valent $C_1$-$C_{30}$-alkylaminocarbonyl groups which are linked via dimers or trimers of isocyanates or derivatives thereof; or is a n-valent $C_6$-$C_{20}$ arylaminocarbonyl, which is unsubstituted or substituted by one or more $C_1$-$C_4$-alkyl, $C_2$-$C_4$-alkenyl, CN, $OR_{11}$, $SR_{11}$, $NR_{12}R_{13}$, $COOR_{12}$ or halogen; or $A_1$ when n is greater than 1, denotes a group

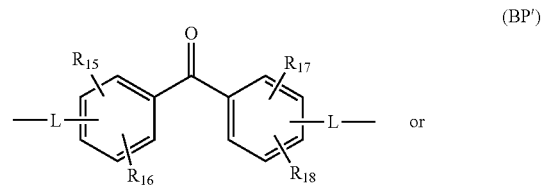 (BP')

or

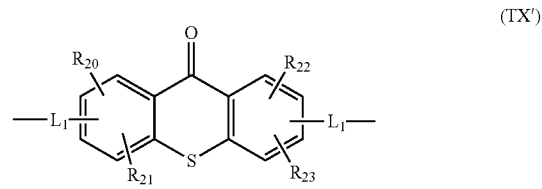 (TX')

L is $C_1$-$C_{20}$alkylene-S,

Q is a direct bond, $C_1$-$C_8$alkylene or $C_1$-$C_8$alkylene which is interrupted by one or more O;

$L_1$ is direct bond, CO; unsubstituted $C_1$-$C_{20}$alkylene, $C_1$-$C_{20}$alkylene which is substituted by phenyl or one or more OH; $C_1$-$C_{20}$alkylene which is interrupted by one or more O, S, or $NR_{24}$; $C_1$-$C_{20}$alkylene which is interrupted by one or more O, S, or $NR_{24}$ and is substituted by OH;

or is unsubstituted $C_1$-$C_{20}$alkylene-O—(CO) or $C_1$-$C_{20}$alkylene-O—(CO) which is substituted by OH, or is $C_1$-$C_{20}$alkylene-O—(CO) wherein the alkylene is interrupted by one or more O; $C_1$-$C_{20}$alkylene-N($R_{19}$)(CO), $C_1$-$C_{20}$alkylene-S, $C_1$-$C_{20}$alkylene-O, $C_1$-$C_{20}$alkylene-(N$R_{19}$) or $C_1$-$C_{20}$alkylene-(CO)—N($R_{19}$), where in the groups $C_1$-$C_{20}$alkylene-O—(CO) or $C_1$-$C_{20}$alkylene-O—(CO) which is substituted by OH, or is $C_1$-$C_{20}$alkylene-O—(CO) wherein the alkylene is interrupted by one or more O; $C_1$-$C_{20}$alkylene-N($R_{19}$)(CO), $C_1$-$C_{20}$alkylene-S, $C_1$-$C_{20}$alkylene-O, $C_1$-$C_{20}$alkylene-(N$R_{19}$) or $C_1$-$C_{20}$alkylene-(CO)—N($R_{19}$), the linkage to the thioxanthone group is intended to be via the heteroatom N, S or O or via the CO group; or $L_1$ is (CO)—$C_1$-$C_{20}$alkylene-O, where the linkage to the thioxanthone group is via the O atom; or $L_1$ is (CO)-Q;

Y is an n-valent cationic counter ion;

$R_{14}$ is —CH=$CH_2$ or —C($CH_3$)=$CH_2$;

$R_{15}$, $R_{16}$, $R_{17}$ and $R_{18}$ independently of one another are hydrogen;

$R_{19}$ is hydrogen or $C_1$-$C_6$alkyl;

$R_{20}$, $R_{21}$, $R_{22}$ and $R_{23}$ independently of one another have one of the meanings as defined for $R_{15}$, $R_{16}$, $R_{17}$ and $R_{18}$;

$R_{24}$ is hydrogen, $C_1$-$C_{10}$alkyl or $C_1$-$C_{10}$alkyl which is substituted by OH; and $R_{25}$, $R_{26}$, $R_{27}$, $R_{28}$ and $R_{29}$ independently of one another are $C_1$-$C_4$alkyl.

2. The coated substrate according to claim 1, wherein component (B) is an organic material which is polymerized or crosslinked by a base-catalyzed reaction.

3. The coated substrate according to claim 1, wherein component (B) is one of the following systems:
 a) acrylic copolymers with alkoxysilane and/or alkoxysiloxane side groups;
 b) two-component systems comprising hydroxyl-containing polyacrylates, polyesters and/or polyethers and aliphatic or aromatic polyisocyanates;

c) two-component systems comprising functional polyacrylates and polyepoxide, the polyacrylate containing thiol, amino, carboxyl and/or anhydride groups;
d) two-component systems comprising fluorine-modified or silicone-modified, hydroxyl-containing polyacrylates, polyesters and/or polyethers and aliphatic or aromatic polyisocyanates;
e) two-component systems comprising (poly)ketimines and aliphatic or aromatic polyisocyanates;
f) two-component systems comprising (poly)ketimines and unsaturated acrylic resins or acetoacetate resins or methyl α-acrylamidomethylglycolate;
h) two-component systems comprising (poly)oxazolidines and polyacrylates containing anhydride groups or unsaturated acrylic resins or polyisocyanates;
i) two-component systems comprising epoxy-functional polyacrylates and carboxyl-containing or amino-containing polyacrylates;
l) polymers based on allyl glycidyl ether;
m) two-component systems comprising a (poly)alcohol and/or polythiol and a (poly)isocyanate;
n) two-component systems comprising an α,β-ethylenically unsaturated carbonyl compound and a polymer containing activated $CH_2$ groups;
o) two-component systems comprising a polymer containing activated $CH_2$ groups, the activated $CH_2$ groups being present either in the main chain or in the side chain or in both, or a polymer containing activated $CH_2$ groups such as (poly)acetoacetates and (poly)cyanoacetates, and a polyaldehyde crosslinker;
p) two-component or one-component systems comprising blocked isocyanates and a hydrogen donor;
q) thiol Micheal systems.

4. The coated substrate according to claim 1, wherein component (B) is an epoxy resin or a mixture of different epoxy resins.

5. The coated substrate according to claim 1, wherein component (A) is present in an amount of from 0.01 to 20% by weight based on component (B).

6. The coated substrate according to claim 1, wherein the composition coated on the at least one surface further comprises a sensitizer (C) selected from the group consisting of benzophenone and benzophenone derivatives.

7. The coated substrate according to claim 4, wherein for the photolatent base compound
X is O or $NR_{10}$.

8. The coated substrate according to claim 1, wherein for the photolatent base compound
Ar is phenylene;
$R_1$, and $R_2$ independently of one another other are hydrogen;
$R_{11}$ is hydrogen or $C_1$-$C_6$-alkyl;
$R_{12}$ and $R_{13}$ independently of each other are hydrogen or $C_1$-$C_1$-alkyl;
n in the compounds of the formula (Ib) and (Ic) is 1 or 2; and in the compounds of formula (IIIb) or (IIIc) is 1;
X is O, S, $NR_{10}$ or a direct bond;
$R_{10}$ is hydrogen;
A when n is 1, is $C_1$-$C_{18}$-alkyl which is interrupted by one or more O or is uninterrupted $C_1$-$C_1$alkyl which is substituted by $OR_{11}$, $NR_{12}R_{13}$ or $OCOR_4$;
or A is a group (TX) or (BP);
or, when X is O, additionally X-A denotes $X^-$ $Y^+$;
$L_1$ is $C_1$-$C_8$alkylene-S;
L is $C_1$-$C_8$alkylene-S;
$R_{14}$ is —CH=$CH_2$;
$R_{15}$, $R_{16}$, $R_{17}$ and $R_{18}$ are hydrogen;

$R_{20}$, $R_{21}$, $R_{22}$ and $R_{23}$ are hydrogen;
A when n is greater than 1, is an n-valent saturated or unsaturated $C_2$-$C_{50}$hydrocarbon radical is $C_2$-$C_{13}$-alkylene, which optionally is interrupted by one or more O and which uninterrupted or interrupted $C_2$-$C_{13}$-alkylene is unsubstituted or is substituted by $OR_{11}$;
or A when n is greater than 1, is an n-valent polyalkylene imine which is uninterrupted or is interrupted by (CO), (CO)O or a double bond and which uninterrupted or interrupted n-valent polyalkylene imine is unsubstituted or is substituted by

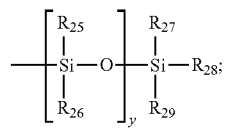

$A_1$, when n is 1, is hydrogen or $C_2$-$C_{13}$-alkanoyl which is unsubstituted or substituted by $COOR_{12}$;
$R_{25}$, $R_{26}$, $R_{27}$, $R_{28}$ and $R_{29}$ are methyl;
y is an integer from 1-12; and
Y as an n-valent cationic counter ion, is an alkali metal.

9. The coated substrate according to claim 1, wherein for the photolatent base compound
X is O.

10. The coated substrate according to claim 1, wherein the photolatent base compound is selected from the group consisting of

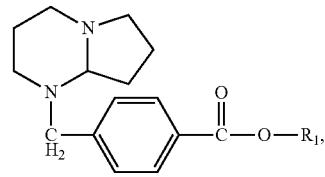

where $R_1$ is $(CH_2)_6$—OH,

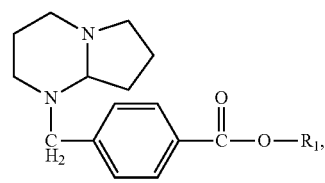

where $R_1$ is $(CH_2)_2OCH_3$,

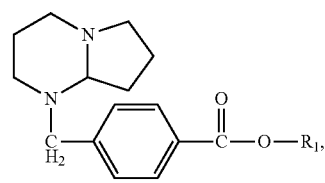

where $R_1$ is $(CH_2)_2$—O—$(CH_2)_2OC_2H_5$,

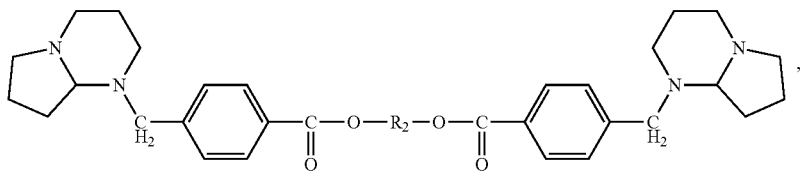

where R₂ is CH₂CH₂,

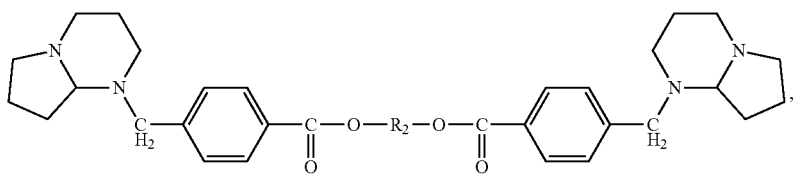

where R₂ is

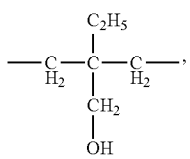

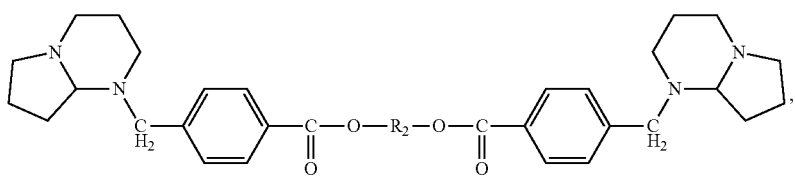

where R₂ is (CH₂)₆,
4-(hexahydro-pyrrolo[1,2-a]pyrimidin-1-ylmethyl)-benzoic acid 2-(2-hydroxy-ethoxy)-ethyl ester,
diethyleneglycole di[4-(hexahydro-pyrrolo[1,2-a]pyrimidin-1-ylmethyl)-benzoate],
[4-(hexahydro-pyrrolo[1,2-a]pyrimidin-1-ylmethyl)-phenyl]-methanol,
hexanoic acid 4-(hexahydro-pyrrolo[1,2-a]pyrimidin-1-ylmethyl)-benzyl ester,
hexanedioic acid 4-(hexahydro-pyrrolo[1,2-a]pyrimidin-1-ylmethyl)-benzyl ester methyl ester,
potassium 4-(hexahydro-pyrrolo[1,2-a]pyrimidin-1-ylmethyl)-benzoate,
4-(hexahydro-pyrrolo[1,2-a]pyrimidin-1-ylmethyl)-benzoic acid 2-(9-oxo-9H-thioxanthen-3-ylsulfanyl)-ethyl ester,
4-(hexahydro-pyrrolo[1,2-a]pyrimidin-1-ylmethyl)-benzoic acid 2-(4-benzoyl-phenylsulfanyl)-ethyl ester,
4-(hexahydro-pyrrolo[1,2-a]pyrimidin-1-ylmethyl)-benzoic acid allyl ester,
N-allyl-4-(hexahydro-pyrrolo[1,2-a]pyrimidin-1-ylmethyl)-benzamide,
4-(hexahydro-pyrrolo[1,2-a]pyrimidin-1-ylmethyl)-N-hexyl-benz-amide,
4-(hexahydro-pyrrolo[1,2-a]pyrimidin-1-ylmethyl)-N-(2-hydroxy-ethyl)-benzamide,
4-(hexahydro-pyrrolo[1,2-a]pyrimidin-1-ylmethyl)-N-(3-hydroxy-propyl)-benzamide,
1-[4-(hexahydro-pyrrolo[1,2-a]pyrimidin-1-ylmethyl)-phenyl]-ethanone,
4-(hexahydro-pyrrolo[1,2-a]pyrimidin-1-ylmethyl)-benzoic acid 6-amino-hexyl ester,
4-(hexahydro-pyrrolo[1,2-a]-pyrimidin-1-ylmethyl)-benzamide of poly(ethylene imine),

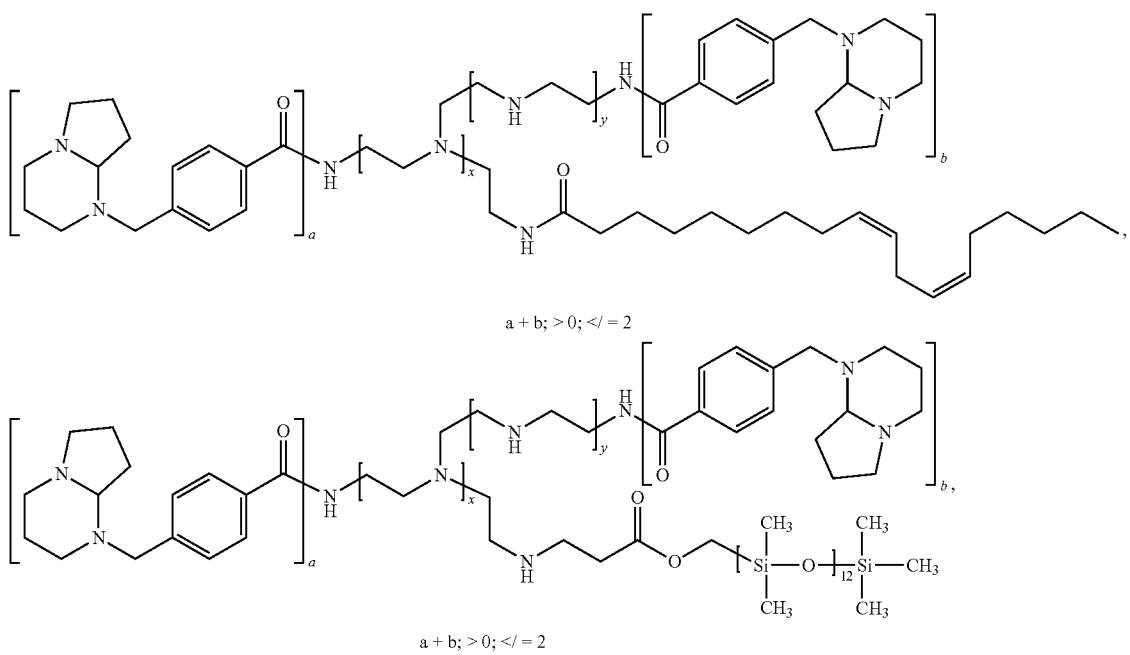

$a + b; > 0; </= 2$ $a + b; > 0; </= 2$ and
4-(hexahydro-pyrrolo[1,2-a]pyrimidin-1-ylmethyl)-benzoic acid 6-acryloyloxy-hexyl ester.

11. A process for carrying out base-catalysed reactions to prepare a component selected from the group consisting of coatings, adhesives, inks, moulding compounds, and photostructured layers, the process comprising:
providing the coated substrate of claim 1; and
irradiating the coated substrate with light having a wavelength of from 200 nm to 650 nm.

12. The process according to claim 11, wherein component (B) is an organic material which is polymerized or crosslinked by a base-catalyzed reaction.

13. The process according to claim 11, wherein component (B) is one of the following systems:
a) acrylic copolymers with alkoxysilane and/or alkoxysiloxane side groups;
b) two-component systems comprising hydroxyl-containing polyacrylates, polyesters and/or polyethers and aliphatic or aromatic polyisocyanates;
c) two-component systems comprising functional polyacrylates and polyepoxide, the polyacrylate containing thiol, amino, carboxyl and/or anhydride groups;
d) two-component systems comprising fluorine-modified or silicone-modified, hydroxyl-containing polyacrylates, polyesters and/or polyethers and aliphatic or aromatic polyisocyanates;
e) two-component systems comprising (poly)ketimines and aliphatic or aromatic polyisocyanates;
f) two-component systems comprising (poly)ketimines and unsaturated acrylic resins or acetoacetate resins or methyl α-acrylamidomethylglycolate;
h) two-component systems comprising (poly)oxazolidines and polyacrylates containing anhydride groups or unsaturated acrylic resins or polyisocyanates;

i) two-component systems comprising epoxy-functional polyacrylates and carboxyl-containing or amino-containing polyacrylates;
l) polymers based on allyl glycidyl ether;
m) two-component systems comprising a (poly)alcohol and/or polythiol and a (poly)isocyanate;
n) two-component systems comprising an α,β-ethylenically unsaturated carbonyl compound and a polymer containing activated $CH_2$ groups;
o) two-component systems comprising a polymer containing activated $CH_2$ groups, the activated $CH_2$ groups being present either in the main chain or in the side chain or in both, or a polymer containing activated $CH_2$ groups such as (poly)acetoacetates and (poly)cyanoacetates, and a polyaldehyde crosslinker;
p) two-component or one-component systems comprising blocked isocyanates and a hydrogen donor;
q) thiol Micheal systems.

14. The process according to claim 11, wherein component (B) is an epoxy resin or a mixture of different epoxy resins.

15. The process according to claim 11, wherein component (A) is present in an amount of from 0.01 to 20% by weight based on component (B).

16. The process according to claim 11, further comprising a sensitizer (C) selected from the group consisting of benzophenone and benzophenone derivatives.

17. The process according to claim 11, further comprising heating prior to, during, or after irradiating the composition with light.

18. The process according to claim 11, wherein the photolatent base compound of the formula (Ib), (IIb), (IIIb), (Ic), (IIc), or (IIIc) photoinitiates a photochemically induced, base-catalysed polymerization, addition, or substitution reaction.

* * * * *